United States Patent
Selvaraj et al.

(10) Patent No.: US 9,891,235 B2
(45) Date of Patent: Feb. 13, 2018

(54) PATHWAY SPECIFIC ASSAYS FOR PREDICTING IRRITABLE BOWEL SYNDROME DIAGNOSIS

(71) Applicant: NESTEC S.A., Vevey (CH)

(72) Inventors: Fabiyola Selvaraj, San Diego, CA (US); Fred Princen, La Jolla, CA (US); Sharat Singh, Rancho Santa Fe, CA (US)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 14/938,710

(22) Filed: Nov. 11, 2015

(65) Prior Publication Data
US 2016/0130279 A1 May 12, 2016

Related U.S. Application Data

(63) Continuation of application No. PCT/IB2014/061634, filed on May 22, 2014.
(Continued)

(51) Int. Cl.
C07D 498/04 (2006.01)
C07D 495/04 (2006.01)
(Continued)

(52) U.S. Cl.
CPC ....... G01N 33/6893 (2013.01); C07D 495/04 (2013.01); C07D 498/04 (2013.01);
(Continued)

(58) Field of Classification Search
CPC .. C07D 519/00; C07D 498/04; C07D 495/04; G01N 33/6893; G01N 33/942;
(Continued)

(56) References Cited

U.S. PATENT DOCUMENTS

2006/0154276 A1   7/2006   Lois et al.
2016/0139148 A1   5/2016   Westin et al.

FOREIGN PATENT DOCUMENTS

WO   2011/066458 A2   6/2011
WO   2014/053996 A2   4/2014

OTHER PUBLICATIONS

Todoroki et al. Online photocatalytic device for highly selective pre-column fluorescence derivatization of 5-hydroxyindoles with benzylamine. Analytica Chimica Acta 2006, vol. 555, pp. 14-19.*
(Continued)

Primary Examiner — Shafiqul Haq
(74) Attorney, Agent, or Firm — Kilpatrick Townsend and Stockton LLP

(57) ABSTRACT

The present invention provides antibodies and methods for preparing antibodies to metabolites in the serotonin, tryptophan, kynurenine pathways. The prepared antibodies have low cross-reactivity to related metabolites, and are useful reagents for specific and sensitive immunoassays The present invention also provides stable derivatives of various metabolites and short chain fatty acids. The derivative can be conjugated to a biomolecule such as a carrier protein and combined with an adjuvant to stimulate an immune response. The derivatives can also be conjugated to other biomolecules.

5 Claims, 20 Drawing Sheets

Related U.S. Application Data

(60) Provisional application No. 61/827,506, filed on May 24, 2013.

(51) Int. Cl.

| | | |
|---|---|---|
| *C07D 519/00* | (2006.01) | |
| *C07K 16/44* | (2006.01) | |
| *G01N 33/68* | (2006.01) | |
| *C07K 16/12* | (2006.01) | |
| *C07K 16/26* | (2006.01) | |
| *G01N 33/94* | (2006.01) | |

(52) U.S. Cl.
CPC ............ *C07D 519/00* (2013.01); *C07K 16/12* (2013.01); *C07K 16/26* (2013.01); *C07K 16/44* (2013.01); *G01N 33/6812* (2013.01); *G01N 33/942* (2013.01); *C07K 2317/33* (2013.01); *G01N 2800/065* (2013.01); *G01N 2800/52* (2013.01)

(58) Field of Classification Search
CPC ......... G01N 33/6812; G01N 2800/065; G01N 2800/52; C07K 16/12; C07K 16/26; C07K 16/44; C07K 2317/33
See application file for complete search history.

(56) References Cited

OTHER PUBLICATIONS

Chauveau, J. et al., "Rapid and specific enzyme immunoassay of serotonin," Clinical Chemistry, 37(7):1178-1184, 1991.

Chien-Sheng, C. et al., "Identification of novel serological biomarkers for inflammatory bowel disease using *Escherichia coli* proteome chip," Molecular & Cellular Proteomics, 8(8):1765-76, 2009.

Huisman, H. et al,. "Studies on the immune response and preparation of antibodies against a large panel of conjugated neurotransmitters and biogenic amines: specific polyclonal antibody response and tolerance," Journal of Neurochemistry, 112(3):829-841, 2010.

Makosza, M. et al., "Synthesis of 1,3,4,5-tetrahydropyrrolo[4,3,2-de]quinolines via the vicarious nucleophilic substitution of hydrogen," Tetrahedron, 51(26):7263-7276, 1995.

Nichkova, M. et al., "Evaluation of a novel ELISA for serotonin: urinary serotonin as a potential biomarker for depression," Analytical and Bioanalytical Chemistry, 402(4):1593-1600, 2011.

Plevy, S. et al., "Combined serologic, genetic, and inflammatory markers can accurately differentiate non-IBD, Crohn's disease, and ulcerative colitis patients," Gastroenterology, 142(5, S1):S41, 2012.

Plevy, S. et al., "Combined serological, genetic, and inflammatory markers differentiate non-IBD, Crohn's disease, and ulcerative colitis patients," Inflammatory Bowel Diseases, 19(6):1139-48, 2013.

Todoroki, K. et al., "Online photocatalytic device for highly selective pre-column fluorescence derivatization of 5-hydroxyindoles with benzylamine," Analytica Chimica Acta, 555(1):14-19, 2006.

Yamagishi, Y. et al., "Ribosomal synthesis of cyclic peptides with a fluorogenic oxidative coupling reaction," Chembiochem, 10(9):1469-1472, 2009.

\* cited by examiner

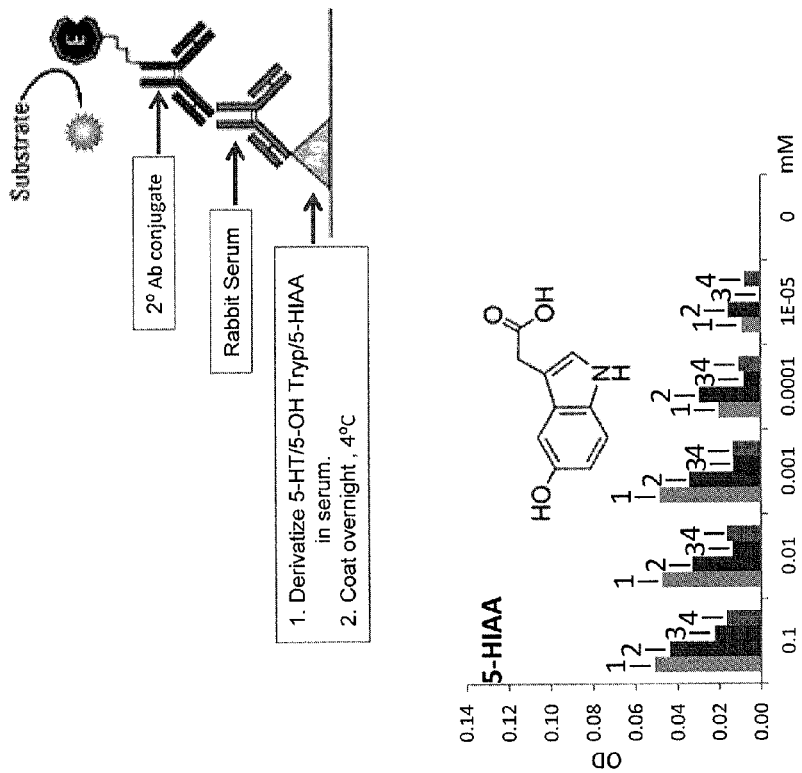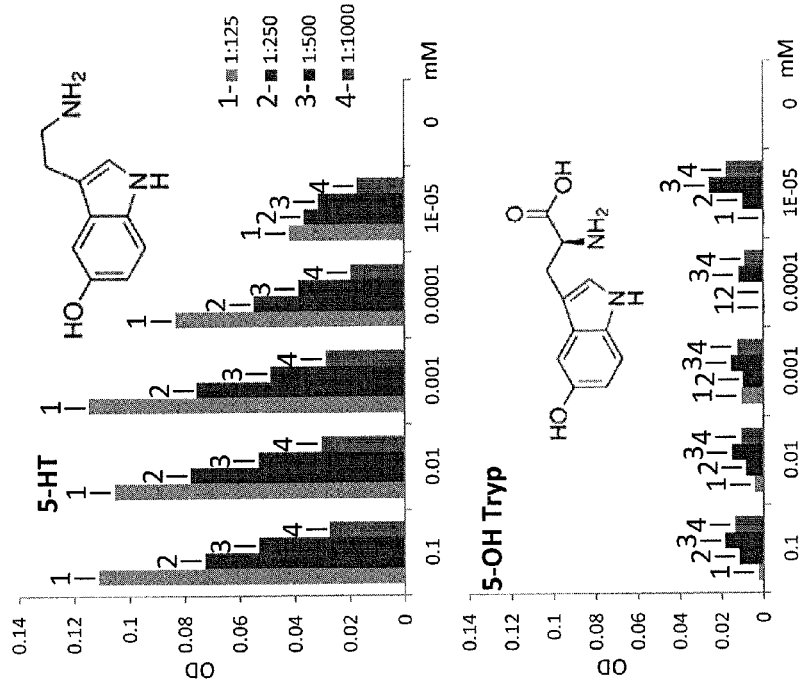
FIG. 11A  FIG. 11B  FIG. 11C  FIG. 11D

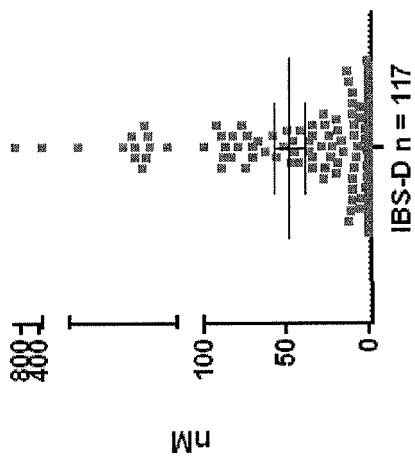
FIG. 13A
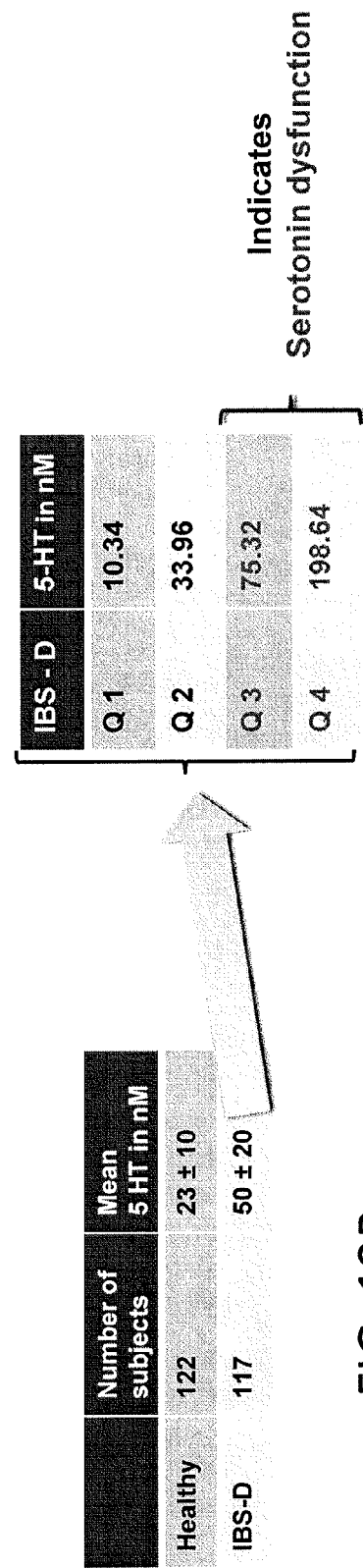
FIG. 13B
FIG. 13C
ELISA:

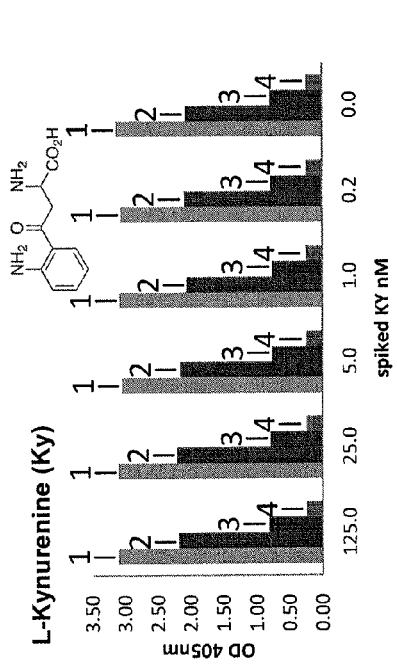
FIG. 18B
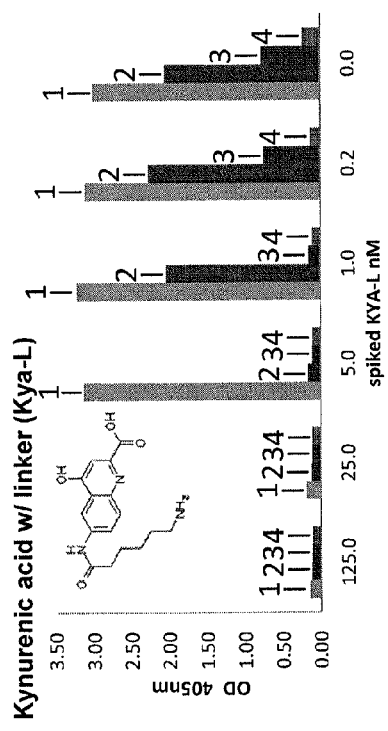
FIG. 18A
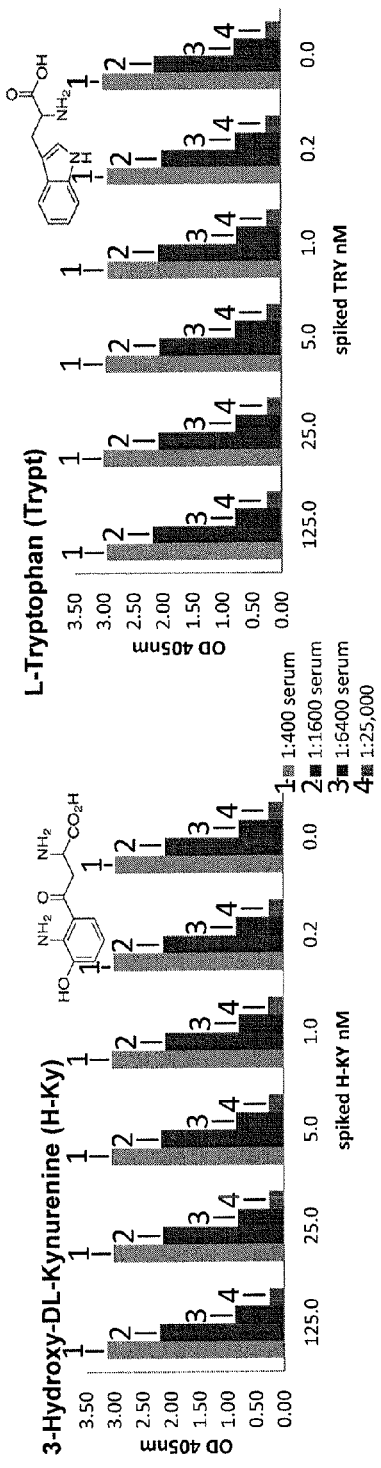
FIG. 18D
FIG. 18C

PATHWAY SPECIFIC ASSAYS FOR PREDICTING IRRITABLE BOWEL SYNDROME DIAGNOSIS

CROSS-REFERENCES TO RELATED APPLICATIONS

This application is a continuation of PCT/IB2014/061634, filed May 22, 2014, which application claims priority to U.S. Provisional Patent App. No. 61/827,506, filed May 24, 2013, the teachings of which are hereby incorporated by reference in their entireties for all purposes. This application incorporates by reference PCT/IB2014/061636, filed May 22, 2014.

BACKGROUND OF THE INVENTION

Irritable bowel syndrome (IBS) is the most common of all gastrointestinal disorders, affecting 10-20% of the general population and accounting for more than 50% of all patients with digestive complaints. However, studies suggest that only about 10% to 50% of those afflicted with IBS actually seek medical attention. Patients with IBS present with disparate symptoms such as, for example, abdominal pain predominantly related to defecation, diarrhea, constipation or alternating diarrhea and constipation, abdominal distention, gas, and excessive mucus in the stool. More than 40% of IBS patients have symptoms so severe that they have to take time off from work, curtail their social life, avoid sexual intercourse, cancel appointments, stop traveling, take medication, and even stay confined to their house for fear of embarrassment. The estimated health care cost of IBS in the United States is $8 billion per year (Talley et al., *Gastroenterol.*, 109:1736-1741 (1995)).

IBS patients are classified into three groups according to their predominant bowel symptoms: constipation-predominant IBS (IBS-C), diarrhea-predominant IBS (IBS-D), IBS with alternating symptoms of diarrhea and constipation (IBS-M), and unsubtyped IBS (IBS-U). In current clinical practice, diagnosis of IBS is based on the Rome III criteria and according to the symptoms presented by the patients. There are no specific biological, radiographic, endoscopic or physiological biomarkers that can be used to identify this disorder.

Irritable bowel syndrome is a heterogeneous gastrointestinal (GI) function disorder. There is increasing evidence pointing to the involvement of the immune system in its pathogenesis. GI infection may be a triggering factor for causing the onset of IBS symptoms. On the other hand, IBS is often described as a "brain-gut disorder." Alterations in GI motility and secretion mediated by dysregulation of the 5-HT signaling pathway can underlie the irregularities in bowel habits. Activation of mast cells in proximity to colonic nerves correlated with the abnormal pain experienced by patients with IBS. Mast cells are well known to be capable of producing and releasing a variety of inflammatory mediators upon activation. However, it is not clear how these different pathways communicate with each other and whether their interactions behave in the same manner in IBS patients as it is in healthy subjects.

The precise pathophysiology of IBS remains to be elucidated. While gut dysmotility and altered visceral perception are considered important contributors to symptom pathogenesis (Quigley, Scand. J. *Gastroenterol.*, 38(Suppl. 237): 1-8 (2003); Mayer et al., *Gastroenterol.*, 122:2032-2048 (2002)), this condition is viewed as a stress-related disorder characterized by disturbed brain-gut communication, enteric infection, intestinal inflammation, and/or altered microbiota. Recently, roles for enteric infection and intestinal inflammation have also been proposed. Studies have documented the onset of IBS following bacteriologically confirmed gastroenteritis, while others have provided evidence of low-grade mucosal inflammation (Spiller et al., Gut, 47:804-811 (2000); Dunlop et al., *Gastroenterol.*, 125:1651-1659 (2003); Cumberland et al., *Epidemiol. Infect.*, 130:453-460 (2003)) and immune activation (Gwee et al., Gut, 52:523-526 (2003); Pimentel et al., *Am. J. Gastroenterol.*, 95:3503-3506 (2000)) in IBS. The enteric flora (e.g., gut microbiome) has also been implicated, and a recent study demonstrated the efficacy of the probiotic organism *Bifidobacterium* in treating the disorder through modulation of immune activity (Simren et al., Gut, 62:159-176 (2013)).

There is a growing body of evidence supporting the role of antimicrobial antibodies, stress hormones, inflammatory cytokines, and mast cell markers in various intestinal diseases or disorders. For instance, the antimicrobial antibodies OmpC, CBir1, FlaX and Fla2 have been proven to be valuable biomarkers of inflammatory bowel disease (IBD). Subsets of antibodies to *Escherichia coli* K12 proteins (e.g., Era, FocA, FrvX, GabT, YbaN, YcdG, YhgN, and YidX) can be used to distinguish between individuals with Crohn's Disease (CD) and healthy controls, and between individuals with CD and ulcerative colitis (Chen et al., *Mol. Cell Proteomics*, 8:1765-1776, (2009)). Individuals with post-infectious small intestine bacterial outgrowth (SIBO) associated with IBS which is often caused by infection from *Campylobacter jejuni* (*C. jejuni*, Cj), *Escherichia coli* (*E. coli*, Ec), *Salmonella enteritidis* (*S. enteritidis*, Se), *Shigella flexneri* (*S. flexneri*, Sj), may possess antibodies against flagellin proteins of the infecting bacteria (Spiller R and Garsed K., *Gastroenterology*, 136:1979-1988 (2009)).

Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by these bacteria in both post-infectious IBS and non-post-infectious IBS. Measurement of mast cell markers such as β-tryptase, histamine and prostaglandin E2 (PGE2) has important implications in the clinical diagnosis of IBS. Detailed methods of using mast cell markers to aid in the diagnosis of IBS are described in U.S. Pat. No. 8,114,616 and U.S. Patent Application Publication No. 2012/244558, the disclosures of which are hereby incorporated by reference in their entireties for all purposes.

IBS patients typically experience abnormal gut motility and visceral hypersensitivity mediated by the brain-gut axis and the gut microbiome. In stress-sensitive disorders including IBS, stress hormones of the hypothalamic-pituitary-adrenal axis (HPA) axis, such as gut hormones, serotonin, adrenocorticotropin hormone (ACTH), cortisol, corticotropin-releasing hormone, and catecholamine are released, thus controlling the physiological function of, for example, the gut. Dysregulation of the brain-gut axis including the metabolite driven pathways can adversely affect gastrointestinal function by decreasing motility and increasing pain or discomfort. Therapeutics drugs directed to the serotonin pathway are currently under investigation for the treatment of IBS. Dysregulation of intestinal bile acid secretion and absorption is also associated with IBS. Some studies have also shown that gastrointestinal function is affected by the gut microbiome. For instance, diet, antibiotics, pathogens, and the host's immune response can change the gut's microbiome community, which in turn, can alter intestinal function.

In view of the foregoing, there is a need in the art for methods for diagnosing IBS in an individual by monitoring the brain-gut-microbiome axis. Assays are needed to assess whether various metabolic and catabolic pathways are functioning properly. The present invention satisfies these and other needs.

BRIEF SUMMARY OF THE INVENTION

The present invention provides antibodies and methods for preparing antibodies to metabolites in the serotonin, tryptophan and kynurenine pathways. The prepared antibodies have low cross-reactivity to related metabolites, and are useful reagents for specific and sensitive immunoassays for one or more of the following metabolites: serotonin (5-HT), 5-hydroxyindole acetic acid (5-HIAA), 5-hydroxytryptophan (5-HTP), kynurenine (K), kynurenic acid (KA), 3-hydroxykynurenine (3-HK), 3-hydroxyanthranilic acid (3-HAA), quinolinic acid and anthranilic acid.

The present invention also provides stable derivatives of serotonin (5-HT), 5-hydroxyindole acetic acid (5-HIAA), 5-hydroxy tryptophan (5-HTP), kynurenine (K), kynurenic acid (KA), 3-hydroxykynurenine (3-HK), 3-hydroxyanthranilic acid (3-HAA), quinolinic acid and anthranilic acid. The derivative can be conjugated to a biomolecule such as a carrier protein and combined with an adjuvant to stimulate an immune response. The derivative can also be conjugated to other biomolecules.

In other aspects, the present invention provides methods for making antibodies. The method comprises:
 (a) providing an immunogen comprising a derivative selected from the group consisting of serotonin (5-HT), 5-hydroxyindole acetic acid (5-HIAA), 5-hydroxy tryptophan (5-HTP), kynurenine (K), kynurenic acid (KA), 3-hydroxykynurenine (3-HK), 3-hydroxyanthranilic acid (3-HAA), quinolinic acid and anthranilic acid conjugated to a carrier protein;
 (b) immunizing an animal with the immunogen under conditions such that the immune system of the animal makes the antibodies; and
 (c) removing the antibodies from the animal.

In certain other aspects, the present invention provides a method for assaying a member selected from the group consisting of serotonin (5-HT), 5-hydroxyindole acetic acid (5-HIAA), 5-hydroxy tryptophan (5-HTP), kynurenine (K), kynurenic acid (KA), 3-hydroxykynurenine (3-HK), 3-hydroxyanthranilic acid (3-HAA), quinolinic acid, anthranilic acid and a combination thereof, in a fluid or tissue sample from a mammal, such as a human. The method comprises combining the sample with the antibodies described herein, and then determining whether the antibodies specifically bind to a member selected from the group consisting of serotonin (5-HT), 5-hydroxyindole acetic acid (5-HIAA), 5-hydroxy tryptophan (5-HTP), kynurenine (K), kynurenic acid (KA), 3-hydroxykynurenine (3-HK), 3-hydroxyanthranilic acid (3-HAA), quinolinic acid, anthranilic acid and a combination thereof, from the sample. For example, in these methods, specific antibody binding to serotonin (5-HT) from the sample indicates that serotonin (5-HT) is present in the sample.

The present invention also provides antibodies and methods for preparing antibodies to bile acid metabolites. The prepared antibodies have low cross-reactivity to related metabolites, and are useful reagents for specific and sensitive immunoassays for 7-α-hydroxy-4-cholesten-3-one.

The present invention also provides stable derivatives of 7-α-hydroxy-4-cholesten-3-one. The derivative can be conjugated to a biomolecule such as a carrier protein and combined with an adjuvant to stimulate an immune response. The derivative can also be conjugated to other biomolecules.

In other aspects, the present invention provides methods for making antibodies of 7-α-hydroxy-4-cholesten-3-one. The method comprises:
 (a) providing an immunogen comprising a derivative of 7-α-hydroxy-4-cholesten-3-one conjugated to a carrier protein;
 (b) immunizing an animal with the immunogen under conditions such that the immune system of the animal makes the antibodies; and
 (c) removing the antibodies from the animal.

In certain other aspects, the present invention provides a method of assaying for 7-α-hydroxy-4-cholesten-3-one in a fluid or tissue sample from a mammal, such as a human. The method comprises combining the sample with the antibodies described herein, then determining whether the antibodies specifically bind to 7-α-hydroxy-4-cholesten-3-one from the sample. For example, in these methods, specific antibody binding to 7-α-hydroxy-4-cholesten-3-one from the sample indicates that 7-α-hydroxy-4-cholesten-3-one is present in the sample.

In addition, the present invention provides antibodies and methods of making antibodies to short chain fatty acids. The prepared antibodies have low cross-reactivity to related metabolites, and are useful reagents for specific and sensitive immunoassays for propionic acid and butyric acid.

The present invention also provides stable derivatives of short chain fatty acids (SCFA) such as propionic acid and butyric acid. The derivative can be conjugated to a biomolecule such as a carrier protein and combined with an adjuvant to stimulate an immune response. The derivative can also be conjugated to other biomolecules.

In other aspects, the present invention provides methods for making antibodies of short chain fatty acids. The method comprises:
 (a) providing an immunogen comprising a derivative of a short chain fatty acid conjugated to a carrier protein;
 (b) immunizing an animal with the immunogen under conditions such that the immune system of the animal makes the antibodies; and
 (c) removing the antibodies from the animal.

In certain other aspects, the present invention provides a method for assaying a short chain fatty acid in a fluid or tissue sample from a mammal, such as a human. The method comprises combining the sample with the antibodies described herein, then determining whether the antibodies specifically bind to a short chain fatty acids from the sample. For example, in these methods, specific antibody binding to propionic acid from the sample indicates that propionic acid is present in the sample.

In addition to the foregoing, the present invention provides a method for determining a diagnosis of Irritable Bowel Syndrome (IBS) in a subject using the presence or concentrations of the metabolites herein. The method comprises measuring one or more metabolites in blood, plasma or serum of the patient by the assay methods described herein.

The present invention also provides a method for determining whether a treatment for IBS in a patient is efficacious. The method comprises measuring one or more metabolites in blood, plasma or serum of the patient by the assay methods described herein.

In certain other aspects, the present invention provides a method for evaluating a patient previously diagnosed with IBS. The method comprises measuring one or more metabolites in blood, plasma or serum of the patient by an assay method described herein.

These and other aspects, advantages and embodiments will become more apparent when read with the detailed description and figures which follow.

BRIEF DESCRIPTION OF THE DRAWINGS

FIGS. 11A-D illustrate lack of cross-reactivity of the antiserum using the direct assay as diagramed in FIG. 11B. The antiserum is specific to 5-HT (FIG. 11A) and showed no cross-reactivity to structurally similar compounds such as 5-hydroxytryptophan (5-OH Tryp; FIG. 11C) and 5-hydroxyindoleacetic acid (5-HIAA; FIG. 11D).

FIG. 12A shows that the presence of Ser-D in the human serum inhibited the binding of the anti-Ser-D antibodies to the biotinylated Ser-D. Less antibody was detected as the amount of free Ser-D increased. FIGS. 12C-E show there was no change or a slight change in the amount of antibody bound to the biotinylated Ser-D when the tryptophan (FIG. 12C), 5-hydroxytryptophan (FIG. 12D), and 5-hydroxyindoleaceticacid (FIG. 12E) derivatives were present.

FIGS. 13A-C show that the mean amount of serotonin in the IBS-D patients was significantly different compared to in healthy controls. FIG. 13A shows a graph of ELISA data. FIG. 13B shows tabulated summary of the data and FIG. 13C shows quartile analysis.

FIGS. 18A-D illustrate the lack of cross-reactivity of the anti-KYA-L antibody. FIG. 18A shows that the KYA-L antigen competed with the biotinylated antigen. In contrast, the presence of increasing amounts of Ky (FIG. 18B), H-Ky (FIG. 18C) and Trypt (FIG. 18D) did not change the level of anti-KYA-L detected in the assay. The results show that the anti-KYA-L antibody does not cross-react with kynurenine metabolites and is specific for kynurenic acid.

DETAILED DESCRIPTION

I. Definitions

Figure 1:
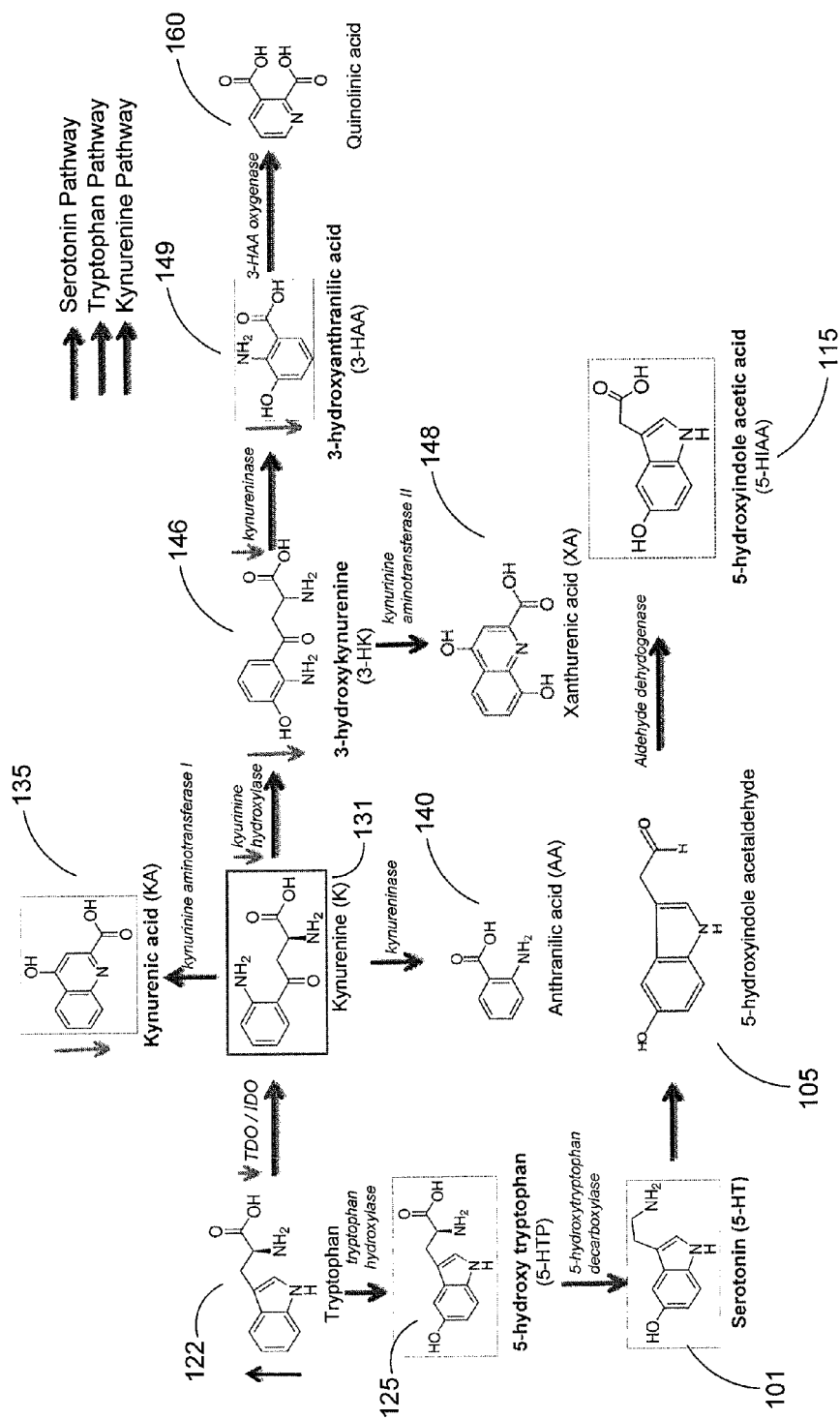
FIG. 1 illustrates the complex pathophysiology of IBS and highlights the metabolites of the serotonin, tryptophan and kynurenine pathways.

The terms "a," "an," or "the" as used herein not only includes aspects with one member, but also includes aspects with more than one member. For example, an embodiment including "a polyamine compound and an excipient" should be understood to present certain aspects with at least a second polyamine compound, at least a second excipient, or both.

The term "assay" includes the detection or quantification of an analyte. Typically, the implementation of an assay requires a correlation of the light output to the amount of peroxidase used, so that peroxidase is the substance determined directly. Although the present invention is useful for determining the presence or amount of any of a reactant (luminol, peroxidase or oxidant), the reactant is not necessarily the substance itself to be determined. For example, the oxidant (e.g., $H_2O_2$) can be produced by a previous reaction, or a series of previous reactions.

The antibody or antigen binding fragment specifically binds to the metabolite of interest with less than 1% cross-reactivity to other metabolites. If any cross-reactivity occurs, the cross reactivity is de minimus, such as less than 1%, or about 0.03-0.9%; or 0.02-0.8%; or 0.05% to 0.5% or 0.03%-0.9% of cross-reactivity to another metabolite.

"Acyl" as used herein includes an alkanoyl, aroyl, heterocycloyl, or heteroaroyl group as defined herein. Representative acyl groups include acetyl, benzoyl, nicotinoyl, and the like.

"Alkanoyl" as used herein includes an alkyl-C(O)— group wherein the alkyl group is as defined herein. Representative alkanoyl groups include acetyl, ethanoyl, and the like.

"Alkenyl" as used herein includes a straight or branched aliphatic hydrocarbon group of 2 to about 15 carbon atoms that contains at least one carbon-carbon double or triple bond. Preferred alkenyl groups have 2 to about 12 carbon atoms. More preferred alkenyl groups contain 2 to about 6 carbon atoms. In one aspect, hydrocarbon groups that contain a carbon-carbon double bond are preferred. In a second aspect, hydrocarbon groups that contain a carbon-carbon triple bond are preferred (i.e., alkynyl). "Lower alkenyl" as used herein includes alkenyl of 2 to about 6 carbon atoms. Representative alkenyl groups include vinyl, allyl, n-butenyl, 2-butenyl, 3-methylbutenyl, n-pentenyl, heptenyl, octenyl, decenyl, propynyl, 2-butynyl, 3-methylbutynyl, n-pentynyl, heptynyl, and the like.

An alkenyl group can be unsubstituted or optionally substituted. When optionally substituted, one or more hydrogen atoms of the alkenyl group (e.g., from 1 to 4, from 1 to 2, or 1) may be replaced with a moiety independently selected from the group consisting of fluoro, hydroxy, alkoxy, amino, alkylamino, acylamino, thio, and alkylthio.

"Alkenylene" as used herein includes a straight or branched bivalent hydrocarbon chain containing at least one carbon-carbon double or triple bond. Preferred alkenylene groups include from 2 to about 12 carbons in the chain, and more preferred alkenylene groups include from 2 to 6 carbons in the chain. In one aspect, hydrocarbon groups that contain a carbon-carbon double bond are preferred. In a second aspect, hydrocarbon groups that contain a carbon-carbon triple bond are preferred. Representative alkenylene groups include —CH=CH—, —CH$_2$—CH=CH—, —C(CH$_3$)=CH—, —CH$_2$CH=CHCH$_2$—, ethynylene, propynylene, n-butynylene, and the like.

"Alkoxy" as used herein includes an alkyl-O— group wherein the alkyl group is as defined herein. Representative alkoxy groups include methoxy, ethoxy, n-propoxy, i-propoxy, n-butoxy, heptoxy, and the like.

An alkoxy group can be unsubstituted or optionally substituted. When optionally substituted, one or more hydrogen atoms of the alkoxy group (e.g., from 1 to 4, from 1 to 2, or 1) may be replaced with a moiety independently selected from the group consisting of fluoro, hydroxy, alkoxy, amino, alkylamino, acylamino, thio, and alkylthio.

"Alkoxyalkyl" as used herein includes an alkyl-O-alkylene- group wherein alkyl and alkylene are as defined herein. Representative alkoxyalkyl groups include methoxyethyl, ethoxymethyl, n-butoxymethyl and cyclopentylmethyloxyethyl.

"Alkoxycarbonyl" as used herein includes an ester group; i.e., an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" as used herein includes an alkyl-O—CO-alkylene- group wherein alkyl and alkylene are as defined herein. Representative alkoxycarbonylalkyl include methoxycarbonylmethyl, ethoxy carbonyl methyl, methoxycarbonylethyl, and the like.

"Alkyl" as used herein includes an aliphatic hydrocarbon group, which may be straight or branched-chain, having about 1 to about 20 carbon atoms in the chain. Preferred alkyl groups have 1 to about 12 carbon atoms in the chain. More preferred alkyl groups have 1 to 6 carbon atoms in the chain. "Branched-chain" as used herein includes that one or more lower alkyl groups such as methyl, ethyl or propyl are attached to a linear alkyl chain. "Lower alkyl" as used herein includes 1 to about 6 carbon atoms, preferably 5 or 6 carbon atoms in the chain, which may be straight or branched. Representative alkyl groups include methyl, ethyl, n-propyl, isopropyl, n-butyl, t-butyl, n-pentyl, and 3-pentyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group consisting of fluoro, hydroxy, alkoxy, amino, alkylamino, acylamino, thio, and alkylthio.

"Alkylene" as used herein includes a straight or branched bivalent hydrocarbon chain of 1 to about 6 carbon atoms. Preferred alkylene groups are the lower alkylene groups having 1 to about 4 carbon atoms. Representative alkylene groups include methylene, ethylene, and the like.

"Alkylthio" as used herein includes an alkyl-S— group wherein the alkyl group is as defined herein. Preferred alkylthio groups are those wherein the alkyl group is lower alkyl. Representative alkylthio groups include methylthio, ethylthio, isopropylthio, heptylthio, and the like.

"Alkylthioalkyl" as used herein includes an alkylthio-alkylene- group wherein alkylthio and alkylene are defined herein. Representative alkylthioalkyl groups include methylthiomethyl, ethylthiopropyl, isopropylthioethyl, and the like.

"Amido" as used herein includes a group of formula $Y_1Y_2N$—C(O)— wherein $Y_1$ and $Y_2$ are independently hydrogen, alkyl, or alkenyl; or $Y_1$ and $Y_2$, together with the nitrogen through which $Y_1$ and $Y_2$ are linked, join to form a 4- to 7-membered azaheterocyclyl group (e.g., piperidinyl). Representative amido groups include primary amido ($H_2N$—C(O)—), methylamido, dimethylamido, diethylamido, and the like. Preferably, "amido" is an —C(O)NRR' group where R and R' are members independently selected from the group consisting of H and alkyl. More preferably, at least one of R and R' is H.

"Amidoalkyl" as used herein includes an amido-alkylene- group wherein amido and alkylene are defined herein. Representative amidoalkyl groups include amidomethyl, amidoethylene, dimethylamidomethyl, and the like.

"Amino" as used herein includes a group of formula $Y_1Y_2N$— wherein $Y_1$ and $Y_2$ are independently hydrogen, acyl, or alkyl; or $Y_1$ and $Y_2$, together with the nitrogen through which $Y_1$ and $Y_2$ are linked, join to form a 4- to 7-membered azaheterocyclyl group (e.g., piperidinyl). Optionally, when $Y_1$ and $Y_2$ are independently hydrogen or alkyl, an additional substituent can be added to the nitrogen, making a quaternary ammonium ion. Representative amino groups include primary amino ($H_2N$—), methylamino, dimethylamino, diethylamino, and the like. Preferably, "amino" is an —NRR' group where R and R' are members independently selected from the group consisting of H and alkyl. Preferably, at least one of R and R' is H.

"Aminoalkyl" as used herein includes an amino-alkylene- group wherein amino and alkylene are defined herein. Representative aminoalkyl groups include aminomethyl, aminoethyl, dimethylaminomethyl, and the like.

"Aroyl" as used herein includes an aryl-CO— group wherein aryl is defined herein. Representative aroyl include benzoyl, naphth-1-oyl and naphth-2-oyl.

"Aryl" as used herein includes an aromatic monocyclic or multicyclic ring system of 6 to about 14 carbon atoms, preferably of 6 to about 10 carbon atoms. Representative aryl groups include phenyl and naphthyl.

"Aromatic ring" as used herein includes 5-12 membered aromatic monocyclic or fused polycyclic moieties that may include from zero to four heteroatoms selected from the group consisting of oxygen, sulfur, selenium, and nitrogen. Exemplary aromatic rings include benzene, pyrrole, furan, thiophene, imidazole, oxazole, thiazole, triazole, pyrazole, pyridine, pyrazine, pyridazine, pyrimidine, naphthalene, benzathiazoline, benzothiophene, benzofurans, indole, benzindole, quinoline, and the like. The aromatic ring group can be substituted at one or more positions with halo, alkyl, alkoxy, alkoxy carbonyl, haloalkyl, cyano, sulfonato, amino sulfonyl, aryl, sulfonyl, aminocarbonyl, carboxy, acylamino, alkyl sulfonyl, amino and substituted or unsubstituted substituents.

"Biomolecule" as used herein includes a natural or synthetic molecule for use in biological systems. Preferred biomolecules include a protein, a peptide, an enzyme substrate, a hormone, an antibody, an antigen, a hapten, an avidin, a streptavidin, a carbohydrate, a carbohydrate derivative, an oligosaccharide, a polysaccharide, and a nucleic acid. More preferred biomolecules include a protein, a peptide, an avidin, a streptavidin, or biotin.

"Carboxy" and "carboxyl" as used herein include a HOC(O)— group (i.e., a carboxylic acid) or a salt thereof.

"Carboxyalkyl" as used herein includes a HOC(O)-alkylene- group wherein alkylene is defined herein. Representative carboxyalkyls include carboxymethyl (i.e., HOC(O)CH$_2$—) and carboxyethyl (i.e., HOC(O)CH$_2$CH$_2$—).

"Cycloalkyl" as used herein includes a non-aromatic mono- or multicyclic ring system of about 3 to about 10 carbon atoms, preferably of about 5 to about 10 carbon atoms. More preferred cycloalkyl rings contain 5 or 6 ring atoms. A cycloalkyl group optionally comprises at least one sp$^2$-hybridized carbon (e.g., a ring incorporating an endocyclic or exocyclic olefin). Representative monocyclic cycloalkyl groups include cyclopentyl, cyclohexyl, cycloheptenyl, cycloheptyl, and the like. Representative multicyclic cycloalkyl include 1-decalin, norbomyl, adamantyl, and the like.

"Cycloalkylene" as used herein includes a bivalent cycloalkyl having about 4 to about 8 carbon atoms. Preferred cycloalkylenyl groups include 1,2-, 1,3-, or 1,4-cis- or trans-cyclohexylene.

"Halo" or "halogen" as used herein includes fluoro, chloro, bromo, or iodo.

"Heteroatom" as used herein includes an atom other than carbon or hydrogen. Representative heteroatoms include O, S, and N. The nitrogen or sulphur atom of the heteroatom is optionally oxidized to the corresponding N-oxide, S-oxide (sulfoxide), or S,S-dioxide (sulfone). In a preferred aspect, a heteroatom has at least two bonds to alkylene carbon atoms (e.g., —C$_1$-C$_9$ alkylene-O—C$_1$-C$_9$ alkylene-). In some embodiments, a heteroatom is further substituted with an acyl, alkyl, aryl, cycloalkyl, heterocyclyl, or heteroaryl group (e.g., —N(Me)-; —N(Ac)—).

"Hydroxyalkyl" as used herein includes an alkyl group as defined herein substituted with one or more hydroxy groups. Preferred hydroxyalkyls contain lower alkyl. Representative hydroxyalkyl groups include hydroxymethyl and 2-hydroxyethyl.

"Linking group" i.e., L, comprises the atoms joining the metabolite derivative with a biomolecule such as a carrier protein, a biotin or streptavidin. See also R. Haugland, Molecular Probes Handbook of Fluorescent Probes and Research Chemicals, Molecular Probes, Inc. (1992). In one embodiment, L represents the linking group precursor before the attachment reaction with a protein, and R$^{11}$ represents the resultant attachment between the compound of the invention and the protein or biotin (i.e., R$^{11}$ is the resultant attachment between the linking group joined to the biomolecule). Preferred reactive funtionalities include phosphoramidite groups, an activated ester (e.g., an NHS ester), thiocyanate, isothiocyanate, maleimide and iodoacetamide. L may comprise a terminal amino, carboxylic acid, or sulfhydryl group covalently attached to the ring. In certain instances, the terminal amino, carboxylic acid, or sulfhydryl group is shown and is represented as -L-NH$_2$, or -L-C(O)OH or -L-SH.

"Oxo" as used herein includes a group of formula >C=O (i.e., a carbonyl group —C(O)—).

"Sulfonato" as used herein includes an —SO$_3^-$ group, preferably balanced by a cation such as H$^+$, Na$^+$, K$^+$, and the like.

"Sulfonatoalkyl" as used herein includes an sulfonatoalkylene- group wherein sulfonato and alkylene are as defined herein. A more preferred embodiment includes alkylene groups having from 2 to 6 carbon atoms, and a most preferred embodiment includes alkylene groups having 2, 3, or 4 carbons. Representative sulfonatoalkyls include sulfonatomethyl, 3-sulfonatopropyl, 4-sulfonatobutyl, 5-sulfonatopentyl, 6-sulfonatohexyl, and the like.

II. Embodiments

Serotonin (5-HT) plays a critical role in the regulation of gastrointestinal motility, secretion and sensation. Imbalances in 5-HT levels in the serotonergic signaling within the enteric nervous system have been associated with various disorders, including irritable bowel syndrome (IBS), functional dyspepsia, non-cardiac chest pain, autism and gastric ulcer formation. Synchronized regulation of 5-HT levels in specific nervous system regions is necessary, and catabolism of 5-HT plays an important role in this regulation. Because the catabolic conversion of 5-HT into other compounds affects the overall levels of 5-HT, formation of these conversion products can be a fundamental factor in 5-HT regulation. Three pathways involving 5-HT are the tryptophan, serotonin and kynurenine pathways. The schematic representation of their connection is illustrated in FIG. 1.

In certain aspects, the present invention provides assays for measuring the metabolites in the tryptophan, serotonin and kynurenine pathways. For example, with reference to FIG. 1, measuring 5-HT 101, 5-HIAA (5-hydroxyindole-3-acetic acid) 115 and the metabolites within the kynurenine pathways, allows for an understanding in aiding the diagnosis of IBS and other pathological phenomena such as carcinoid syndrome, depression, hypertension, autism Alzheimer's and migraine.

Prior art methods of measuring metabolites either are nonexistent or lack sensitivity, specificity and reproducibility. Moreover, metabolites such as 5-HT and 5-HIAA are very unstable making them extremely difficult to measure.

A. Assays for Serotonin Pathway Metabolites

In one aspect, the present invention provides metabolite derivatives and conjugates thereof, methods for antibody production and antibodies of serotonin metabolites. In certain aspects, derivatization is preferred as metabolites such as 5-HT and 5-HIAA are sensitive to oxygen, and thus unstable. The level of serotonin in plasma ranges from about 0.6 to 179 nmol/L. Chemical derivatization of 5-HT and 5-HIAA under mild conditions stabilizes the compounds. Thus, in one aspect, the present invention provides stable benzoxazole derivatives of serotonin metabolites. The stable benzoxazole derivatives can be detected by HPLC with high sensitivity due to their fluorescence.

The present invention provides stable derivatives of serotonin (5-HT) and 5-hydroxyindole acetic acid (5-HIAA).

In one aspect, the present invention provides a compound Formula I:

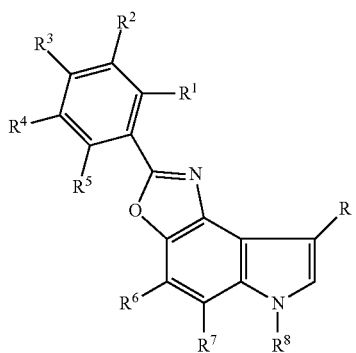

I wherein R is a member selected from the group consisting of alkyl, alkoxy, alkoxyalkyl, aminoalkyl, amidoalkyl, carboxyalkyl, substituted carboxyalkyl; and $R^1$, $R^2$, $R^3$, $R^4$, $R^5$, $R^6$, $R^7$ and $R^8$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}B$;

L is a linker;

$R^{11}$ is the resultant attachment between the compound and a biomolecule; and B is a biomolecule.

In one aspect, R is a member selected from the group consisting of aminoalkyl, carboxyalkyl, and substituted carboxyalkyl. In another aspect, R is a member selected from the group consisting of —$CH_2CH_2NH_2$, —$CH_2CH_2CO_2H$ and —$CH_2CH(NH_2)CO_2H$.

L represents a linking group for attachment to a biomolecule such as a carrier protein or biotin. For example, L may comprise a terminal amino, carboxylic acid, or sulfhydryl group covalently attached to the ring. In certain instances, the terminal amino, carboxylic acid, or sulfhydryl group is shown and is represented as -L-$NH_2$, or -L-C(O)OH or -L-SH.

$R^{11}$ represents the resultant attachment between the compound of the invention and a biomolecule such as a carrier protein, a peptide or biotin (i.e., $R^{11}$ comprises the linking group joined to a biomolecule).

L is a member selected from the group consisting of a direct link, or a covalent linkage, wherein the covalent linkage is linear or branched, cyclic or heterocyclic, saturated or unsaturated, having 1-60 atoms selected from the group consisting of C, N, P, O, and S, wherein L can have additional hydrogen atoms to fill valences, wherein the linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds. In certain aspects, L comprises a terminal amino, carboxylic acid, or sulfhydryl group.

In certain preferred aspects, L is of the formula:

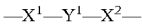

wherein: $X^1$ is a member selected from the group of a bivalent radical, a direct link, oxygen, an optionally substituted nitrogen and sulfur; $Y^1$ is a member selected from the group of a direct link and $C_1$-$C_{10}$ alkylene optionally interrupted by a heteroatom: and $X^2$ is a member selected from the group of a bivalent radical, a direct link, oxygen, an optionally substituted nitrogen and sulfur.

Preferably, the bivalent radical of $X^1$ and $X^2$ are each independently selected from the group of a direct link, optionally substituted alkylene, optionally substituted alkyleneoxycarbonyl, optionally substituted alkylenecarbamoyl, optionally substituted alkylenesulfonyl, arylenesulfonyl, optionally substituted aryleneoxycarbonyl, optionally substituted arylenecarbamoyl, optionally substituted thiocarbonyl, a optionally substituted sulfonyl, and optionally substituted sulfinyl.

In certain preferred aspects, L is —$(CH_2)_n$—, wherein r is an integer from 1 to 10, preferably n is an integer from 1 to 5, such as 1 to 4, or 1, 2, 3, 4, or 5.

In addition, the benzoxazole derivatives can be used to make immunogenic conjugates. For example, in one aspect, the conjugates of the present invention are used to raise an immunogenic response that is specific to the metabolite of interest. In certain instances, a benzoxazole derivative and a linker arm (wherein n is about 1-4) can be used to append a carrier protein such as BSA to an amino (or sulfhydryl) end. To test the affinity and specificity of the antibody thus produced, a biotinylated hapten is made. The present invention provides stable derivatives of serotonin (5-HT), 5-hydroxyindole acetic acid (5-HIAA) and other metabolites in the serotonin pathway. The derivative can be conjugated to a biomolecule such as a carrier protein and combined with an adjuvant to stimulate an immune response. The derivative can also be conjugated to other biomolecules. In certain aspects, one serotonin metabolite derivative for further conjugation has the following structure:

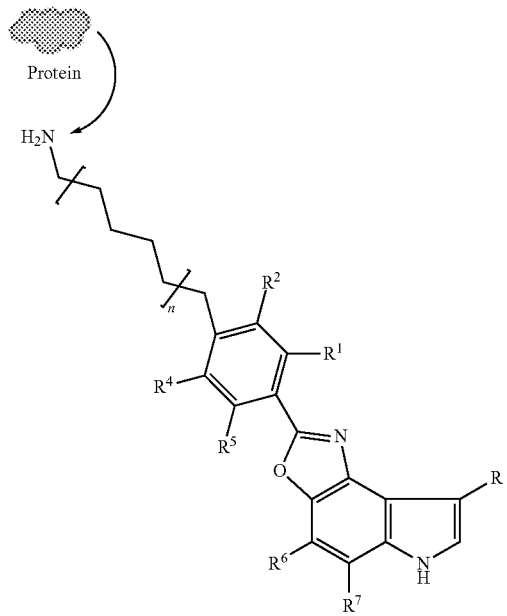

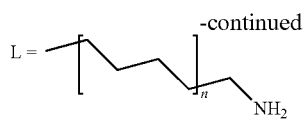

The compound of formula I can be reacted with a carrier molecule using conjugation chemistry well known in the art. For example, an activated ester (an NHS ester) can react with a primary amine to make a stable amide bond. A maleimide and a thiol can react together and make a thio-ether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

When linking a carrier protein having a carboxylic acid group for attachment to an amine containing metabolite, the carboxylic acid can first be converted to a more reactive form using an activating reagent, to form for example, a N-hydroxy succinimide (NHS) ester or a mixed anhydride. The amine-containing metabolite is treated with the resulting activated acid to form an amide linkage. One of skill in the art will recognize that alternatively, the NHS ester can be on the metabolite and the amine can be on the carrier protein.

The process of stabilizing the metabolite by derivatization allows for generation of antibodies to the immunogenic conjugate. With the antibodies in hand, an immunoassay such as ELISA can be used wherein the antibody is highly specific to the metabolite of interest. In other instances, the derivatives include serotonin-O-sulfate and serotonin-O-phosphate, as shown below:

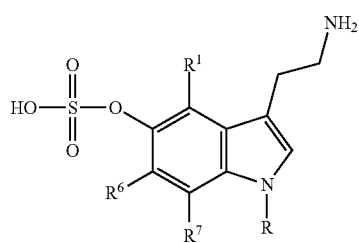

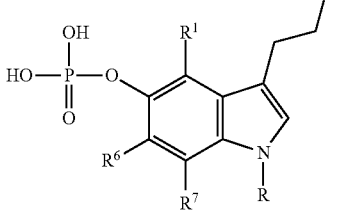

wherein R, $R^1$, $R^6$, and $R^7$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}B$.

As is illustrated in FIG. 1, metabolites of interest in the serotonin pathway are for example, serotonin 101, 5-hydroxyindole acetaldehyde 105 and 5-hydroxyindole acetic acid 115. Thus, in one aspect, the present invention provide an isolated antibody or antigen binding fragment thereof that specifically binds to 5-hydroxytryptamine (5-HT) 101, wherein the antibody has less than 1% cross-reactivity to one or more metabolites such as a member selected from the group consisting of tryptophan 122, 5-hydroxytryptophan 125 and 5-hydroxyindole acetic acid 115. In another aspect, the present invention provide an isolated antibody or antigen binding fragment thereof that specifically binds to 5-hydroxyindole acetic acid 115, wherein the antibody has less than 1% cross-reactivity to one or more metabolites selected from the group consisting of tryptophan 122, 5-hydroxytryptophan 125, and 5-hydroxytryptamine (5-HT) 101.

Figure 2:
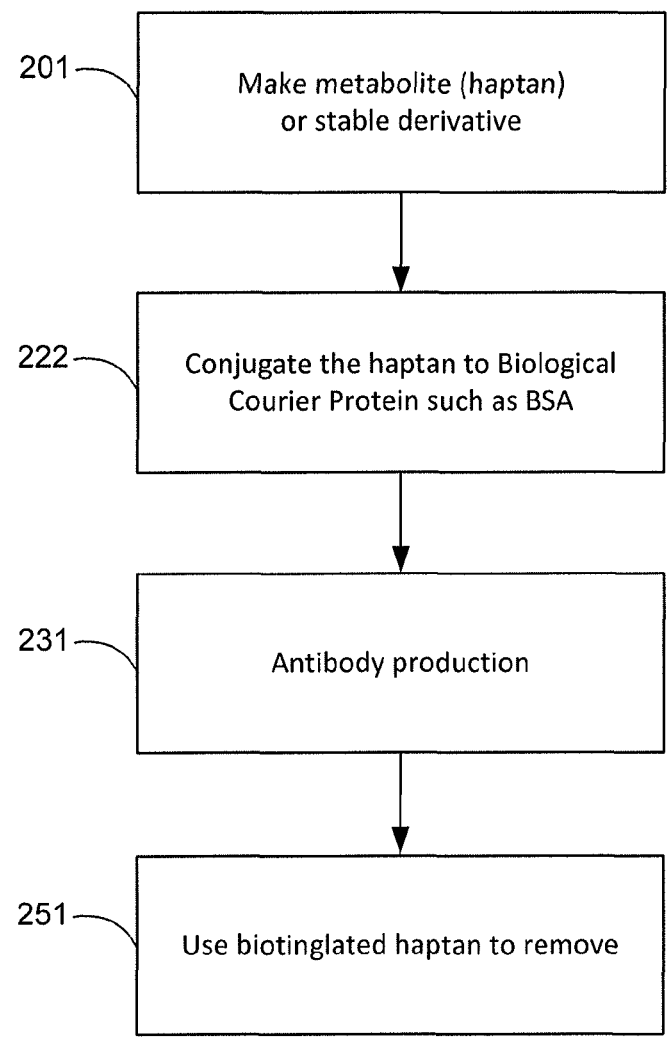
FIG. 2 illustrates a flow diagram of one method of antibody production of the present invention.

Turning now to FIG. 2, in one aspect, the present invention provides antibodies to metabolite conjugates. In step 201, a metabolite or stable derivative thereof is prepared. In step 222, a carrier protein such as bovine serum albumin BSA is conjugated to the derivative. In step 231, antibodies are made by injecting the conjugate into a mammal such as a rabbit, mouse, sheep, chicken, goat and the like. Thereafter, the biotinylated haptan 251 can be used to test the antibody so produced.

In other aspects, the present invention provides methods for making antibodies. The method comprises:
(a) providing an immunogen comprising a derivative selected from the group consisting of serotonin (5-HT), 5-hydroxyindole acetic acid (5-HIAA), and 5-hydroxy tryptophan (5-HTP) each derivative conjugated to a carrier protein;
(b) immunizing an animal with the immunogen under conditions such that the immune system of the animal makes the antibodies; and
(c) removing the antibodies from the animal.

In one aspect, the antibody generated from a mammal can be removed from the serum using the conjugates of the present invention. For example, in one aspect, a compound of Formula Ia, Ib and Ic can be used to remove the antibody from the serum, which conjugates have the following structures:

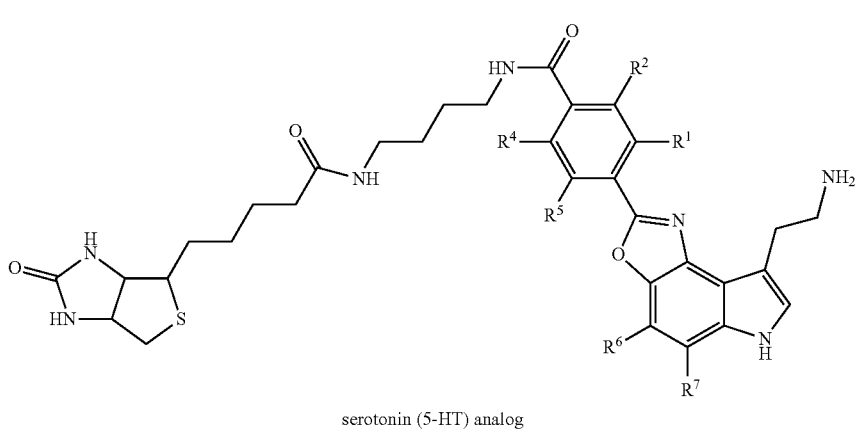

serotonin (5-HT) analog

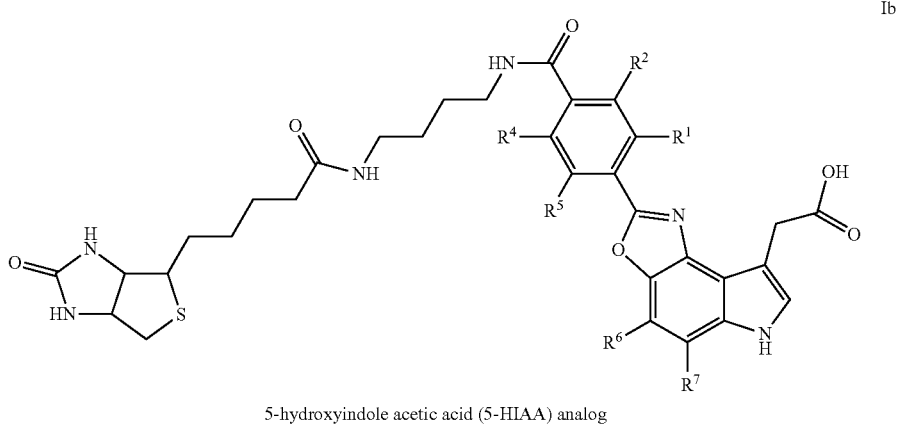

5-hydroxyindole acetic acid (5-HIAA) analog

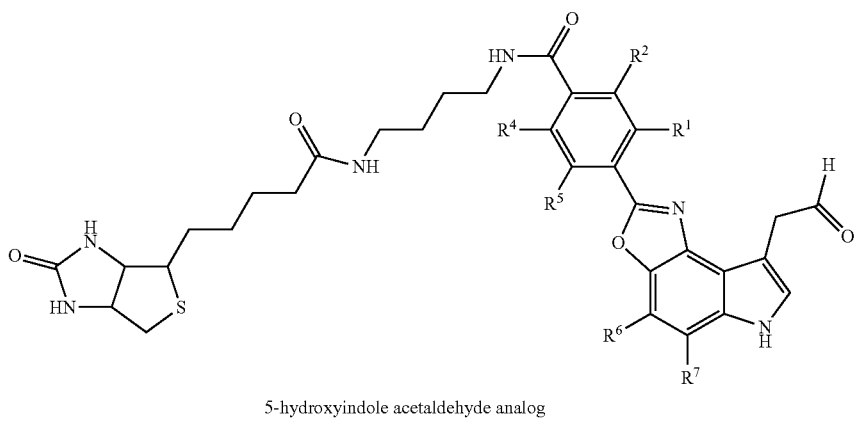

5-hydroxyindole acetaldehyde analog

The biotinylated compound of Formula Ia, Ib or Ic can be used to remove their corresponding antibodies from a mammal (such as a the rabbit, mouse or goat). Thereafter, a secondary antibody is used to detect the antibody conjugate.

In another aspect, the antibodies so produced using the methods described herein can be used to quantitate the amount or level of the metabolite in the pathway of interest by using immunoassays such as an ELISA or CEER.

In one aspect, the present invention provides assay methods wherein an antibody-antigen reaction is carried out. For example, an antigen or metabolite such as 5-HT is allowed to react with a peroxidase-labeled antibody to form an antigen-antibody complex. The thus formed antigen-antibody complex is then allowed to react with a fixed antibody, so that the activity of the peroxidase is measured by chemiluminescence which is generated by the reaction with for example, luminol, serving as a substrate. The presence, concentration and or level of metabolite is thereby measured.

In certain instances, the antibodies of the present invention are used in immunoassays such as an Enzyme Linked Immunosorbent Assay (ELISA), which utilize an enzyme label for the detection of metabolite presence, levels and concentrations. In one aspect, a specific antibody of the present invention is absorbed to a plate. The nonspecific sites are blocked with a protein solution which has no active part in the specific immunochemical reaction of a particular assay. The metabolite of interest is captured by the antibody on the plate. Thereafter, the conjugate can be detected by another antibody with an enzyme label. The enzyme label is reacted with chemiluminescent reagents and detected.

In another ELISA embodiment, the metabolite or a derivative can be immobilized. An antibody of the present invention can be used to bind to the immobilized metabolite. Thereafter, the conjugate can be detected by another antibody with an enzyme label. The enzyme label is then reacted with chemiluminescent reagents and detected.

The assay methods to detect any of the metabolites described herein can comprise any immunoassay known in the art. In some aspects, the assay is performed in a liquid phase. In other embodiments, the assay is performed on a solid phase, e.g., on a bead or a microplate, for example a 96 well microtiter plate. Non-limiting examples of immunoassays useful in these methods are a radioimmunoassay, a microarray assay, a fluorescence polarization immunoassay, an immunoassay comprising FRET, enzyme linked immunosorbent assay (ELISA) or CEER.

Any ELISA known in the art as useful for hapten detection can be utilized for the instant assays. ELISA for haptens generally utilize a competitive format, i.e., where the hapten (a metabolite) in the sample competes with a labeled hapten (e.g., a biotin-hapten or enzyme-hapten conjugate) for antihapten antibody binding sites such that less labeled hapten is bound when there is more hapten in the sample. Thus, in these competitive assays, an increasing amount of hapten in the sample results in less enzyme bound to the solid phase, and consequently less colored signal. In such competitive assays the sample can be added with the labeled hapten to compete directly for antibody binding sites, or the sample and labeled hapten can be added sequentially such that the labeled hapten simply binds where the sample hapten is not bound.

In some embodiments, the ELISA is a direct competitive ELISA, where the hapten is directly bound to the signaling enzyme, or an indirect competitive ELISA, where the enzyme is bound to another molecule, e.g., a second antibody, or streptavidin.

In one embodiment, the antibodies produced herein are bound to a solid phase, either directly or indirectly, the latter being where the solid phase is coated with an anti-antibody (for example goat antibodies that bind to rabbit IgG antibodies (goat anti-rabbit IgG) and the antibodies are bound to the anti-antibody. The anti-antibodies are also known as "second antibodies." In these assays, the sample and a labeled hapten are added to the solid phase to compete with antibody binding sites on the coated solid phase. After washing, the signal is generated, which measures the amount of labeled hapten that is bound to the solid phase.

B. Assays for Tryptophan Pathway Metabolites

In another aspect, the present invention provides antigens for antibody production of metabolites in the tryptophan pathway. In certain instance, irregularities of serotonin function in irritable bowel syndrome (IBS) are due to changes in the metabolism of the serotonin precursor, L-tryptophan 122. Tryptophan 122 is an essential amino acid that serves as a precursor to serotonin, but which can alternatively be metabolized within the kynurenine pathway leading to the production of other neuroactive agents.

The present invention provides antibodies and methods for preparing antibodies to 5-hydroxy tryptophan (5-HTP).

The derivatization of tryptophan metabolites to benzoxazoles (similar to serotonin metabolites) is optional. Metabolites of interest in the tryptophan pathway are for example, 5-hydroxytryptophan (5-HTP) 125 and tryptophan 122. In one aspect, the trypotphan metabolite derivative has the structure of Formula II:

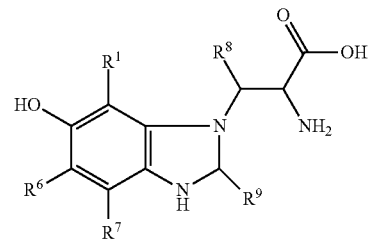

$R^1$, $R^6$, $R^7$, $R^8$, and $R^9$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}B$;

L is a linker;

$R^{11}$ is the resultant attachment between the compound and a biomolecule; and B is a biomolecule.

In another aspect, the compound of Formula II can be used to conjugate a carrier protein using conjugation chemistry well known in the art in order to make antibodies. An activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for one conjugation is as follows:

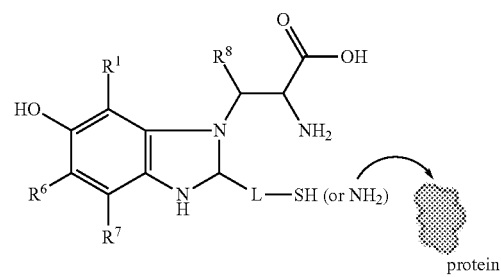

The antibody generated from a mammal can be removed from the serum using the conjugates of the present invention. For example, in one aspect, a compound of Formula II has the structure of Formula IIa:

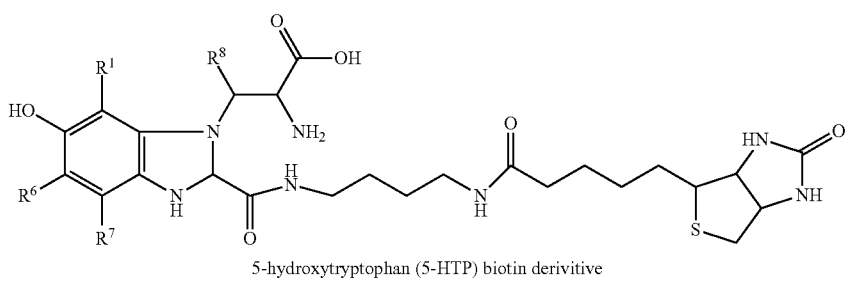

IIa 5-hydroxytryptophan (5-HTP) biotin derivitive

The present invention also provides stable derivatives of 5-hydroxy tryptophan (5-HTP) and methods for making antibodies. The method comprises:
(a) providing an immunogen comprising a derivative of 5-hydroxy tryptophan (5-HTP);
(b) immunizing an animal with the immunogen under conditions such that the immune system of the animal makes the antibodies; and
(c) removing the antibodies from the animal.

In another aspect, the present invention provides an isolated antibody or antigen binding fragment thereof that specifically binds to 5-hydroxytryptophan (5-HTP) 125, wherein the antibody has less than 1% cross-reactivity to one or more members selected from the group consisting of tryptophan 122, 5-hydroxytryptamine (5-HT) 101 and 5-hydroxyindole acetic acid (5-HIAA) 125.

In certain other aspects, the present invention provides a method for assaying for 5-hydroxy tryptophan (5-HTP) in a fluid or tissue sample from a mammal, such as a human. The method comprises combining the sample with the antibodies described herein, and then determining whether the antibodies specifically bind to 5-hydroxy tryptophan (5-HTP) from the sample. For example, in these methods, specific antibody binding to (5-HTP) from the sample indicates that the serotonin (5-HTP) is present in the sample.

In certain instances, the antibodies of the present invention are used in immunoassays such as an Enzyme Linked Immunosorbent Assay (ELISAs) or CEER, which can utilize an enzyme label for the detection of metabolite levels and concentrations.

C. Assays for Kynurenine Pathway Metabolites

In certain instances, kynurenic pathway metabolites play a role in the mechanism of visceral pain and have been linked to low level immune activation in IBS. Only 1% of dietary tryptophan is converted to serotonin and more than 95% is metabolized to kynurenines. Both kynurenine levels and the "kynurenine:tryptophan ratio" are significantly increased in IBS. The kynurenine pathway includes the production of quinolinic acid, an NMDA receptor excitotoxin implicated in neurodegenerative processes. Typically, IBS patients show a decreased concentration of kynurenic acid (N-methyl-D-aspartate (NMDA) receptor antagonist) and an increase in anthranilic acid and 3-hydroxyanthranilic acid (precursors of endogenous NMDA receptor agonist). Tryptophan metabolism along the kynurenine pathway is inhibited in IBS-D. The present invention provides immunoassays assays to determine the levels of tryptophan and kynurenine pathway metabolites, which is of diagnostic importance to determine the status of IBS patients.

The present invention also provides stable derivatives of kynurenine (K), kynurenic acid (KA), 3-hydroxykynurenine (3-HK), 3-hydroxyanthranilic acid (3-HAA), quinolinic acid and anthranilic acid. The derivative can be conjugated to a biomolecule such as a carrier protein and combined with an adjuvant to stimulate an immune response. The derivative can also be conjugated to other biomolecules.

In other aspects, the present invention provides methods for making antibodies. The method comprises:
(a) providing an immunogen comprising a derivative selected from the group consisting of kynurenine (K), kynurenic acid (KA), 3-hydroxykynurenine (3-HK), 3-hydroxyanthranilic acid (3-HAA), quinolinic acid and anthranilic acid each derivative conjugated to a carrier protein;
(b) immunizing an animal with the immunogen under conditions such that the immune system of the animal makes the antibodies; and
(c) removing the antibodies from the animal.

In certain other aspects, the present invention provides a method for assaying for a member selected from the group consisting of kynurenine (K), kynurenic acid (KA), 3-hydroxykynurenine (3-HK), 3-hydroxyanthranilic acid (3-HAA), quinolinic acid and anthranilic acid in a fluid or tissue sample from a mammal, such as a human. The method comprises combining the sample with the antibodies described herein, and then determining whether the antibodies specifically bind to serotonin (5-HT), 5-hydroxyindole acetic acid (5-HIAA), 5-hydroxy tryptophan (5-HTP), kynurenine (K), kynurenic acid (KA), 3-hydroxykynurenine (3-HK), 3-hydroxyanthranilic acid (3-HAA), quinolinic acid and anthranilic acid from the sample. For example, in these methods, specific antibody binding to kynurenine from the sample indicates that kynurenine is present in the sample.

In certain aspects, the immunoassays of the present invention provide reliable and facile ways to monitor metabolites in biological fluids. The present invention provides reliable immunoassays of high specificity and sensitivity for the detection and quantification of kynurenine metabolites.

As shown in FIG. 1, in certain instances, metabolites of the kynurenic pathway include kynurenine 131, kynurenic acid 135, 3-hydroxykynurenine 146, 3-hydroxyanthranilic acid 149, quinolinic acid 160, anthranilic acid 140, and xanthurenic acid 148. The present invention provides antibodies specific for each of these metabolites such that highly specific and sensitive immunoassays are also provided.

Table I shows metabolites of particular interest, a corresponding metabolite analog and a biotinylated analog of the present invention.

| | Metabolite | Analog with linker |
|---|---|---|
| 1 | 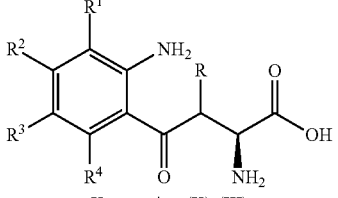<br>Kynurenine (K) (III) | 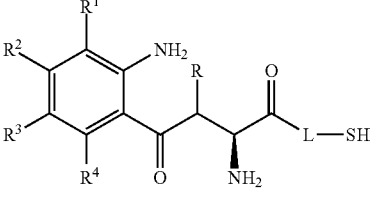 |
| 2 | 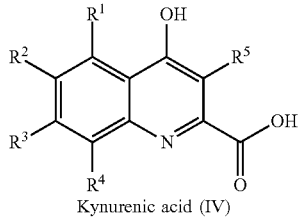<br>Kynurenic acid (IV) | 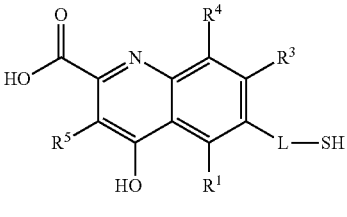 |
| 3 | 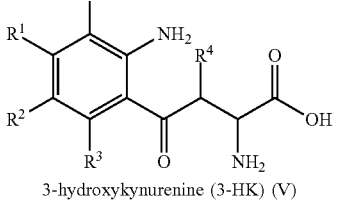<br>3-hydroxykynurenine (3-HK) (V) | 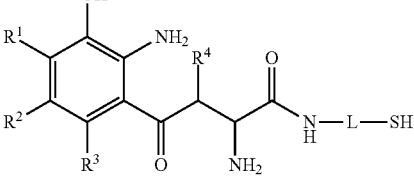 |
| 4 | 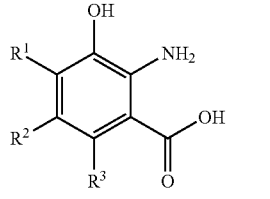<br>3-hydroxyanthranilic acid (3-HAA) (VI) | 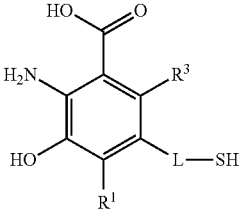 |
| 5 | 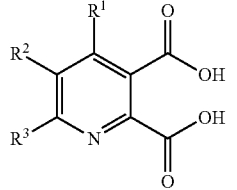<br>Quniolinic acid (VII) | 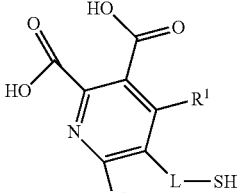 |
| 6 | 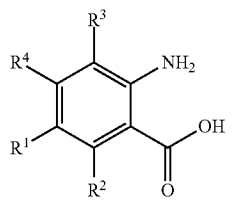<br>Anthranilic acid (AA) (VIII) | 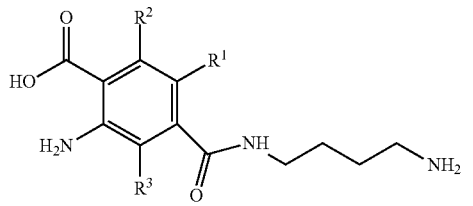 |
| 7 | 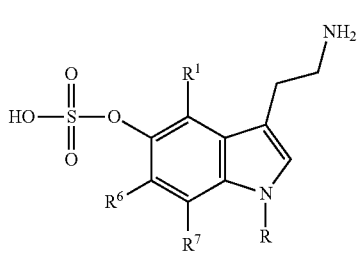 | 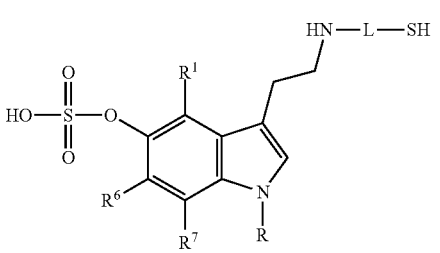 |

| | |
|---|---|
| | serotonin-O-sulfate |
| 8 | 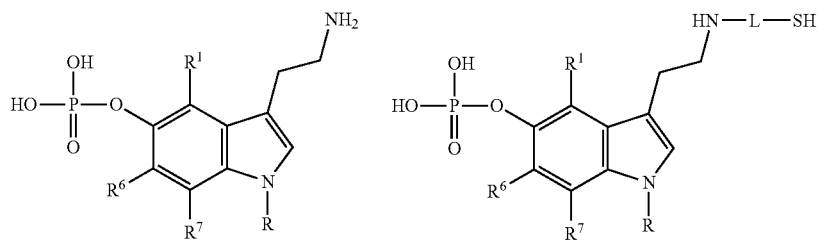 |
| | serotonin-O-phosphate |
| Biotinylated Analog | |
|---|---|
| 1 | 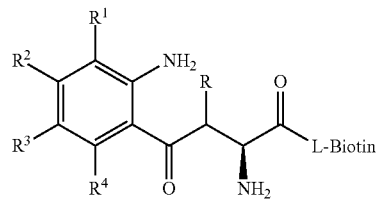 |
| 2 | 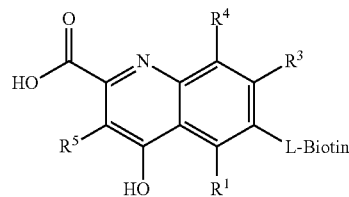 |
| 3 | 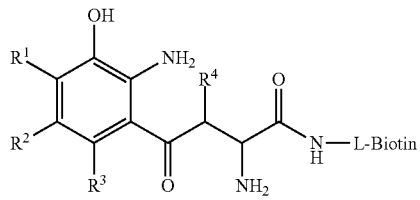 |
| 4 | 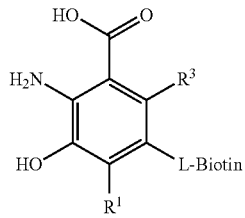 |
| 5 | 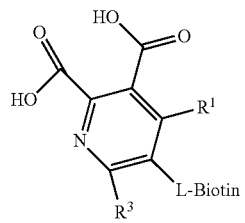 |

6

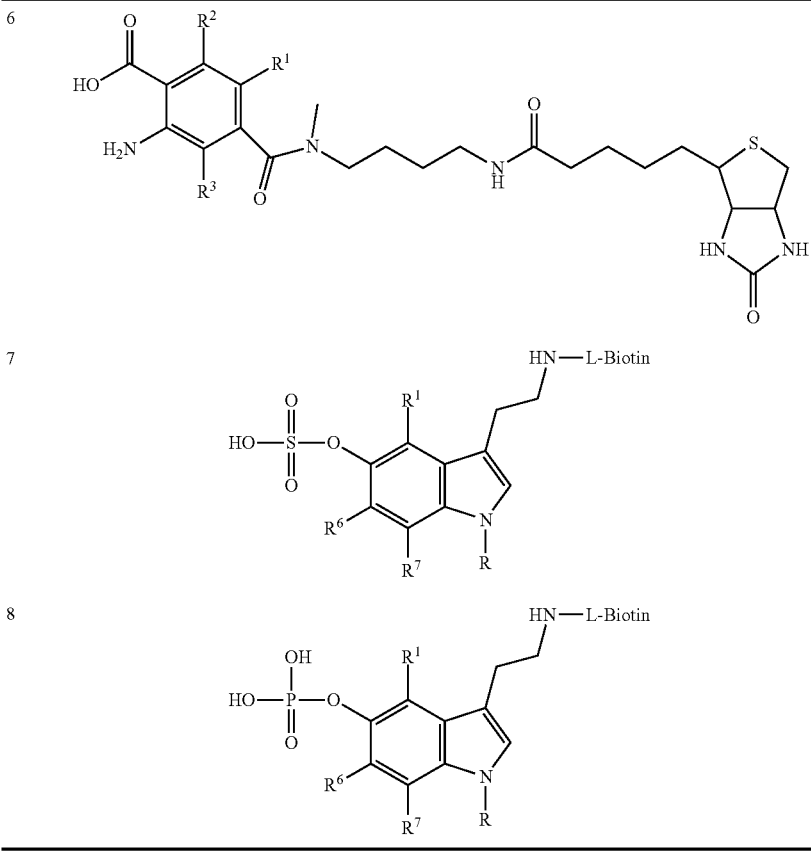

7

8

In the above, L may comprise a terminal amino, carboxylic acid, or sulfhydryl group covalently attached to the ring. In certain instances, the terminal amino, carboxylic acid, or sulfhydryl group is shown and is represented as -L-NH$_2$, or -L-C(O)OH or -L-SH.

In yet another aspect, the present invention provides a compound of Formula III:

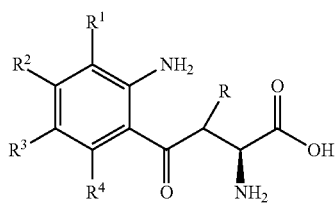

III wherein R, R$^1$, R$^2$, R$^3$, and R$^4$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and R$^{11}$B; L is a linker; and R$^{11}$ is the resultant attachment between the compound and a biomolecule; and B is a biomolecule. The compounds of Formula III are useful in making antibodies specific to kynurenine.

In one aspect, the compound of Formula III, has the structure of formula IIIc, wherein L comprises a terminal SH:

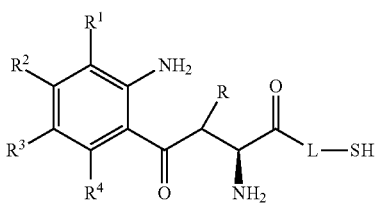

IIIa wherein in certain instances, the thiol group can be used to join a carrier protein, biotin or other biomolecule.

In another aspect, the compound of Formula III can be used to conjugate a carrier protein using conjugation chemistry well known in the art in order to make antibodies. For example, an activated ester (an NHS ester) can react with a primary amine to make a stable amide bond. A maleimide and a thiol can react together to make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

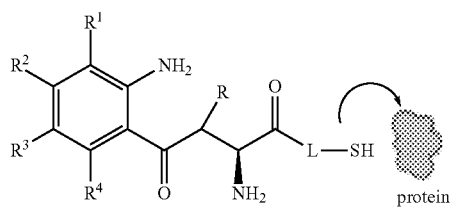

The antibody generated from a mammal can be removed from the serum using the conjugates of the present invention. For example, in one aspect, a compound of Formula III, has the structure of Formula IIIa:

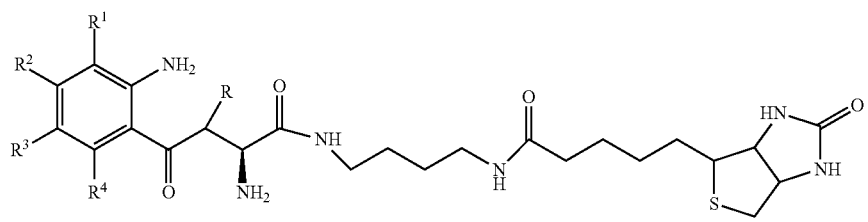

wherein R, $R^1$, $R^2$, $R^3$, and $R^4$ are each hydrogen.

In one aspect, the present invention provides an isolated antibody or antigen binding fragment thereof that specifically binds to kynurenine, and wherein the antibody has less than 1% cross-reactivity to one or more members selected from the group consisting of kynurenic acid 135, 3-hydroxykynurenine 146, 3-hydroxyanthranilic acid 149, quinolinic acid 160, and anthranilic acid 140.

In yet another aspect, the present invention provides a compound of Formula IV:

IV

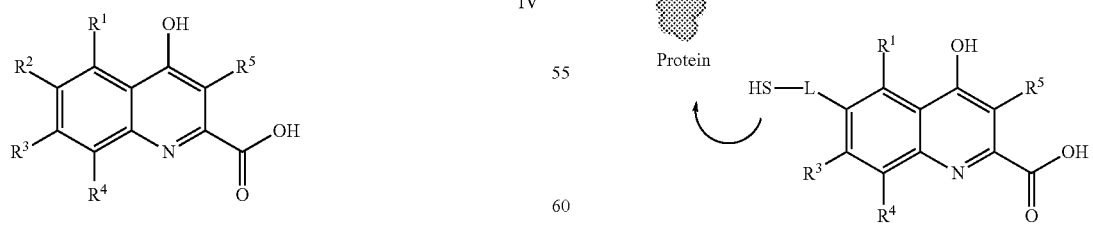

wherein $R^1$, $R^2$, $R^3$, $R^4$ and $R^5$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl L and $R^{11}B$; L is a linker; $R^{11}$ is the resultant attachment between the compound and a biomolecule; and B is a biomolecule. The compounds of Formula IV are useful in making antibodies specific to kynurenic acid 135.

In another aspect, the compound of Formula IV can be used to conjugate a carrier protein using conjugation chemistry well known in the art in order to make antibodies. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

The antibody generated from a mammal can be removed from the serum using the conjugates of the present invention. For example, in one aspect, a compound of Formula IV, has the structure of Formula IVa:

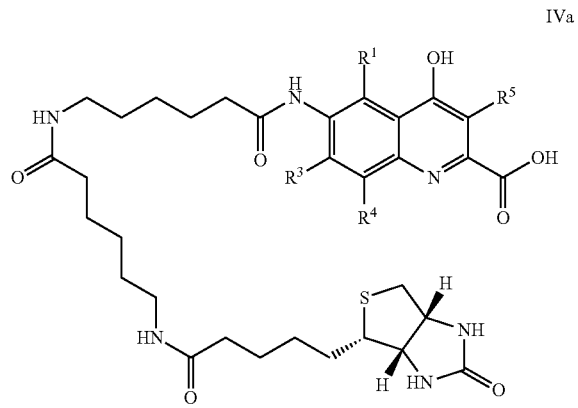

wherein $R^1$, $R^3$, $R^4$, and $R^5$ are each hydrogen.

In another aspect, the present invention provides an isolated antibody or antigen binding fragment thereof that specifically binds to kynureninic acid, and wherein the antibody has less than 1% cross-reactivity to one or more members selected from the group consisting of kynurenine 131, 3-hydroxykynurenine 146, 3-hydroxyanthranilic acid 149, quinolinic acid 160, and anthranilic acid 140.

In yet another aspect, the present invention provides a compound of Formula V:

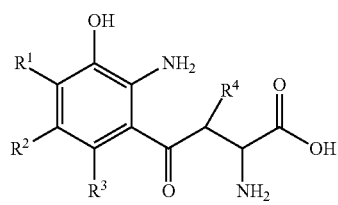

wherein $R^1$, $R^2$, $R^3$, and $R^4$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}$. The compounds of Formula V are useful in preparing antibodies to 3-hydroxykynurenine (3-HK) 146.

In another aspect, the compound of Formula V can be used to conjugate a carrier protein using conjugation chemistry well known in the art in order to make antibodies. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

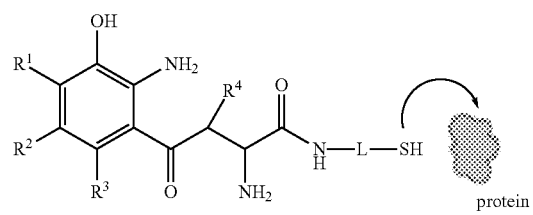

The antibody generated from a mammal can be removed from the serum using the conjugates of the present invention. For example, in one aspect, a compound of Formula V, has the structure of Formula Va:

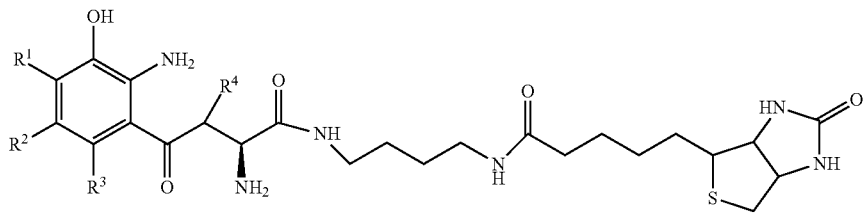

wherein $R^1$, $R^2$, $R^3$, and $R^4$ are each hydrogen.

In still another aspect, the present invention provides an isolated antibody or antigen binding fragment thereof that specifically binds to 3-hydroxykynurenine (3-HK), and wherein the antibody has less than 1% cross-reactivity to one or more members selected from the group consisting of kynurenine 131, kynurenic acid 135, 3-hydroxyanthranilic acid 149, quinolinic acid 160, and anthranilic acid 140.

In yet another aspect, the present invention provides a compound of Formula VI:

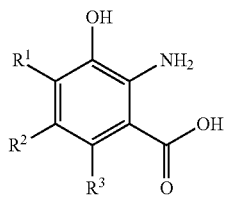

VI wherein $R^1$, $R^2$, and $R^3$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}$; L is a linker; and $R^{11}$ is the resultant attachment between the compound and a biomolecule. Compounds of Formula VI are useful in making antibodies to 3-hydroxyanthranilic acid (3-HAA) 149.

In another aspect, the compound of Formula VI can be used to conjugate a carrier protein using conjugation chemistry well known in the art in order to make antibodies. An activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

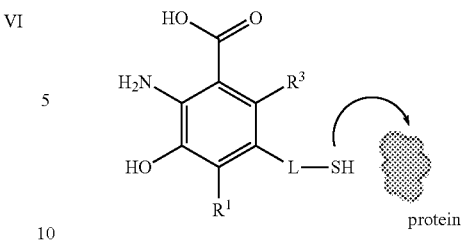

The antibody generated from a mammal can be removed from the serum using the conjugates of the present invention. For example, in one aspect, a compound of Formula VI, has the structure of Formula VIa:

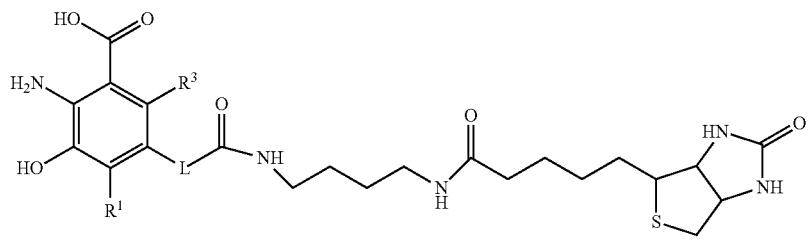

wherein $R^1$ and $R^3$ are each hydrogen.

In yet another aspect, the present invention provides an isolated antibody or antigen binding fragment thereof that specifically binds to 3-hydroxyanthranilic acid, and wherein the antibody has less than 1% cross-reactivity to one or more members selected from the group consisting of kynurenine 131, kynurenic acid 135, 3-hydroxykynurenine 146, quinolinic acid 160, and anthranilic acid 140.

In yet another aspect, the present invention provides a compound of Formula VII:

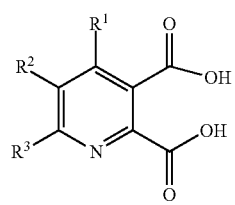

VII wherein $R^1$, $R^2$, and $R^3$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}$B; L is a linker; $R^{11}$ is the resultant attachment between the compound and a biomolecule; and B is a biomolecule. The compounds are useful in making antibodies for quinolinic acid.

In another aspect, the compound of Formula VII can be used to conjugate a carrier protein using conjugation chemistry well known in the art. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

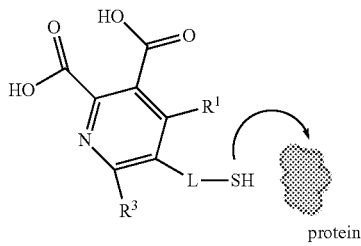

The antibody generated from a mammal can be removed from the serum using the conjugates of the present invention. For example, in one aspect, a compound of Formula VII, has the structure of Formula VIIa:

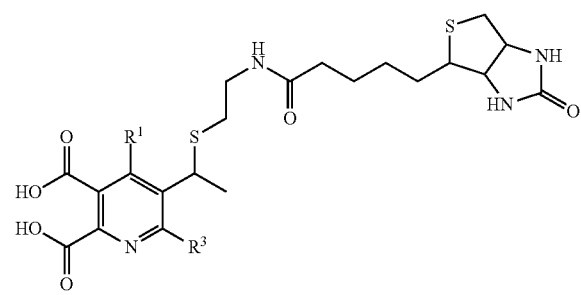

wherein $R^1$, and $R^3$ are each hydrogen.

In one aspect, the present invention provides an isolated antibody or antigen binding fragment thereof that specifically binds to quinolinic acid, and wherein the antibody has less than 1% cross-reactivity to one or more members selected from the group consisting of kynurenine, kynureninic acid 3-hydroxykynurenine, 3-hydroxyanthranilic acid, and anthranilic acid.

In yet another aspect, the present invention provides a compound of Formula VIII:

VIII

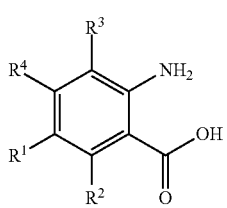

wherein $R^1$, $R^2$, $R^3$, and $R^4$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}B$; L is a linker; $R^{11}$ is the resultant attachment between the compound and a biomolecule; and B is a biomolecule. Compound of Formula VIII are useful in making and producing antibodies to anthranilic acid.

In another aspect, the compound of Formula VIII can be used to conjugate a carrier protein using conjugation chemistry well known in the art. For example, an activated ester (an NHS ester) can react with a primary amine to make a stable amide bond. A maleimide and a thiol can react and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

An exemplary schematic for conjugation is as follows, wherein L comprises a terminal SH:

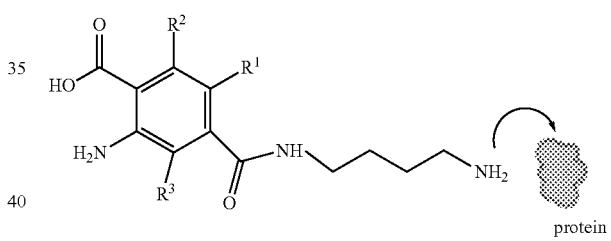

The antibody generated from a mammal can be removed from the serum using the conjugates of the present invention. For example, in one aspect, a compound of Formula VII, has the structure of Formula VIIIa:

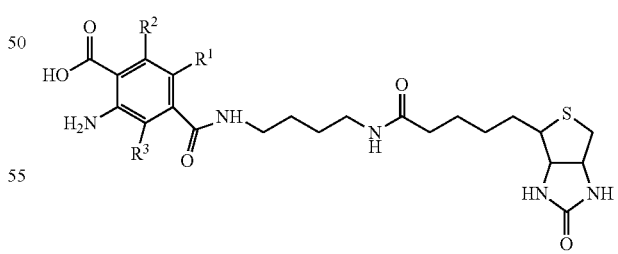

wherein $R^1$, $R^2$, and $R^3$ are each hydrogen.

In still another aspect, the invention provides an isolated antibody or antigen binding fragment thereof that specifically binds to anthranilic acid, and wherein the antibody has less than 1% cross-reactivity to one or more members selected from the group consisting of kynurenine, kynureninic acid 3-hydroxykynurenine, 3-hydroxyanthranilic acid, and quinolinic acid.

In another aspect, the present invention provides antibodies to each of the metabolites in FIG. 1, with less than 1% cross-reactivity to any other metabolite.

In certain other aspects, the present invention provides a method of assaying for a member selected from the group consisting of kynurenine (K), kynurenic acid (KA), 3-hydroxykynurenine (3-HK), 3-hydroxyanthranilic acid (3-HAA), quinolinic acid, anthranilic acid and a combination thereof in a fluid or tissue sample from a mammal, such as a human.

The method comprises combining the sample with the antibodies described herein, and then determining whether the antibodies specifically bind to a member selected from the group consisting kynurenine (K), kynurenic acid (KA), 3-hydroxykynurenine (3-HK), 3-hydroxyanthranilic acid (3-HAA), quinolinic acid, anthranilic acid and a combination thereof from the sample. For example, in these methods, specific antibody binding to 3-HK from the sample indicates that 3-HK is present in the sample.

D. Assays for Short Chain Fatty Acids

In certain aspects, the present invention provides assays for short chain fatty acids (SCFA). For example, the fecal SCFA profile of pediatric patients with IBS-D is characterized by low concentrations of total SCFA, acetate, and propionate and a high concentration and percentage of n-butyrate. Differences in SCFA production by colonic bacterial flora in patients with IBS-D can be related to the development of gastrointestinal symptoms. Studies have shown that combination of *Veillonella* and *Lactobacillus* is known to produce acetic and propionic acid. High levels of acetic and propionic acid may associate with abdominal symptoms and impaired quality of life. (see, Treem W R, *J Pediatr Gastroentrol Nutr.,* 1996 October; 23(3):280-6; Le Gall et al., *J Proteome Res.,* 2011 Sep. 2; 10(9):4208-1; and Tana C., *Neurogastroenterol Motil.,* 2010 May; 22(5):512-9.)

The present invention provides immunoassays such as ELISA and CEER to measure the levels and concentrations of SCFA in order to determine the predisposition or to aid in the diagnosis of IBS.

The present invention provides antibodies and methods of making antibodies to short chain fatty acids. The prepared antibodies have low cross-reactivity to related metabolites; and are useful reagents for specific and sensitive immunoassays for propionic acid and butyric acid.

The present invention also provides stable derivatives of short chain fatty acids (SCFA) such as propionic acid and butyric acid. The derivative can be conjugated to a biomolecule such as a carrier protein and combined with an adjuvant to stimulate an immune response. The derivative can also be conjugated to other biomolecules.

Due to the small molecular size of acetate, propionate and butyrate, a linker can be used to conjugate the SCFA to make an immunogenic hapten. For example, in certain instances, the following linker can be used:

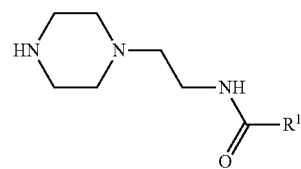

wherein $R^1$ is a short chain alkyl group ($C_2$, $C_3$, $C_4$, $C_5$ or $C_6$).

In another example, the compound has Formula IX:

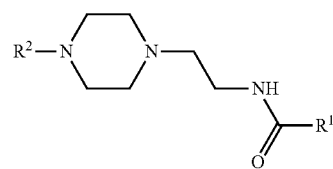

$R^2$ is L or $R^{11}B$; wherein B is a biomolecule.

The antibody generated from a mammal using these compounds can be removed from the serum using the conjugates of the present invention. For example, in one aspect, such a conjugate has the flowing structure:

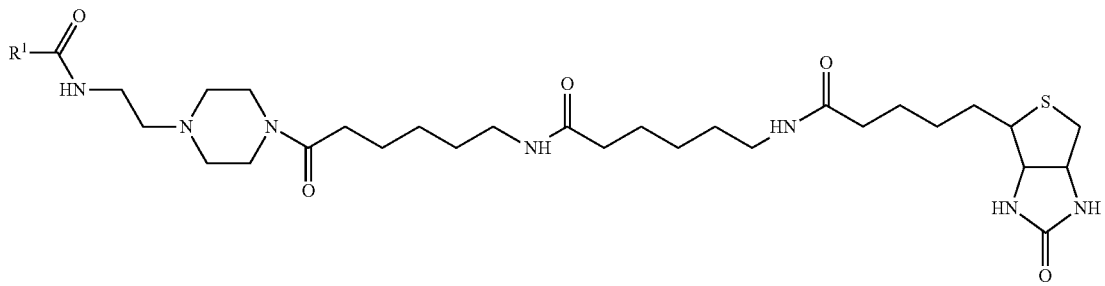

In other aspects, the present invention provides methods for making antibodies of short chain fatty acids. The method comprises:
(a) providing an immunogen comprising a derivative of a short chain fatty acid conjugated to a carrier protein;
(b) immunizing an animal with the immunogen under conditions such that the immune system of the animal makes the antibodies; and
(c) removing the antibodies from the animal.

In one aspect, the present invention provides an isolated antibody or antigen binding fragment thereof that specifically binds to propionic acid, and wherein the antibody has less than 1% cross-reactivity to butyric acid.

In another aspect, the present application provides an isolated antibody or antigen binding fragment thereof that specifically binds to butyric acid, and wherein the antibody has less than 1% cross-reactivity to propionic acid.

In certain other aspects, the present invention provides a method of assaying for a short chain fatty acid in a fluid or tissue sample from a mammal, such as a human. The fluid can be any biological fluid such as blood, urine, plasma, sweat, saliva, aspirate, tears, and the like. The method comprises combining the sample with the antibodies described herein, then determining whether the antibodies specifically bind to a short chain fatty acids from the sample. For example, in these methods, specific antibody binding to propionic acid from the sample indicates that propionic acid is present in the sample.

E. Assays to Measure Bile Acid Malabsorption

Bile acid malabsorption (BAM) can contribute to the development of chronic diarrhea and IBS-D. Serum 7-α-hydroxy-4-cholesten-3-one has been one test to determine bile acid (hepatic) synthesis, which correlates with the activity of cholesterol 7-hydroxylase (which is the rate limiting enzyme) in bile acid synthesis from cholesterol.

The present invention also provides antibodies and methods for preparing antibodies to bile acid metabolites. The prepared antibodies have low cross-reactivity to related metabolites, and are useful reagents for specific and sensitive immunoassays for 7-α-hydroxy-4-cholesten-3-one.

The present invention also provides stable derivatives of 7-α-hydroxy-4-cholesten-3-one. The derivative can be conjugated to a biomolecule such as a carrier protein and combined with an adjuvant to stimulate an immune response. The derivative can also be conjugated to other biomolecules.

The present invention provides synthesis of 7-α-hydroxy-4-cholesten-3-one with a linker and which retains biologically important functional groups. In one aspect, the present invention provides synthesis of a 7-α-hydroxy-4-cholesten-3-one derivative and its biotin analog, as shown below:

example, a free amino group can be conjugated to proteins via glutaraldehyde cross-linking, or via carbodiimide cross-linking to available carboxy moieties on the protein. Also, a hapten with a free sulfhydryl group can be conjugated to proteins via maleimide activation of the protein, e.g., using sulfosuccinimidyl-4-(N-maleimidomethyl)cyclohexane-1-carboxylate (Sulfo-SMCC), then linkage to the sulfhydryl group.

As such, in one aspect, the present invention provides a compound of Formula X:

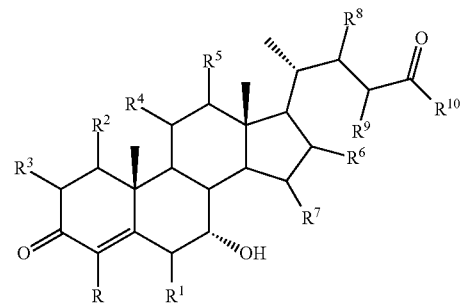

wherein R, $R^1$, $R^2$, $R^3$ $R^4$, $R^5$, $R^6$ $R^7$, $R^8$, $R^9$ and $R^{10}$ are each a member independently selected from the group consisting of hydrogen, alkyl, halo, hydroxyl, alkoxy, amino, aroyl, alkanoyl, amido, substituted amido, cyano,

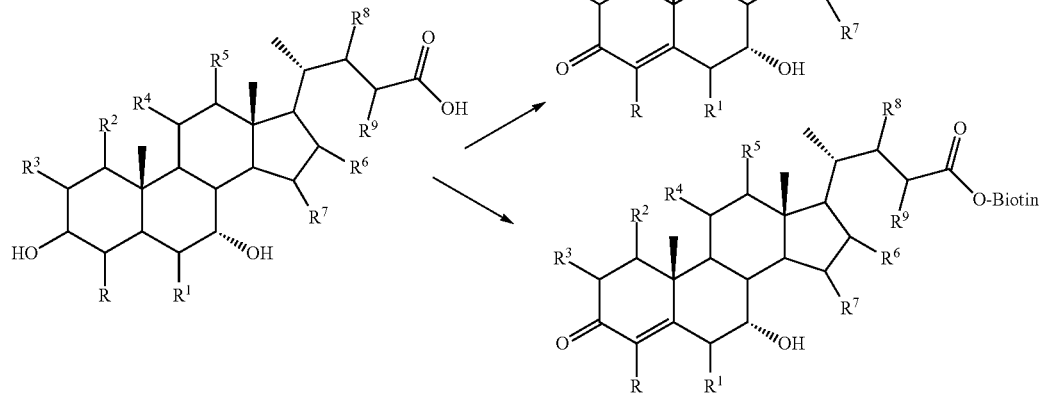

In another aspect, the compound of Formula XI can be used to conjugate a carrier protein using conjugation chemistry well known in the art. For example, an activated ester (an NHS ester) can react with a primary amine to make a stable amide bond. A maleimide and a thiol can react together and make a thioether. Alkyl halides react with amines and thiols to make alkylamines and thioethers, respectively. Any derivative providing a reactive moiety that can be conjugated to a protein can be utilized herein. As is known in the art, moieties comprising a free amino group, a free carboxylic acid group, or a free sulfhydryl group provide useful reactive groups for protein conjugation. For carboxyl, alkoxycarbonyl, sulfonato, alkoxyalkyl, carboxy, carboxyalkyl, alkoxycarbonylalkyl, sulfonatoalkyl, L and $R^{11}B$, L is a linker; $R^{11}$ is the resultant attachment between the compound and a biomolecule; and B is a biomolecule.

In other aspects, the present invention provides methods for making antibodies of 7-α-hydroxy-4-cholesten-3-one. The method comprises:

(a) providing an immunogen comprising a derivative of 7-α-hydroxy-4-cholesten-3-one conjugated to a carrier protein;

(b) immunizing an animal with the immunogen under conditions such that the immune system of the animal makes the antibodies; and (c) removing the antibodies from the animal.

In certain other aspects, the present invention provides a method of assaying for 7-α-hydroxy-4-cholesten-3-one in a fluid or tissue sample from a mammal, such as a human. The method comprises combining the sample with the antibodies described herein, then determining whether the antibodies specifically bind to 7-α-hydroxy-4-cholesten-3-one from the sample. For example, in these methods, specific antibody binding to 7-α-hydroxy-4-cholesten-3-one from the sample indicates that 7-α-hydroxy-4-cholesten-3-one is present in the sample.

The antibody generated from a mammal can be removed from the serum using the conjugates of the present invention. For example, in one aspect, a compound of Formula Xa, has the structure of Formula Xa:

corresponding to the metabolite of interest is injected, for example, into mice or rabbits or another mammal, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engineering: A Practical Approach*, Borrebaeck, Ed., Oxford University Press, Oxford (1995); and Huse et al., *J. Immunol.*, 149:3914-3920 (1992).

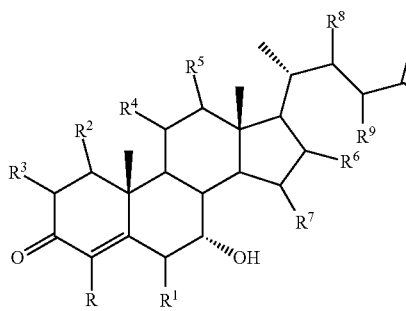

wherein R, $R^1$, $R^2$, $R^3$, $R^4$, $R^5$, $R^6$, $R^7$, $R^8$, $R^9$, and $R^{10}$ are each hydrogen.

In another aspect, the present application provides an isolated antibody or antigen binding fragment thereof that specifically binds to 7-α-hydroxy-4-cholesten-3-one derivative, and wherein the antibody has less than 1% cross-reactivity to a member selected from the group consisting of cholesterol and 7-α-cholesterol.

F. Antibodies

In general, for the generation of antibodies against small molecules (haptens), the hapten is cross-linked with a carrier protein (CP) to make it immunogenic. In certain instances, amine containing neurotransmitters and biogenic amines (i.e., aminated haptens) are linked to a suitable carrier protein (CP) by a one-step linking through glutaric aldehyde and non-amine containing haptens (e.g., 5-HIAA, DOPAC, melatonin, and the like) were conjugated to CP through a Mannich condensation reaction. In certain instances, the hapten is composed of a desired backbone molecular structure linked to a spacer group at a site that is distal to the key molecular features to be recognized by the immune system. The functional group on the other end of the linker, can readily form covalent attachments to the antigenic carrier protein. The linker arm also serves to separate the hapten from the carrier protein at an optimal distance to maximize affinity and specificity for the compound of interest. The chemical bonds formed at both ends of the linker and the length of this spacer arm (three to nine carbon atoms) are critical to the quality in terms of affinity and specificity and quantity (amount of antibody) of the immune response. (Meyer et al., 1991 *J. Histochem. Cytochem.* 39, 749-760: Singh, Suri et al., *Bioconjugate Chem.*, Vol. 15, No. 1, 2004; Ivy Carroll et al., *J. Med. Chem.*, 2011, 54 (14), pp 5221-5228).

III. Production of Antibodies

The generation and selection of antibodies can be accomplished several ways. The synthesized and purified antigen The antibodies that are generated by these methods can then be selected by first screening for affinity and specificity with the purified antigen of interest (such as the biotinylated antigens described herein) and, if required, comparing the results to the affinity and specificity of the antibodies with other antigens that are desired to be excluded from binding. The screening procedure can involve immobilization of the purified antigens in separate wells of microtiter plates. The plates can have streptavidin immobilized thereon and the solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized antigen, such as the biotinylated antigen, is present.

The antibodies so identified can then be further analyzed for affinity and specificity. In the development of immunoassays for a target metabolite, the purified target metabolite acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody can be a more important measure than absolute affinity and specificity of that antibody.

Those skilled in the art will recognize that many approaches can be taken in producing antibodies or binding fragments and screening and selecting for affinity and specificity for the various metabolites of interest, but these approaches do not change the scope of the present invention.

A. Polyclonal Antibodies

Polyclonal antibodies are preferably raised in animals by multiple subcutaneous (sc) or intraperitoneal (ip) injections of an antigen of the present invention and an adjuvant. It may be useful to conjugate the antigen of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R^1N=C=NR$, wherein R and $R^1$ are different alkyl groups.

Animals are immunized against the antigens of the present invention or an immunogenic conjugate or derivative thereof by combining, e.g., 100 μg (for rabbits) or 5 μg (for mice) of the antigen or conjugate with 3 volumes of Freund's complete adjuvant and injecting the solution intradermally at multiple sites. One month later, the animals are boosted with about ⅕ to ⅒ the original amount of conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same antigen, but conjugation to a different immunogenic antigen and/or through a different cross-linking reagent may be used. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature,* 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.,* 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.,* 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.,* 5:256-262 (1993); and Pluckthun, *Immunol Rev.,* 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA,* 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature,* 348:552-554 (1990); Clackson et al., *Nature,* 352:624-628 (1991); and Marks et al., *J. Mol. Biol.,* 222:581-597 (1991). The production of high affinity (nM range) human monoclonal antibodies by chain shuffling is described in Marks et al., *BioTechnology,* 10:779-783 (1992). The use of combinatorial infection and in vivo recombination as a strategy for constructing very large phage libraries is described in Waterhouse et al., *Nuc. Acids Res.,* 21:2265-2266 (1993). Thus, these techniques are viable alternatives to traditional monoclonal antibody hybridoma methods for the generation of monoclonal antibodies.

C. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.*, 24:107-117 (1992); and Brennan et al., *Science*, 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form F(ab')$_2$ fragments (see, e.g., Carter et al., *BioTechnology*, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

D. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see. e.g., Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J Exp. Med.*, 175:217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody"

technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

E. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies that are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalms, affinity ligands, phylomers, aptamers, affibodies, trinectins, and the like.

IV. Methods of Use

The present invention provides a method for determining a diagnosis of Irritable Bowel Syndrome (IBS) in a subject using the presence or concentrations of the metabolites herein. The method comprises measuring one or more metabolites in blood, plasma or serum of the patient by the assay methods described herein.

The present invention also provides a method for determining whether a treatment for IBS in a patient is efficacious. The method comprises measuring one or more metabolites in blood, plasma or serum of the patient by the assay methods described herein.

In certain other aspects, the present invention provides a method for evaluating a patient previously diagnosed with IBS. The method comprises measuring one or more metabolites in blood, plasma or serum of the patient by an assay method described herein.

V. Examples

The following examples are offered to illustrate, but not to limit the claimed invention.

Example 1

Figure 3:
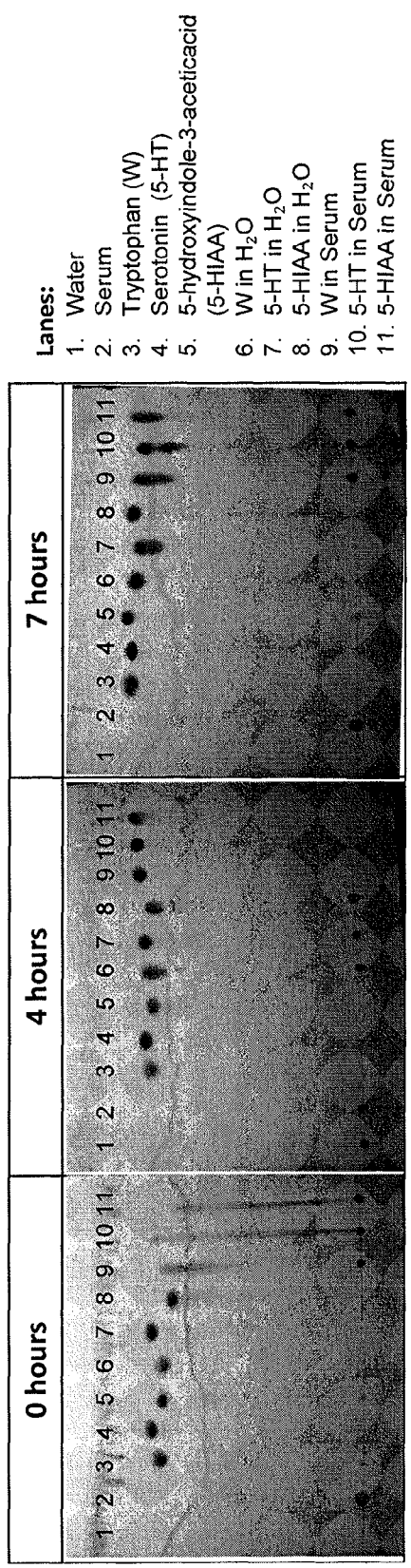
FIG. 3 illustrates a TLC chromatogram, which shows the unstable nature of certain metabolites.
Figure 4:
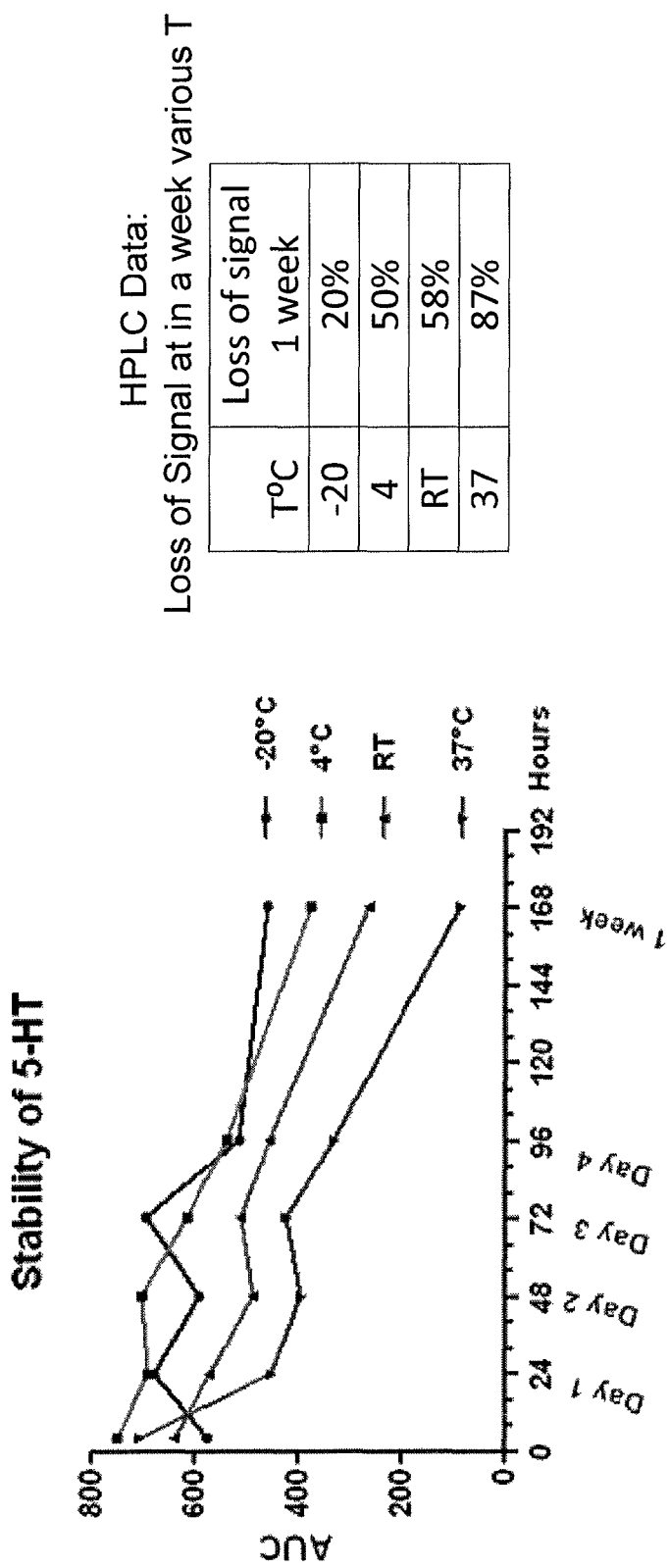
FIG. 4 illustrates the loss of signal of serotonin, which shows the need for a stabilized derivative of the present invention.

A. Serotonin (5-HT) and 5-Hydroxyindole Acetic Acid (5-HIAA) are Sensitive to Oxygen 5-HT and 5-HIAA are sensitive to oxygen and very unstable. Degradation of these compounds occurs at 4° C. in about 7 hours from thawing. FIG. 3 is a thin layer chromatogram (TLC), which shows the degradation of 5-HT and 5-HIAA. The unstable nature of the 5-hydroxyindoles leads to unreliability in assays which measure their concentrations. FIG. 4 shows that 5-HT is unstable during a period of 1 week.

B. Derivatization of Serotonin to Produce a Benzoxazole

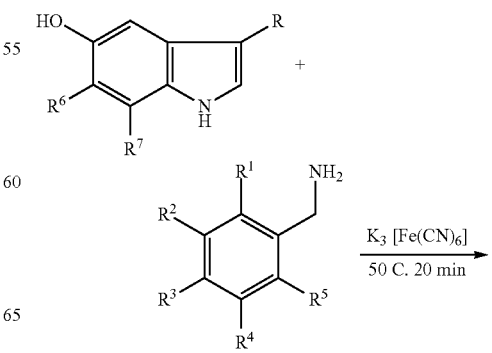

-continued

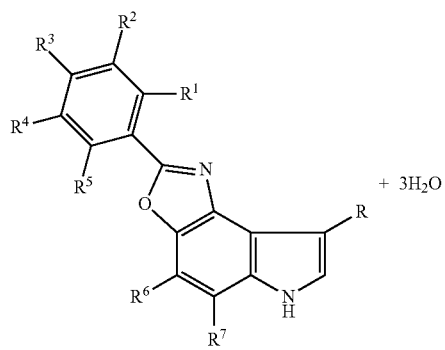

+ 3H₂O

The reactants above were admixed with equal volume of derivatization mix containing 0.1 M CAPS buffer (pH 11.0), 0.1 M p-(aminomethyl) benzyl compound, an oxidizing agent (e.g., 0.05 M potassium hexacyanoferrate (III) or $MnO_2$), and methanol (10/11/22/23, v/v/v/v). The derivatization can be carried out at room temperature (RT) to about 37° C. for about 5 to about 30 min. The fluorescent benzoxazole derivative so produced is stable and can be visualized under UV on TLC plate.

In another aspect, the following conditions can be used: 0.3M CAPS (pH 12), 0.1M p-(aminomethyl) benzyl compound, 50 mM potassium hexacyanoferrate (III) and methanol (1/1/2/2 v/v/v/v). In certain aspects, the v/v/v/v ratio is in a range of 1-10/1-11/2-22/2-23. The derivatization can be carried out at room temperature (RT) to about 37° C. for 5 to about 30 min.

C. Stable Benzoxazole Derivatives are Fluorescent and can be Detected by HPLC.

Figure 5:
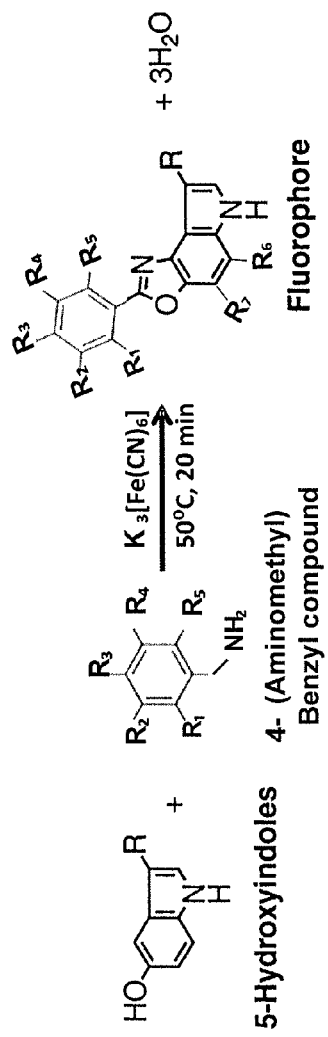
FIG. 5 illustrates a TLC chromatogram, which shows the stable nature of the derivatized metabolites of the present invention, wherein R is —$CH_2CH_2NH_2$ or $CH_2COOH$, $R_1$, $R_2$, $R_3$, $R_4$, $R_5$, $R_6$, $R_7$ is —X(halogen) or —H or alkyl or acid or aryl ester or alkyl ester or sulfonates and any combinations of these groups, and the lanes in TLC (under UV) are 1. p-(aminomethyl)benzyl compound, 2. Tryptophan, 3. Derivatized Tryptophan (W), 4. Serotonin (5-HT, 5-hydroxytryptophan), 5. Derivatized 5-HT, 6. 5-HIAA (5-hydroxyindole-3-acetic acid), 7. Derivatized 5-HIAA.
Figure 5:
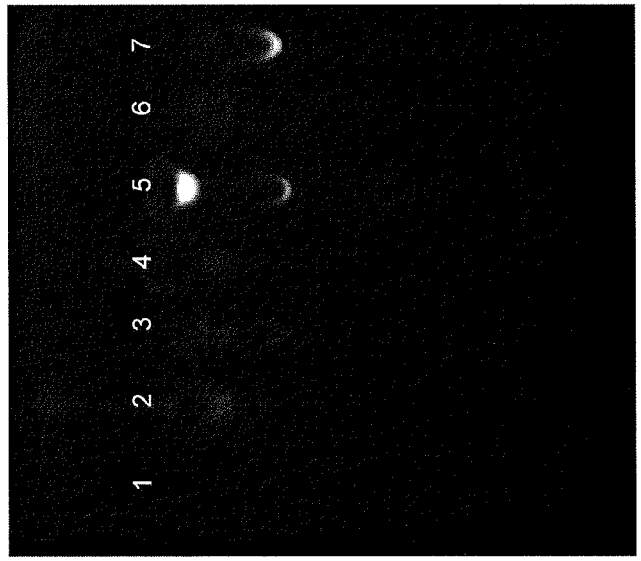
Figure 6:
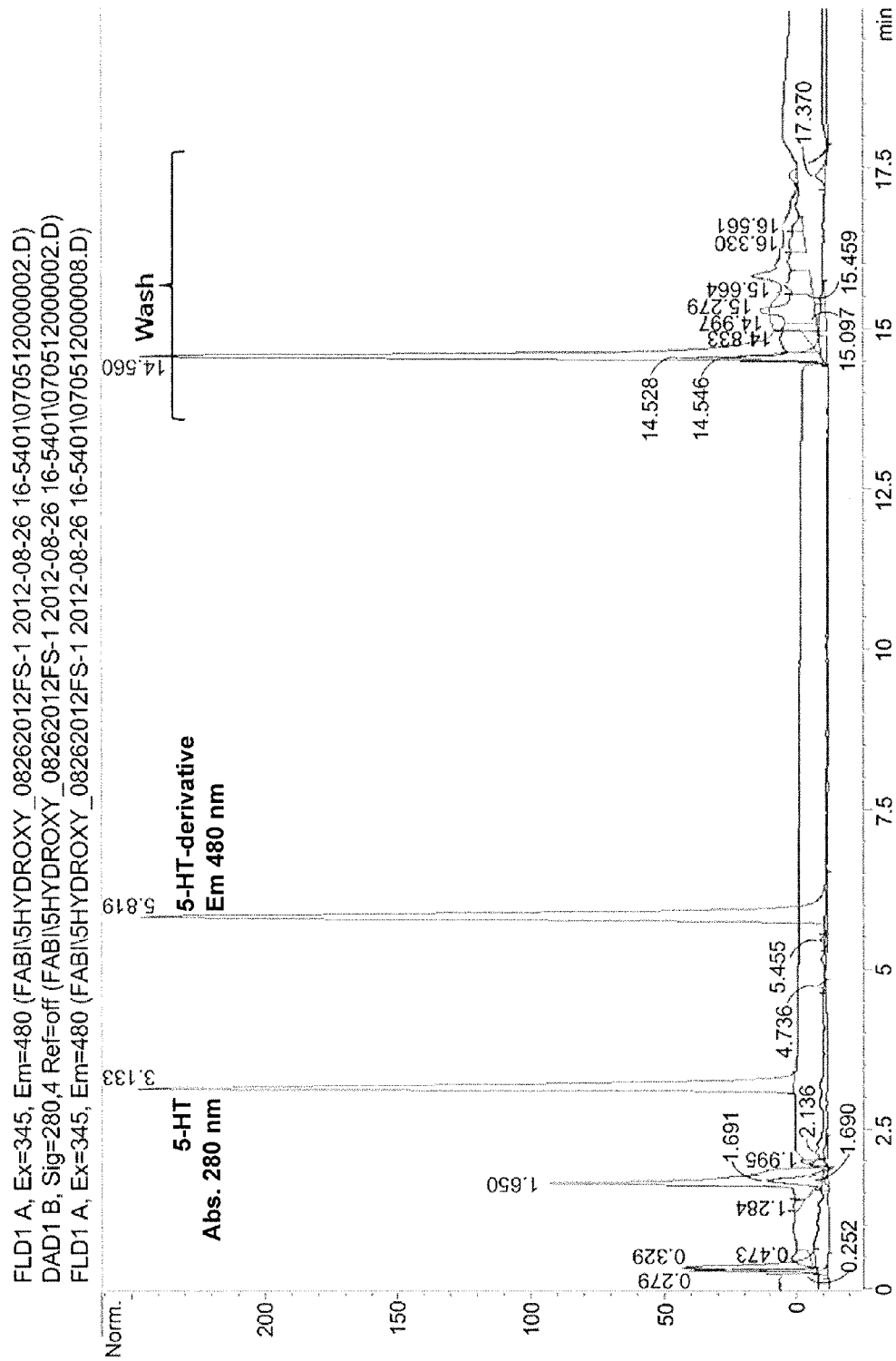
FIG. 6 illustrates a HPLC trace of serotonin and a derivative of the present invention, wherein fluorescent 5-HT benzoxazole derivative of 5-HT shows emission at 480 nm whereas 5-HT does not.

The benzoxazole derivatives are stable, fluorescent and can be visualized under UV on TLC plate (FIG. 5). The stable benzoxazole derivative can be detected by HPLC with high sensitivity. Sample preparation: Incubate 50 μl of serum with 50 μl derivatization mix at a temperature of about 20° C. (room temperature) to about 37° C. for 5-30 min. Deproteinate with acetonitrile (ACN) (1:2 v/v Serum:ACN); Centrifuge at 14,000 rpm for 20 min Filter through 0.2 μm and inject 50 HPLC Method: column: Reverse phase, C18 column: FIG. 6 shows the HPLC chromatogram of the separation of 5-HT.

Figure 7:
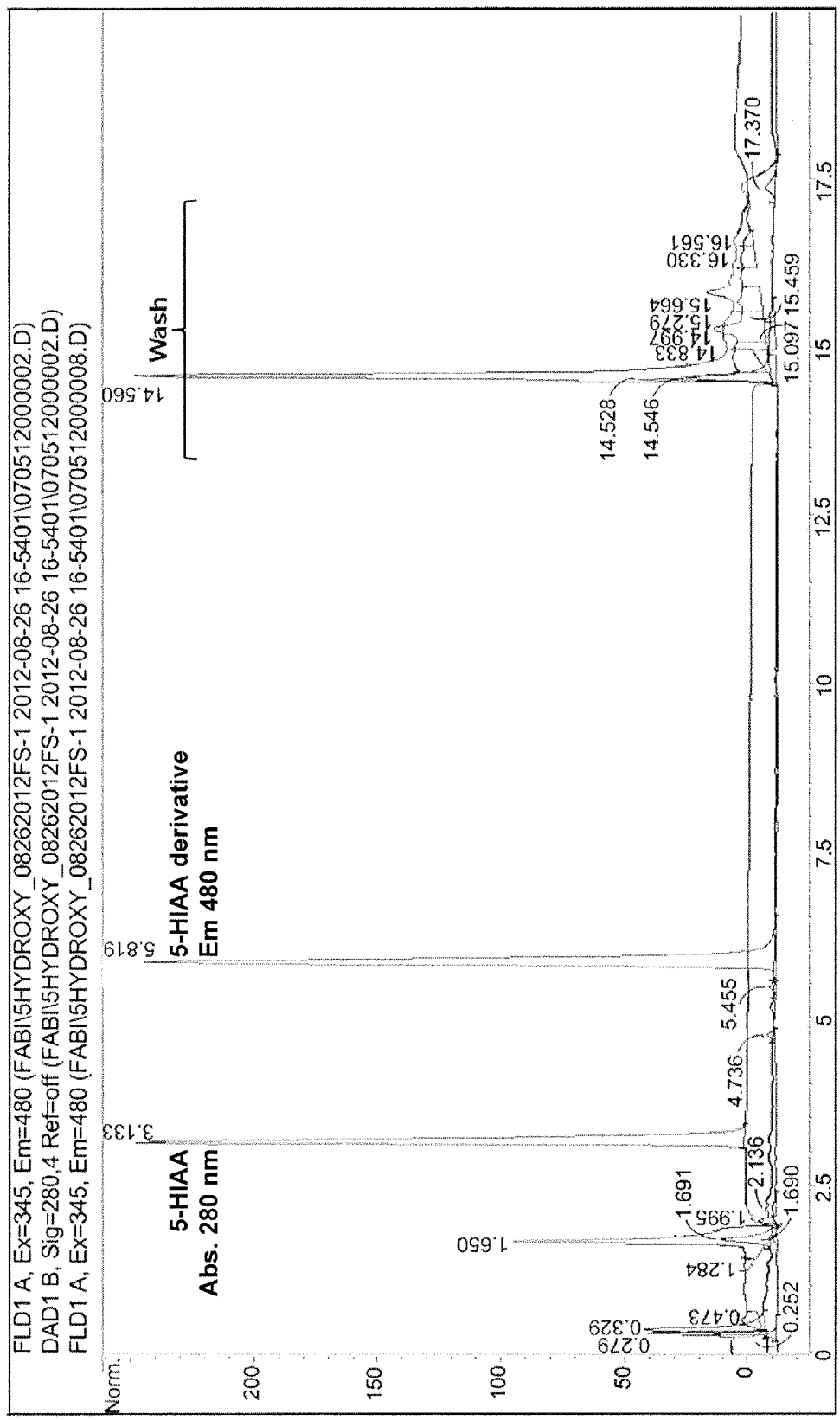
FIG. 7 illustrates a HPLC trace of 5-hydroxyindole acetic acid and a derivative of the present invention, wherein fluorescent 5-HIAA benzoxazole derivative of 5-HIAA shows emission at 480 nm whereas 5-HIAA does not.

FIG. 7 shows the HPLC of 5-HIAA.

Example 2: Synthesis of a Benzoxazole Derivative of 5-HT and its Biotinylated Derivative The scheme below illustrates the synthesis of 16, 17 and 18:

I6: 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide;

I7: 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide compound with N,N-(disulfanediylbis(ethane-2,1-diyl))bis(4-(8-(2-aminoethyl)-6H-oxazolo[4,5-e]indol-2-yl)benzamide) (1:1), I8: 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide.

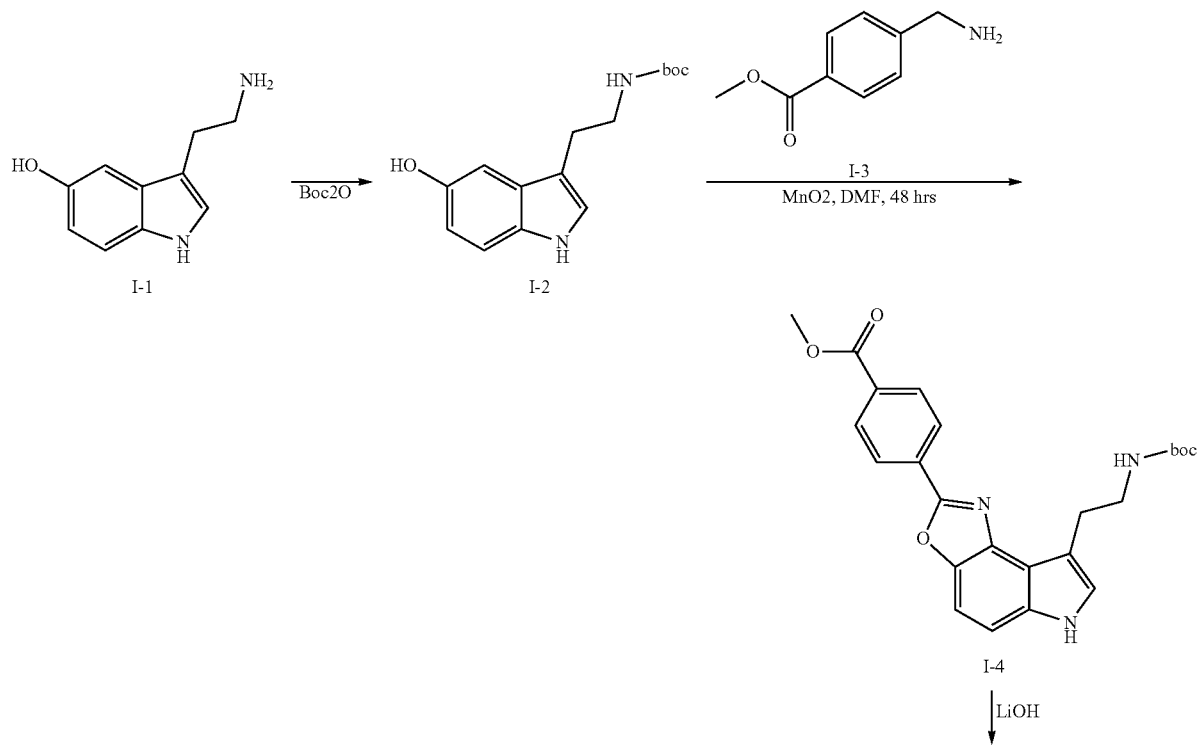

-continued

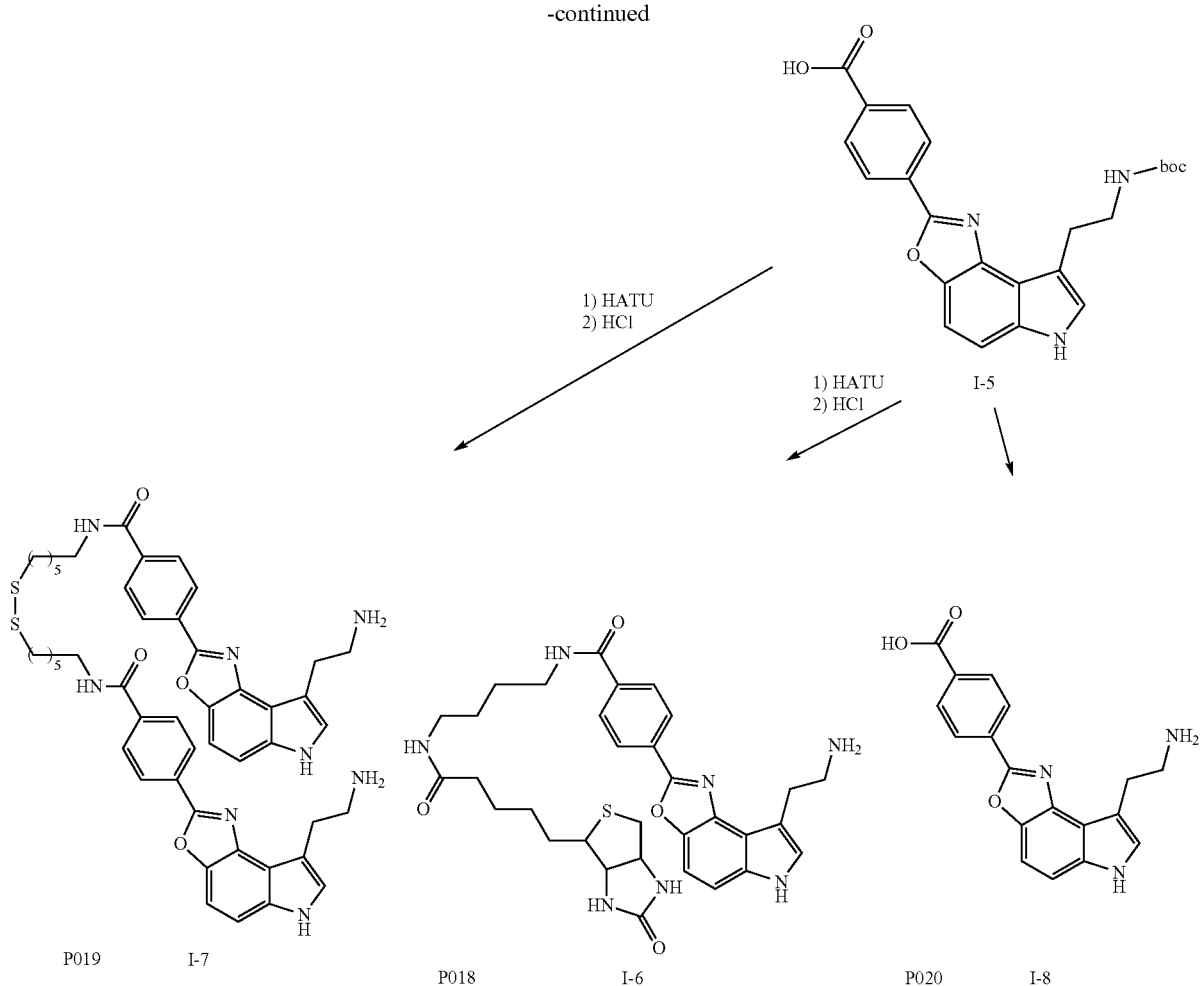

Step 1: to compound I-1 (2.3 g, 10.8 mmol) in MeOH (30 ml) at 0° C. triethylamine (3.3 ml, 23.4 mmol) was added, then Boc$_2$O (3.47 ml, 16.2 mmol) in MeOH were added dropwise. The mixture was warmed to room temperature and stirred for another 2 hrs, then concentrated and purified by silica gel chromatography to give the desired boc product I-2 (2.88) as yellow oil.

Step 2: Compound I-2 (2.36 g, 8.55 mmol) and compound I-3 (2.82 g, 17.1 mmol) were stirred with MnO$_2$ (5.98 g, 68.4 mmol) in DMF (30 ml) for one day. The mixture was filtered and partitioned between water and ethyl acetate. The organic layer was separated and purified to afford I-4 (510 mg) as a yellow solid. MS: 436.0 (M+H)+.

Step 3: I-5 (510 mg, 1.15 mmol) was stirred with LiOH.H$_2$O (0.98 g, 23.4 mmol) in THF (10 ml) and water (4 ml) for one day, acidified by sat. NaHSO$_4$, extracted with ethyl acetate, concentrated to yield a yellow solid (0.5 g).

Step 4: To the compound I-5 (71 mg, 0.17 mmol) in dry DMF (1.5 ml), compound 38 (62 mg, 0.2 mmol), TEA (0.04 ml, 0.26 mmol) and HATU (103 mg, 0.26 mmol) were added. The mixture was stirred for 3 hrs, then partitioned between ethyl acetate and water. The organic layer was then separated and purified. The crude was purified by silica gel column chromatography eluted with DCM/MeOH (90/10) to give the desired product (35 mg) which was treated with 6N HCl in MeOH (2 ml) for 4 hrs and then concentrated to yield the desired compound I-6 (30 mg). MS: 618.0 (M+H)$^+$, 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide.

Step 5: To the compound I-5 (100 mg, 0.23 mmol) in dry DMF (2 ml), compound 32 (53 mg, 0.16 mmol), TEA (0.11 ml, 0.8 mmol) and HATU (180 mg, 0.48 mmol) were added. The mixture was stirred at for overnight, then partitioned between ethyl acetate and water. Organic layer was then separated and concentrated. The crude was purified by silica gel column chromatography eluted with DCM/ethyl acetate (10/1) to give the desired product (30 mg) which was treated with 4N HCl in dioxane (2 ml) overnight and then concentrated to yield the desired compound I-7 (12.4 mg). MS: 872.2 (M+H)$^+$, 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide compound with N,N'-(disulfanediylbis(ethane-2,1-diyl))bis(4-(8-(2-aminoethyl)-6H-oxazolo[4,5-e]indol-2-yl)benzamide) (1:1).

Step 6: I-5 (50 mg, 0.12 mmol) was stirred with 4N HCl in dioxane (2 ml) and DCM (2 ml) overnight, then concentrated to yield the desired product I-8 (26 mg). MS: 322.0 (M+H)+, 4-(8-(2-aminoethyl)-6H-oxazolo[4,5-e]indol-2-yl)-N-(4-(5-(2-oxohexahydro-1H-thieno[3,4-d]imidazol-4-yl)pentanamido)butyl)benzamide.

Example 3: Synthesis of Kynurentic Acid with Linker and Biotinylated

Compound 24: 6-(6-aminohexanamido)-4-hydroxy-quinoline-2-carboxylic acid

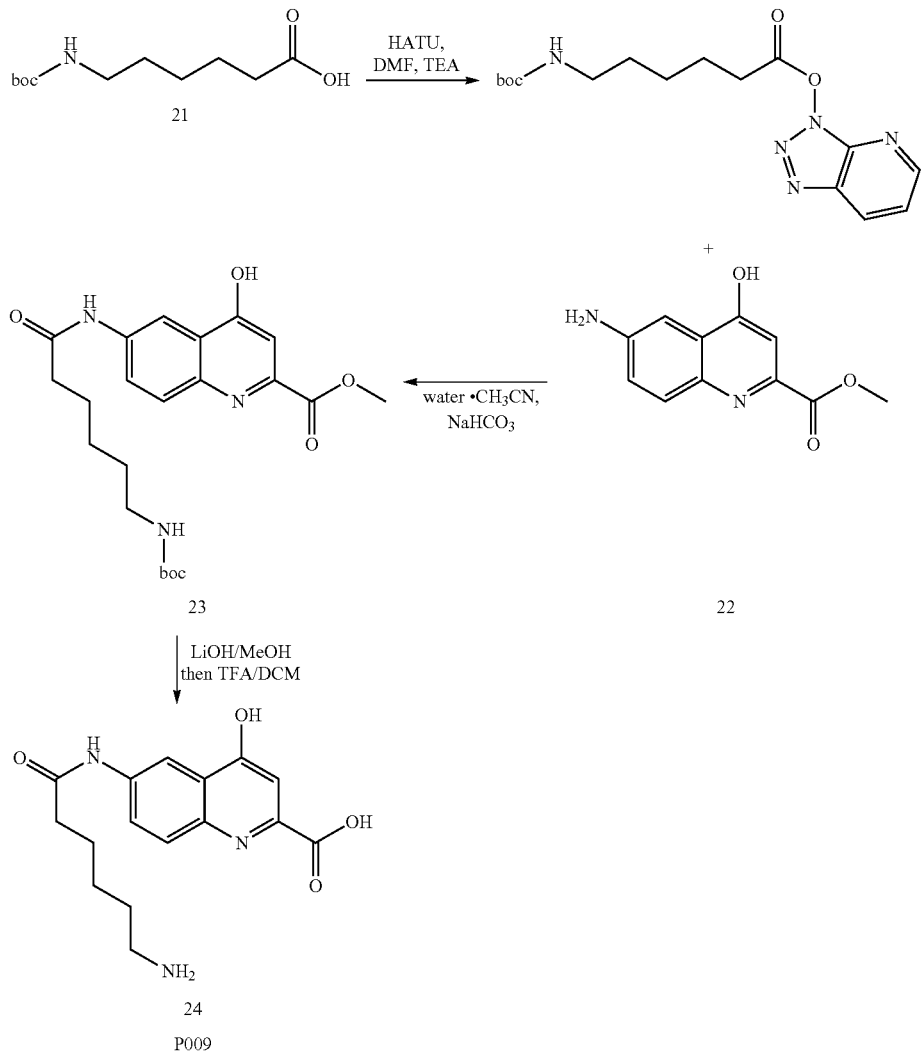

Step 1: A mixture of boc-amino-hexanoic acid (21, 277 mg, 1.2 mmol), DIPEA (0.21 ml, 1.2 mmol) and HATU (456 mg, 1.2 mmmol) were stirred in DCM (5 ml) and acetonitrile (5 ml) for 30 min.

Step 2: To compound 22 (218 mg, 1 mmol) in a mixture of water (5 ml) and acetontrile (5 ml), NaHCO$_3$ (840 mg, 10 mmol) was added, followed by addition of reaction mixture from step 1 slowly with vigorously stirring. The mixture was stirred for additional 4 hrs afterwards, then acidified by sat. NaHSO$_4$, which resulted in precipitation. The solid was filtered to give rise to the intermediate 23.

Step 3: The solid 23 from step 2 was stirred with LiOH.H$_2$O (410 mg, 10 mmol) in MeOH (10 ml) at 60° C. for 4 hrs, then acidified to pH 3 by sat NaHSO$_4$ solution, concentrated. The resulting solid was filtered, washed with water, dried. It was then suspended in DCM (2 ml), followed by addition of TFA (2 ml). The slurry was stirred at room temperature for 4 hrs and then concentrated. Resulting solid was stirred with ethyl acetate (30 ml) for 5 min, insoluble was filtered and washed with ethyl acetate and dried to yield a grey solid as the desired product 24 (120 mg). MS: 318.0 (M+H)$^+$ 6-(6-aminohexanamido)-4-hydroxyquinoline-2-carboxylic acid.

Synthesis of Compound 27: 4-hydroxy-6-(6-(6-(5-((3aS,4S,6aR)-2-oxohexahydro-1H-thieno[3,4-d]imidazol-4-yl)pentanamido)hexanamido)hexanamido)quinoline-2-carboxylic acid

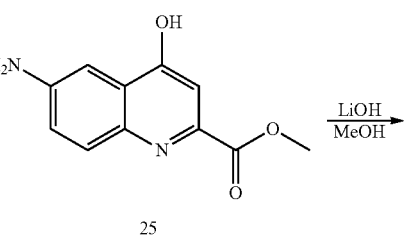

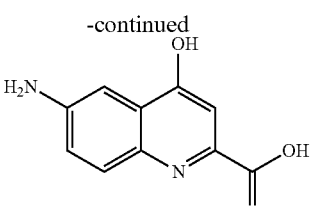

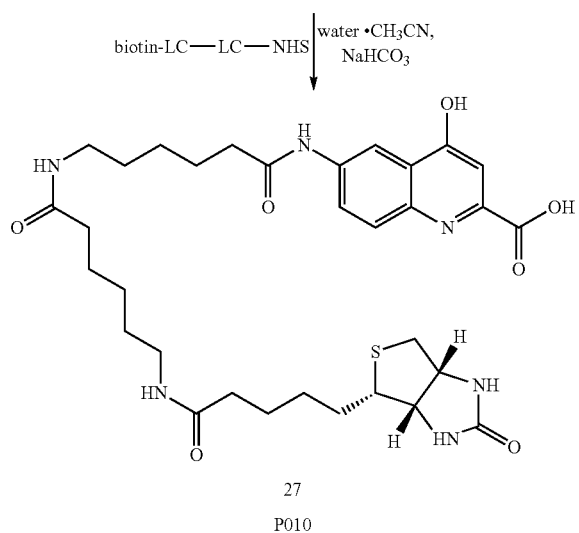

A mixture of compound 25 (327 mg, 1.5 mmol) and LiOH.H₂O (430 mg, 10 mmol) were stirred in MeOH (10 ml) overnight, then carefully acidified 6N HCl to pH 7, concentrated to remove MeOH. The crude was then diluted with acetonitrile and water (10 ml/10 ml), and NaHCO₃ (1.26 g) was added, followed by addition of Biotin-LC-LC-NHS (852 mg, 1.5 mmol). The mixture was stirred vigorously for 1 day, acidified by 6N HCl, the resulting solids were filtered, and washed with MeOH, followed by water, then dried to produce the pure compound 27 (140 mg). MS: 657.2 (M+H)⁺, 4-hydroxy-6-(6-(6-(5-((3aS,4S,6aR)-2-oxo-hexahydro-1H-thieno[3,4-d]imidazol-4-yl)pentanamido)hexanamido)hexanamido)quinoline-2-carboxylic acid.

Example 4: Synthesis of Quinolinic acid with Linker and Biotinylated

Synthesis of Py-6: 5-(1-((2-aminoethyl)thio)ethyl)pyridine-2,3-dicarboxylic acid; and Py7: 5-(1-((2-(5-(2-oxohexahydro-1H-thieno[3,4-d]imidazol-4-yl)pentanamido)ethyl)thio)ethyl)pyridine-2,3-dicarboxylic acid

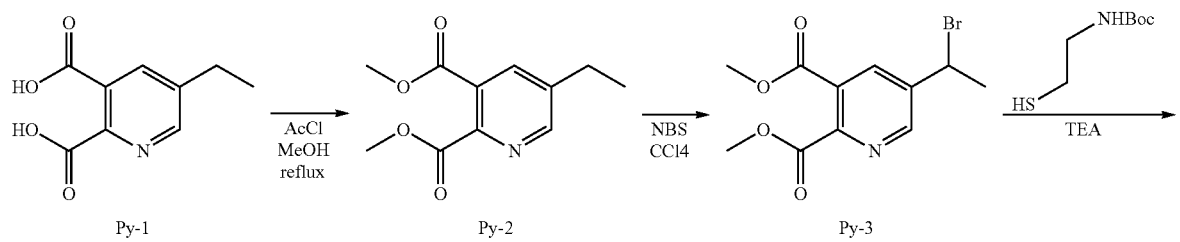

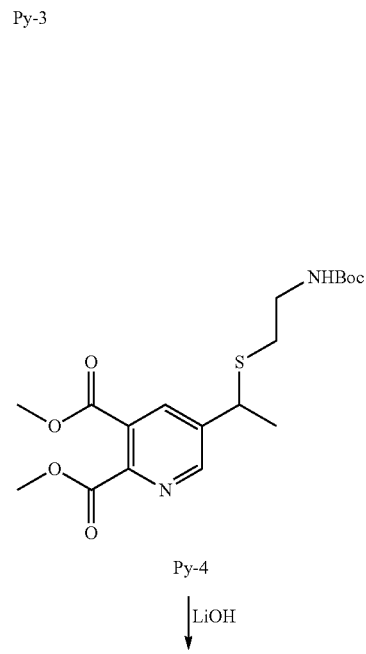

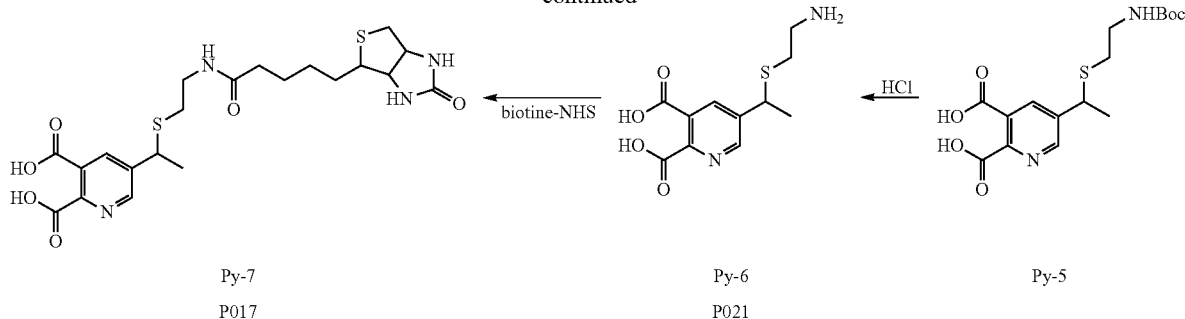

Py-7
P017

Py-6
P021

Py-5

Step 1: to py-1 (5.0 g, 25.6 mmol) in MeOH (100 ml), AcCl (20 ml, 230 mmol) was added cautiously over 30 min. The mixture was then refluxed overnight, then concentrated and redissolved in MeOH (100 ml) and AcCl (20 ml) was added. The mixture was refluxed again for a day and concentrated and partitioned in water and ethyl acetate. The organic layer was washed with sat. NaHCO$_3$, dried and concentrated to yield the dimethyl ester py-2 (3.1 g).

Step 2: py-2 (3 g, 13.4 mmol) was refluxed in CCl$_4$ (50 ml) with NBS (2.4 g, 13.5 mmol) in the presence of AIBN (100 mg) for 8 hrs. The solid was filtered and the solution was concentrated to yield yellowish oil (py-3). MS: 301.9 (M+H)$^+$. The material was used for next step without further purification.

Step 3: to the above oil in DCM (30 ml). BocNHCH$_2$CH$_2$SH (2.74 g, 15 mmol) was added along with addition of triethylamine (2.1 ml, 15 mmol) and DBU (2.28 g, 15 mmol). The mixture was stirred at room temperature overnight and partitioned between water and ethyl acetate. The organic layer was isolated and purified by column chromatography with a mixed solvents of hexane and ethyl acetate to give the desired compound py-4 (2.9 g). MS: 399.0 (M+H)+.

Step 4: a mixture of py-4 (2.1 g, 5.3 mmol) was stirred with LiOH.H$_2$O (2.22 g, 10 eq.) in MeOH (20 ml) for one day, acidified to pH 3 by sat NaHSO$_4$, extracted with ethyl acetate. The organic layer was separated, concentrated to yield the desired product (py-5, 1.7 g). MS: 371.1 (M+H)$^+$.

Step 5: py-5 (0.5 g, 1.35 mmol) was stirred with HCl in dioxane (4N, 10 ml) for 2 hrs, concentrated to form an oil (HCl salt) as py-6. MS: 271.0 (M+H)+, 5-(1-((2-aminoethyl)thio)ethyl)pyridine-2,3-dicarboxylic acid.

Step 6: to py-6 in HCl salt form (200 mg, 0.88 mmol) in MeOH (3 ml), DIPEA (1 ml, 5.5 mmol) was added, followed by addition of Biotin-NHS (341 mg, 1.0 mmol). The mixture was stirred at room temperature for 12 hrs, then concentrated and purified by HPLC to yield the desired product py-7 (85 mg). MS: 497.1 (M+H)+, 5-(1-((2-(5-(2-oxohexahydro-1H-thieno[3,4-d]imidazol-4-yl)pentanamido)ethyl)thio)ethyl)pyridine-2,3-dicarboxylic acid.

Example 5: Synthesis of Anthranilic Acid with Linker and Biotinylated Derivative Synthesis of Compound 30:
2-amino-4-((4-aminobutyl)carbamoyl)benzoic acid; and Compound 31: 2-amino-4-((4-(5-((3aS,4S,6aR)-2-oxohexahydro-1H-thieno[3,4-d]imidazol-4-yl)pentanamido)butyl)carbamoyl)benzoic acid

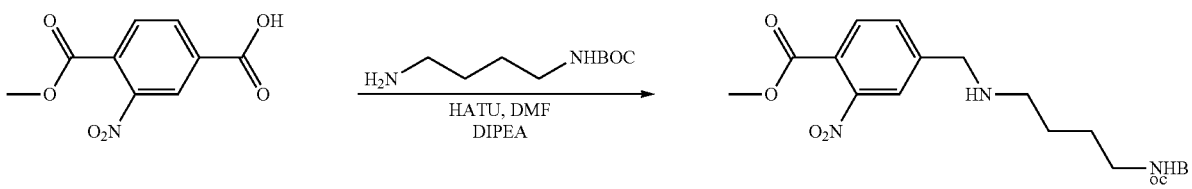

28

29

1) LiOH, THF, H$_2$O
2) NH$_4$HCO$_2$ •Pd/C
3) TFA

-continued

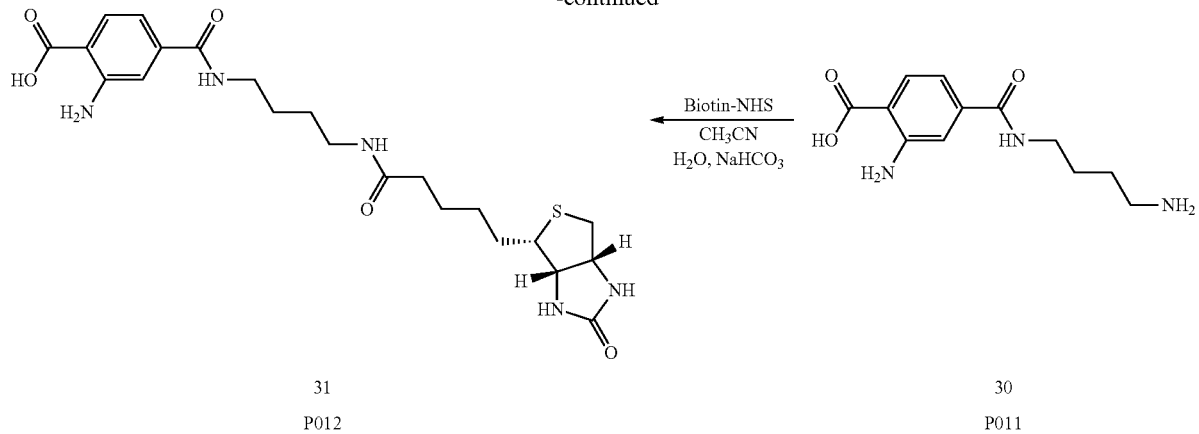

Step 1: a mixture of Boc-4-aminobutylamine (564 mg, 3 mmol), compound 28 (675 mg, 3 mmol), DIPEA (0.8 ml, 4.5 mmol), HATU (1.52 g, 4 mmol) in dry DMF (12 ml) were stirred at room temperature for 12 hrs. It was then partitioned between water and ethyl acetate. The organic layer was isolated, washed with sat NaHSO$_4$, and 6 N NaOH, then concentrated to give compound 29 as an oil.

Step 2: The oil was stirred with LiOH.H$_2$O (1.4 g, 30 mmol) in a mixture of THF (20 ml) and water (0.5 ml) for 2 days, acidified by sat NaHSO$_4$, extracted with ethyl acetate, concentrated and used for the next step without further purification.

Step 3: the material from step 2 were dissolved in ethanol (30 ml), and Pd/C (200 mg) and NH$_4$HCO$_3$ (3.78 g, 60 mmol) were added. The slurry was stirred under reflux for 3 hrs, then filtered, concentrated to yield an solid. The byproduct was further precipitated from DCM/MeOH and filtered away, the mother liquor was concentrated to yield a yellow solid.

Step 4: the yellow solid from step 3 was stirred with 50% TFA in DCM (10 ml) for 2 hrs. It was concentrated and purified by HPLC to yield the desired product 30 (500 mg) as a yellow powders. MS: 252.0 (M+H)+, 2-amino-4-((4-aminobutyl)carbamoyl)benzoic acid.

Step 5: to compound 30 (250 mg, 0.68 mmol) in 50% of acetonitrile in water (4 ml), NaHCO$_3$ (172 mg, 1.5 eq) was added, followed by addition of biotin-NHS (232 mg, 0.68 mmol). The mixture was stirred at room temperature overnight, then acidified by 4N HCl, concentrated, and purified by HPLC to yield the desired product 31 (158 mg), 2-amino-4-((4-(5-((3aS,4S,6aR)-2-oxohexahydro-1H-thieno[3,4-d]imidazol-4-yl) pentanamido) butyl)carbamoyl) benzoic acid.

Example 6: Synthesis of Kynurenine Biotinylated Derivative

Synthesis of K4: N-(4-(2-amino-4-(2-aminophenyl)-4-oxobutanamido)butyl)-5-(2-oxohexahydro-1H-thieno[3,4-d]imidazol-4-yl)pentanamide

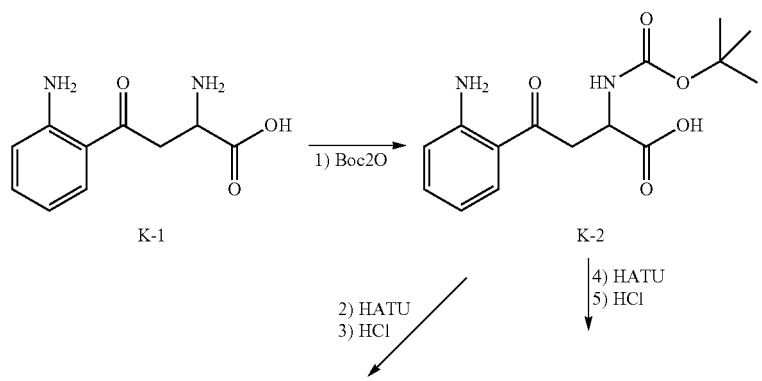

-continued

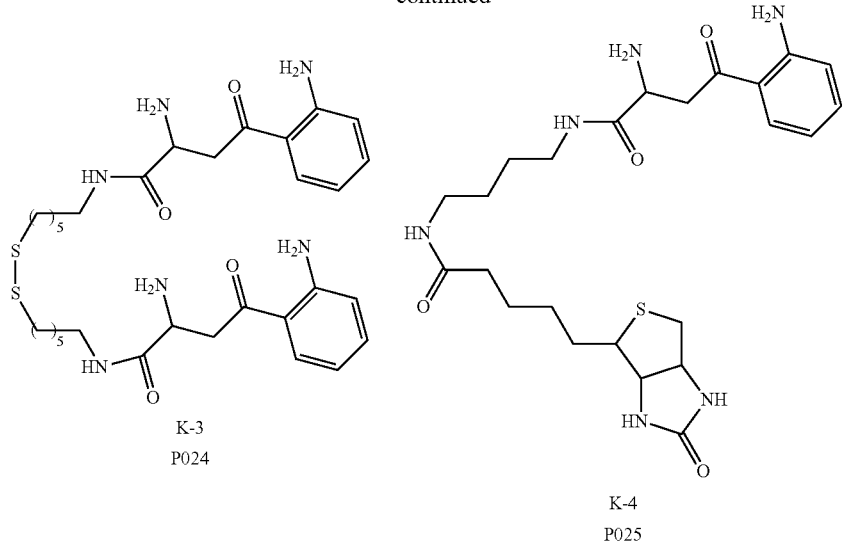

K-3
P024

K-4
P025

Step 1: to DL-kyneurine (K-1, 1.0 g, 4.8 mmol) in a mixture of acetonitrile and water (10 ml/20 ml), di-t-butyl-dicarbonate (2.18 g, 10 mmol) was added, followed by addition of sodium bicarnate (1.2 g, 20 mmol). The slurry was stirred at room temperature for 1 day, acidified by sat NaHSO$_4$ solution to pH 3. The crude was extracted out by ethyl acetate and purified by chromatography using hexane and ethyl acetate to give the desired product (1.5 g).

Step 2: a mixture of K-1 (330 mg, 1.3 mmol), compound 32 (219 mg, 0.65 mmol) in DMF (2 ml), HATU (760 mg, 2 mmol) and TEA (0.278 ml, 2.0 mmol) were added. The mixture was stirred at room temperature for 24 hrs, and purified by chromatography using hexane and ethyl acetate to afford 220 mg of the desired product.

Step 3: the material from step 2 was stirred with 4N HCl in dioxane (10 ml) for 2 hrs, then concentrated and purified by HPLC to yield the desired product K-3 as HCl salt (118 mg). MS: 645.1 (M+H)+.

Step 4: a mixture of K-1 (650 mg, 1.6 mmol), compound 38 (500 mg, 1.6 mmol) in DMF (5 ml), HATU (1.14 g, 3 mmol) and TEA (0.418 ml, 3.0 mmol) were added. The mixture was stirred at room temperature for 24 hrs, and extracted with ethyl acetate, then washed with water to afford 760 mg of oil as the crude product.

Step 5: the material from step 4 was stirred with 50% TFA in DCM (10 ml) for 8 hrs, then concentrated and purified by HPLC to yield the desired product K-4 as TFA salt (200 mg). MS: 505.1 (M+H)+, N-(4-(2-amino-4-(2-aminophenyl)-4-oxobutanamido)butyl)-5-(2-oxohexahydro-1H-thieno[3,4-d]imidazol-4-yl)pentanamide.

Example 7: Synthesis of 3-Hydroxyanthranilic Acid with Linker

Synthesis of P026: 2-amino-5-(N-(4-aminobutyl)-2,2,2-trifluoroacetamido)-3-hydroxybenzoic acid Compound P027: 2-amino-3-hydroxy-5-(2,2,2-trifluoro-N-(4-(5-(2-oxohexahydro-1H-thieno[3,4-d]imidazol-4-yl)pentanamido)butyl)acetamido)benzoic acid

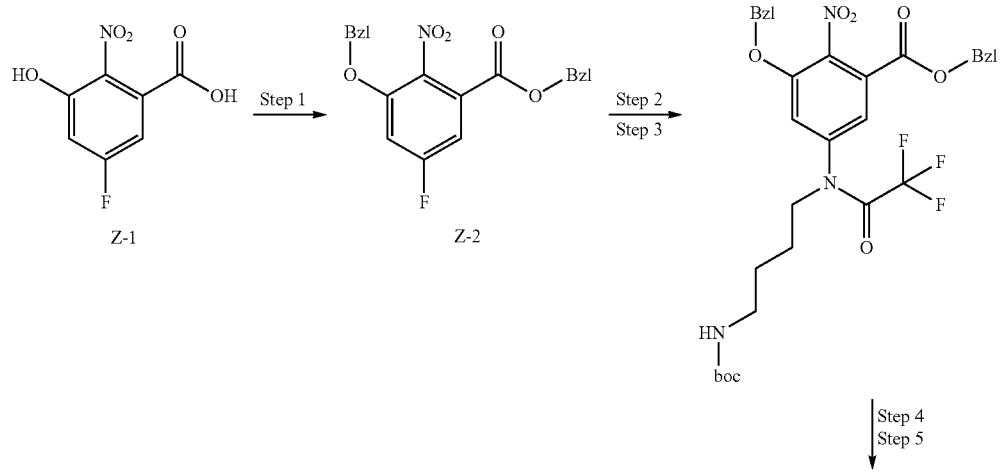

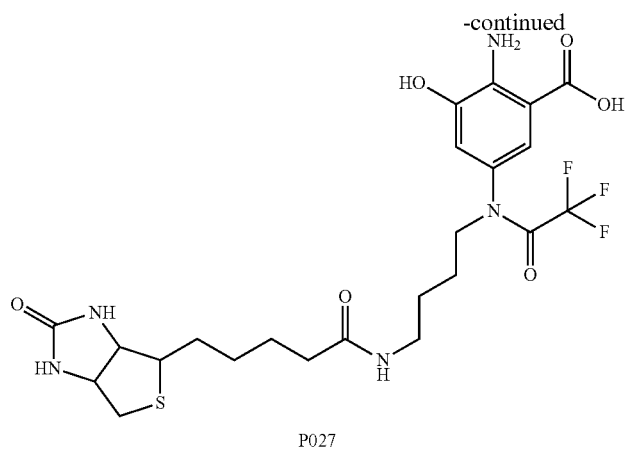

P027

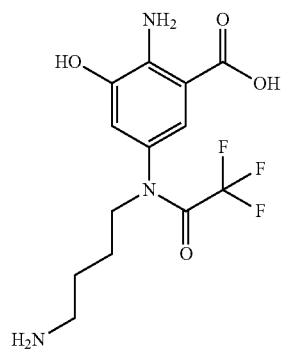

P026

Step 1: to Z-1 (1.45 g, 7.2 mmol) in dry DMF (16 ml), benzyl bromide (1.9 ml, 15.9 mmol) and $K_2CO_3$ (2.51 g, 18.1 mmol) were added. The mixture was stirred at 60° C. for 4 hrs. The crude was then diluted with ethyl acetate and water. The organic layer was separated and washed with brine, concentrated, and purified by column chromatography, eluted with hexane/ethyl acetate to afford Z-2 (2.2 g).

Step 2: A mixture of Z-2 (1.5 g, 4 mmol) and BocNH—$(CH_2)_4NH_2$ (0.9 g, 4.8 mmol) and triethylamine (1.3 ml, 9.6 mmol) was heated at 100° C. in acetonitrile (20 ml) for 1 day. The crude was concentrated and purified by column chromatography eluted with hexane/ethyl acetate to afford 1.0 g of the replacement product. MS: 450.1 (M-Boc+H)$^+$.

Step 3: to the above product (1 g, 1.8 mmol) in DCM (10 ml), triethylamine (1.0 ml, 4 eq) and trifluoroacetic anhydride (0.5 ml, 3.6 mmol) were added. The mixture was stirred at room temperature for 30 min. The crude was concentrated and purified by column chromatography to afford the desired product Z-3 (1.2 g).

Step 4: tp Z-3 (1.17 g, 1.8 mmol) in ethanol (10 ml), Pd/C 380 mg) and ammonium formate (0.7 g, 11 mmol) were added. The mixture was refluxed for 1 hr then filtered to remove the catalyst. The solution was then concentrated and purified by column chromatography to afford the desired intermediate (480 mg). MS: 436.0 (M+H)+.

Step 5: the above intermediate was stirred in 4 N HCl in dioxane (3 ml) for 1 hr. the solids formed and were filtered and washed with ether, dried to afford CRN-P026 (260 mg). MS: 336.0 (M+H)$^+$, 2-amino-5-(N-(4-aminobutyl)-2,2,2-trifluoroacetamido)-3-hydroxybenzoic acid;

Step 6: to CRN-P026 (130 mg, 0.35 mmol) in DMF (5 ml), triethylamine (0.19 ml, 1.4 mmol) and Biotin-NHS (120 mg) were added. The mixture was stirred at room temperature for 1 day. The reaction mixture was concentrated and the crude was purified by LC to afford CRN-P027 (150 mg). MS: 562.0 (M+H)$^+$, 2-amino-3-hydroxy-5-(2,2,2-trifluoro-N-(4-(5-(2-oxohexahydro-1H-thieno[3,4-d]imidazol-4-yl)pentanamido)butyl)acetamido)benzoic acid Example 8: Synthesis of Short Chain Fatty Acid with Linker Syntheses of P002: 6,6'-disulfanediylbis(hexan-1-ol)

1) Disulfide Analog

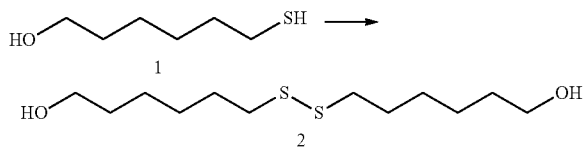

To compound 1 (5 g, 37 mmol) in ethyl acetate (100 ml), was added 8 particles of 12, followed by slow addition of hydrogen peroxide (31%) until red color of 12 was persistent. The solution was then washed with sat. $Na_2S_2O_3$, dried and concentrated to yield a yellow oil which solidified gradually up on standing at room temperature (4.4 g). TLC showed the product is less polar than the starting material and slightly UV positive.

2) Ester Formation

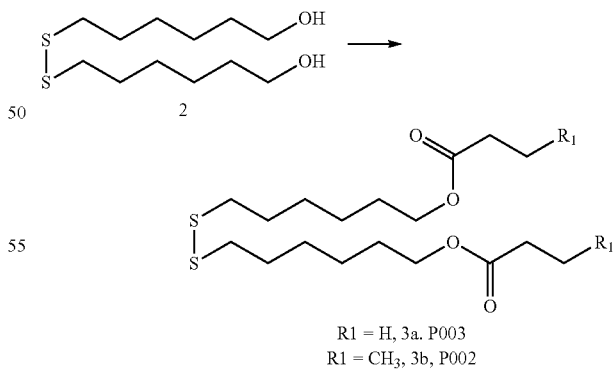

R1 = H, 3a. P003
R1 = CH$_3$, 3b, P002

To compound 2 (470 mg, 1.77 mmol) in DCM (5 ml), was added propionyl chloride (0.337 ml, 2.4 eq), followed by additions of triethylamine (0.511 ml, 2.4 eq) and 10 mg of DMAP. The mixture was stirred at room temperature for 1 hr, concentrated. The crude was then directly purified by silica gel column chromatography eluted with ethyl acetate/ hexane (1/9) to afford the desired product 3a (620 mg). NMR is consistent with structure.

To compound 2 (266 mg, 1 mmol) in DCM (5 ml), was added 10 mg of DMAP, then triethylamine (0.278 ml, 2 mmol), followed by addition of n-butyric anhydride (0.326 ml, 2 mmol). The mixture was then stirred at room temperature for 1 hr, then diluted with more ethyl acetate. The organic layer was washed with sat NaHCO3, the NaHSO4, dried and concentrated to yield the desired product 3b (380 mg). NMR: pass.

Synthesis of P006: (N-(6-(4-(2-acetamidoethyl)piperazin-1-yl)-6-oxohexyl)-6-(5-(2-oxohexahydro-1H-thieno[3,4-d]imidazol-4-yl)pentanamido)hexanamide P007: N-(6-(4-(2-formamidoethyl)piperazin-1-yl)-6-oxohexyl)-6-(5-(2-oxohexahydro-1H-thieno[3,4-d]imidazol-4-yl)pentanamido)hexanamide

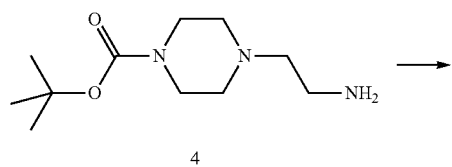

4

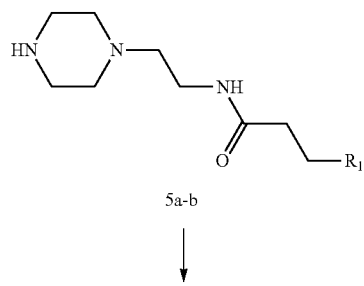

5a-b

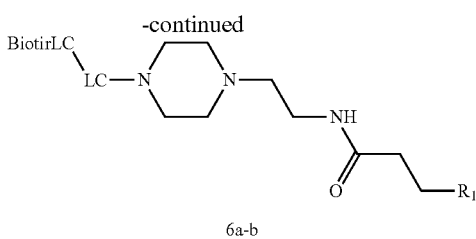

6a-b
a: R1 = H, P007
b: R1 = CH₃, P006

To compound 4 (183 mg, 0.8 mmol) in DCM (3 ml), was added DIPEA (0.278 ml, 2 eq) and then propionyl chloride (130 mg, 1 mmol). The reaction was stirred at room temperature for 1 hr. The mixture was concentrated and partitioned between ethyl acetate and water, ethyl acetate layer was separated and dried, concentrated, then HCl in dioxane (4N, 2 ml) was added. The mixture was stirred at room temperature for 1 hr. concentrated to afford crude 5a. It was then diluted with dry DMF (5 ml), was added, followed by addition of DIPEA (0.278 ml, 1.6 mmol) and then (Biotin-LC-LC-NHS (454 mg, 0.8 mmol). The mixture was stirred at room temperature for 12 hrs. The mixture was diluted with water, extracted with ethyl acetate. The organics were concentrated and then purified by HPLC to yield the desired product 6a (390 mg). NMR: pass Same procedure was used for preparation of 6b except n-butyric anhydride was used the desired product 6a (390 mg). NMR: pass Example 9: Synthesis of 7-α-hydroxy-4-cholesten-3-one derivative (Cho-D)

Synthesis of P022: (D5) (4R)-4-((7R,10R,13R)-7-hydroxy-10,13-dimethyl-3-oxo-2,3,6,7,8,9,10,11,12,13,14,15,16,17-tetradecahydro-1H-cyclopenta[a]phenanthren-17-yl)-N-(4-(5-(2-oxohexahydro-1H-thieno[3,4-d]imidazol-4-yl)pentanamido)butyl)pentanamide

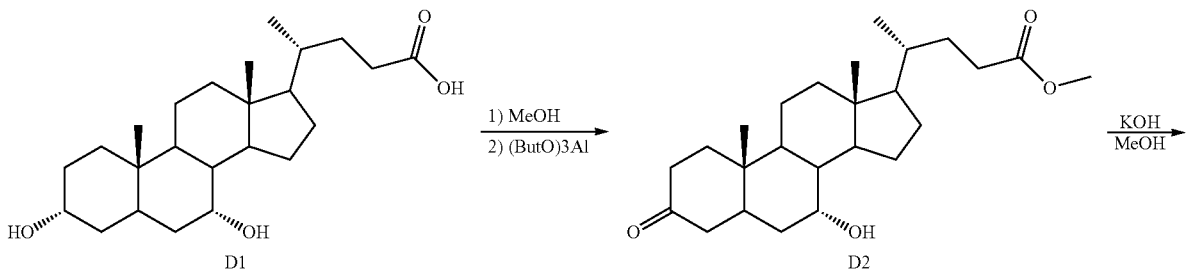

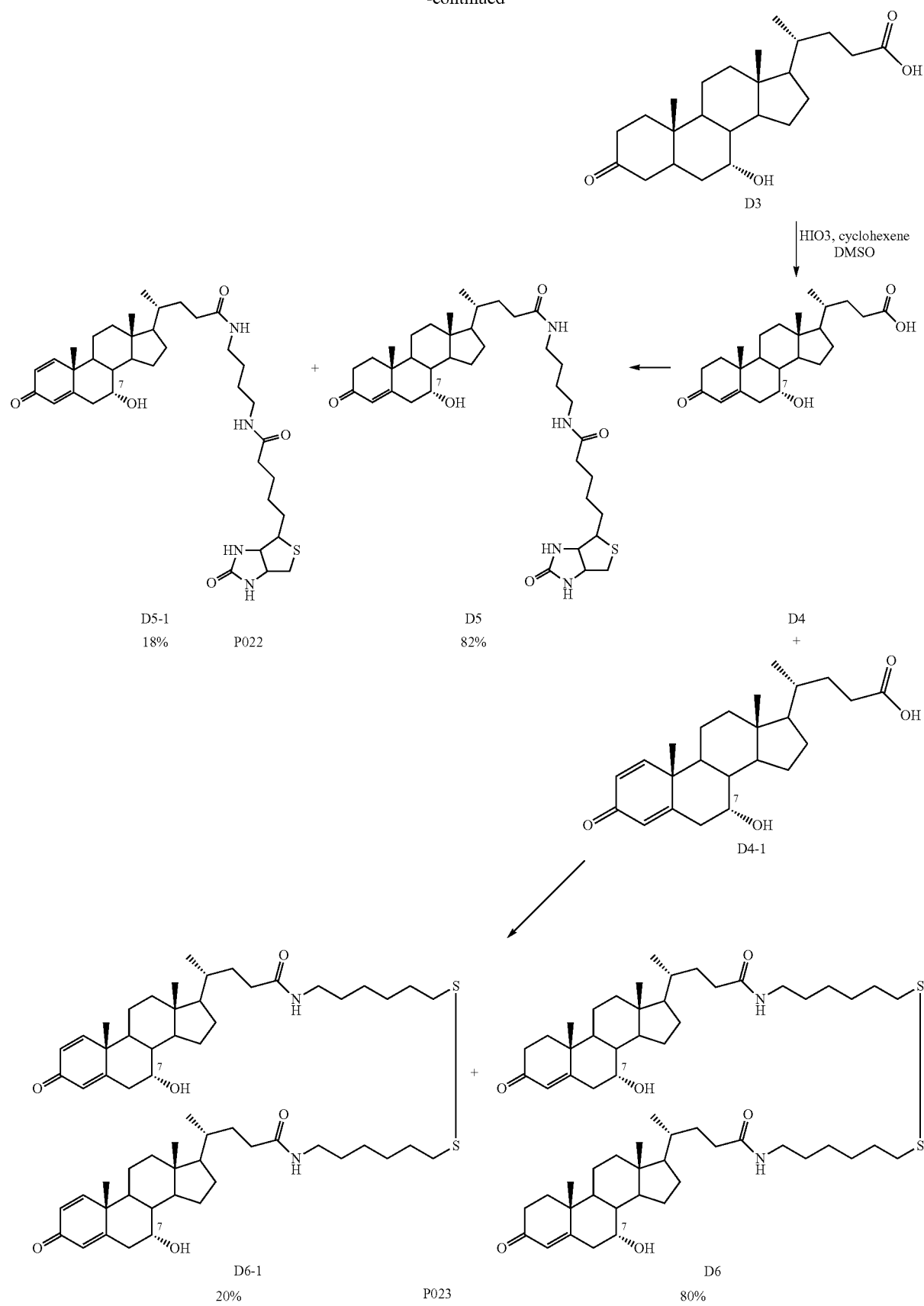

Step 1: to compound D1 (9.0 g, 23.0 mmol) in MeOH (90 ml) H$_2$SO$_4$ (3.0 ml) was added. The resulting reaction mixture was refluxed at 95° C. for 4 h. The reaction solution was concentrated, dissolved in EtOAc, and washed with saturated NaHCO$_3$ solution. The organic layer was dried with MgSO$_4$, filtered and concentrated to give the desired methyl ester product (9.2 g). This material (6.0 g, 14.8 mmol) was subsequently combined with Al(Ot-Bu)$_3$ (7.3 g, 29.7 mmol) in toluene (180 ml) and acetone (78 mL). The resulting mixture was refluxed at 95-100° C. for 17 h. The reaction mixture was treated with 2.0 M H$_2$SO$_4$ (100 mL), and washed with water and saturated NaHCO$_3$ solution. The organic layer was dried with MgSO$_4$, filtered and concentrated. The residue was purified by silica gel column to afford compound D2 (3.0 g).

Step 2: compound D2 (2.5 g, 6.2 mmol) was combined with KOH (5.6 g in 50 mL MeOH) and the resulting mixture was allowed to stir at ambient temperature for 17 h. The reaction mixture was treated with 2.0 HCl until PH~3, which was subsequently exacted with EtOAc. The organic layer was washed with brine, dried and concentrated. The residue obtained was purified by silica gel column to give the desired product D3 as a yellow solid (2.16 g).

Step 3: HIO$_3$ (3.52 g) was combined with DMSO (20 mL) and the resulting mixture was heated at 80° C. for 1 h in the darkness. To the mixture of compound D3 (2.16 g, 5.56 mmol) in DMSO (5.6 mL) and cyclohexene (1.44 mL) was added the previously prepared HIO$_3$ solution and the resulting mixture was heated at 45° C. for 17 h in the darkness. The reaction mixture was taken up to 50 mL water and extracted with EtOAc. The organic layer was dried, filtered and concentrated. The residue obtained was purified by silica gel column to give the desired product D4 accompanied by an inseparable side product D4-1 (0.58 g).

Step 4: the mixture of D4 and D4-1 (0.64 mmol, 250 mg), HATU (0.64 mmol, 243 mg) and compound 38 were combined with DMF (5 mL). Triethylamine (0.71 mmol, 0.097 mL) was added dropwise. The resulting mixture was allowed to stir at ambient temperature for 2 h. The reaction mixture was taken up to saturated NaHCO$_3$ solution, extracted with EtOAc, dried with MgSO$_4$, filtered and concentrated. The residue was subsequently purified by silica gel column to give the desired product D5 accompanied by an inseparable side product D5-1 (95 mg, ratio 82:18 as determined by $^1$H NMR). MS: 685.4 (M+H)$^+$.

Step 5: the mixture of D4 and D4-1 (0.73 mmol, 284 mg), HATU (0.73 mmol, 277 mg) and compound 32 were combined with DMF (5 mL). Triethylamine (1.46 mmol, 0.25 mL) was added dropwise. The resulting mixture was allowed to stir at ambient temperature for 1 h. The reaction mixture was taken up to water, extracted with EtOAc, dried with MgSO$_4$, filtered and concentrated. The residue was subsequently purified by silica gel column to give the desired product D6 accompanied by an inseparable side product D6-1 (165 mg, ratio 80:20 as determined by $^1$H NMR). MS: 503.2 (M+H)$^+$.

Example 10: ELISA Assays for Pathway Metabolites

This example describes the generation of antibodies that specifically bind to metabolites provided herein, such as metabolites in the tryptophan, serotonin, kynurenine, bile acid metabolism, and short chain fatty acid pathways. This example also shows that these antibodies can be used in assays, such as immuno-based assays to detect metabolites in samples, e.g., patient serum.

Figure 8:
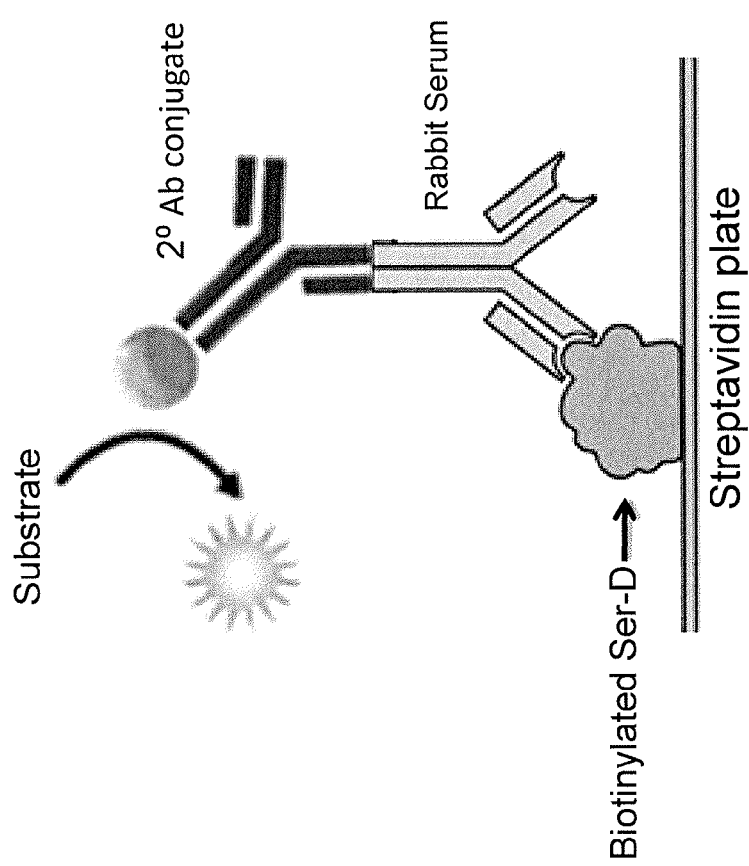
FIG. 8 shows an exemplary embodiment of a competitive ELISA that was used to detect a pathway metabolite in patients' serum, wherein the steps include: 1. Derivatize patient serum with derivatization mix, 2. Add the derivatized patient serum to rabbit serum containing the antibody, and 3. Transfer to the plate and incubate for 1 hour at RT.

Provided herein is a competitive ELISA based on novel antibodies raised to the synthetically made metabolite analogs (haptens) which serve as the immunogenic conjugate (e.g., antigens). The analogs were specifically designed with a linker to project the small molecule and elicit an immune response specific to the hapten. FIG. 8 provides an exemplary embodiment of the competitive ELISA that was be used to detect a pathway metabolite in a patient's serum. The assay plate was made by coating a streptavidin plate with the biotinylated hapten of interest (e.g., biotinylated Ser-D). The patient sample was derivatized with a derivatization mix in order to stabilize the metabolites, such as serotonin and derivatives thereof. The derivatized patient serum was then admixed with the antibody against the metabolite (hapten) of interest (e.g., the anti-Ser-D antibody), and then transferred to the plate. The plate was incubated for 1 hour at room temperature. The plate was washed several times with wash buffer. A secondary antibody, such as a goat anti-rabbit antibody-HRP conjugate was added and the plate was incubated at room temperature for 1 hour. The plate as washed several times with wash buffer. A substrate solution was added for the color reaction. The stop solution as added to arrest the substrate reaction. Then, the plate was read at 405 nm in a spectrophotometer.

Immunogenic conjugates were made based on the haptens described in the Examples described above. Briefly, pathway metabolites or derivatives thereof were conjugated with a linker arm. The free end of the linker arm was linked to a carrier protein via amino or thiol activation. The resulting haptens were then used antigens for the generation of antibodies against the pathway metabolites or derivatives thereof. Polyclonal antibodies were raised according to standard methods known to those skilled in the art, for example, as described in Antibodies, A Laboratory Manual, Harlow and Lane, Eds., Cold Spring Harbor Laboratory, Cold Spring Harbor, N.Y. (1988).

A biotinylated hapten was also generated for each pathway metabolite or derivative thereof. Instead to conjugating the linker arm to a carrier protein, the linker was conjugated to biotin. For example, a biotinylated benzoxazole derivative of serotonin was chemically synthesized to contain a linker arm at the phenyl end of the derivative and biotin at the other end of the linker.

To test the validity and specificity of the antibodies generated, the following assay was used. The biotinylated hapten of interest (2 µg/ml) was coated onto a streptavidin plate for 1 hour at room temperature. The plate was washed and blocked with blocking buffer (e.g., SuperBlock buffer) to minimize non-specific binding. Rabbit antisera was serially diluted (1:100, 1:125; 1:250, 1:500, 1:1000) and transferred to individual wells of the plate. The plate was incubated at room temperature (RT) of about 1 hour with orbital shaking. The plate was washed several times with wash buffer (e.g., PBST). Goat anti-rabbit antibody-horseradish peroxidase (HRP) conjugate was diluted (1:5000), added to each well and incubated for 1 hour at RT. The plate was washed several times in wash buffer (e.g., PBST) to remove excess HRP conjugate. A color substrate was added and the plate was incubated at RT for the HRP-catalyzed reaction to generate a detectable color (e.g., 15 minutes in the dark). After color development, the stop solution (e.g., 4N NaOH) was added to stop the substrate reaction. The plate was read at 405 nm. The absorbance was directly proportional to the amount of antibody in the sample.

I. Antibodies Against the Benzoxazole Derivative of Serotonin (Ser-D)

Figure 9:
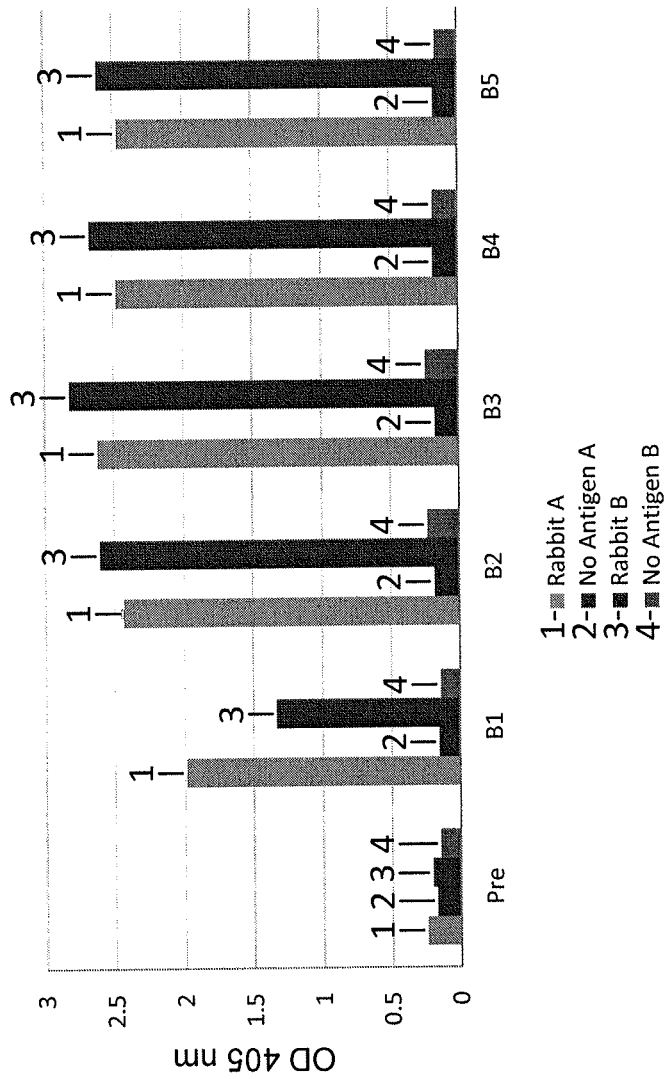
FIG. 9 shows a bar graph of data of antibodies to a benzoxazole derivative which were detected in antiserum from Rabbit A and Rabbit B at bleeds 1-5 (B1, B2, B3, B4 and B5).
Figure 10:
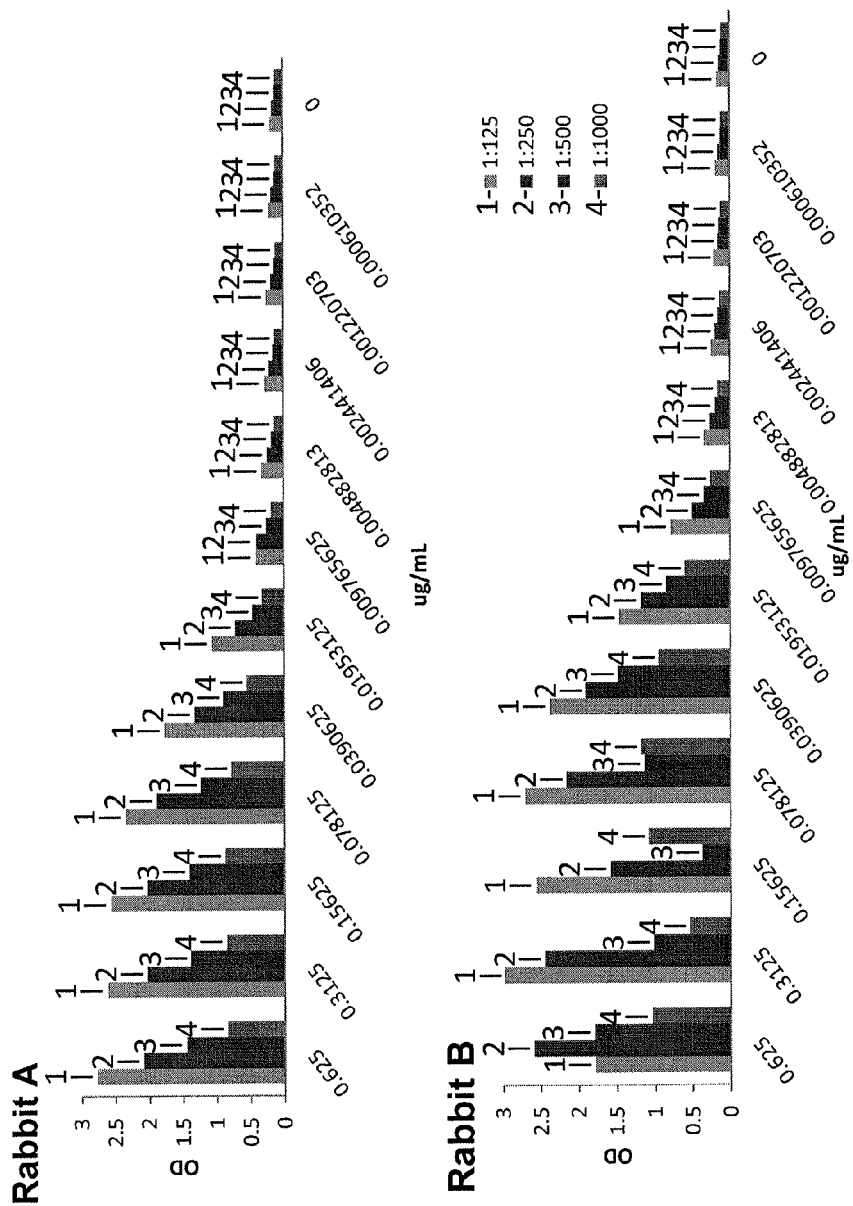
FIG. 10 shows the data from titration experiments being performed to assess the affinity of the antibodies raised in Rabbit A and B to Ser-D.

Antibodies against the benzoxazole derivative of serotonin (e.g., Ser-D, described in Example 2) were successfully raised in rabbit immunized with the derivative. Antibodies to benzoxazole derivative were detected in antiserum from Rabbit A and Rabbit B at bleeds 1-5 (B1, B2, B3, B4 and B5). See, FIG. 9. Titration experiments were performed to assess the affinity of the antibodies raised in Rabbit A and B to Ser-D (FIG. 10).

The cross-reactivity of the antiserum was tested using the direct assay as diagramed in FIG. 11B. Briefly, serotonin (5-HT) or pathway metabolites thereof (e.g., 5-OH Tryp or 5-HIAA) in human serum were derivatized and coated onto a multi-well plate over night at 4° C. The plate was washed several times with wash buffer. Antiserum raised against the Ser-D antigen was incubated on the plate at RT for 1 hour. The plate was washed several times with wash buffer. The goat anti-rabbit antibody-HRP conjugate solution was added to the plate and incubated for 1 hour at RT. The plate was washed several times in wash buffer. A color substrate was added for the colorimetric reaction and stop solution was added prior to reading the plate at 405 nm. The antiserum was specific to 5-HT (FIG. 11A) and showed no cross-reactivity to structurally similar compounds such as 5-hydroxytryptophan (5-OH Tryp; FIG. 11C) and 5-hydroxyindoleacetic acid (5-HIAA; FIG. 11D).

Figure 12A:
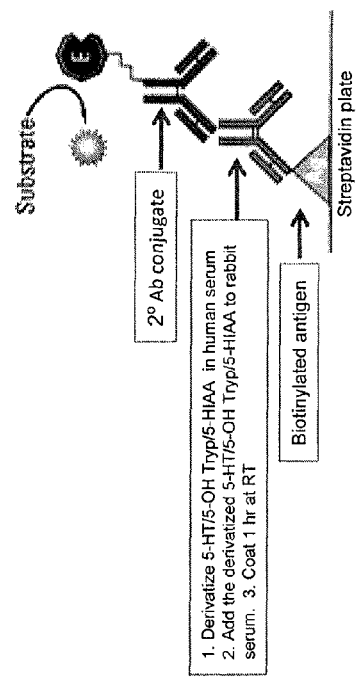
FIGS. 12A-E illustrate the lack of cross-reactivity of antiserum tested using a competitive assay as diagramed in FIG. 12B.
Figure 12B:
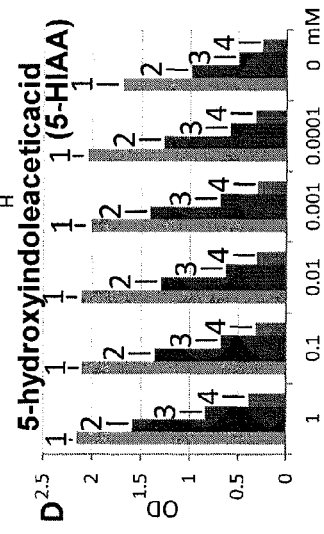
Figure 12C:
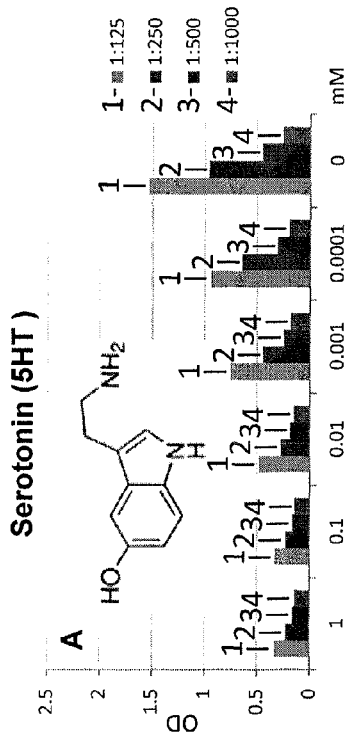
Figure 12D:
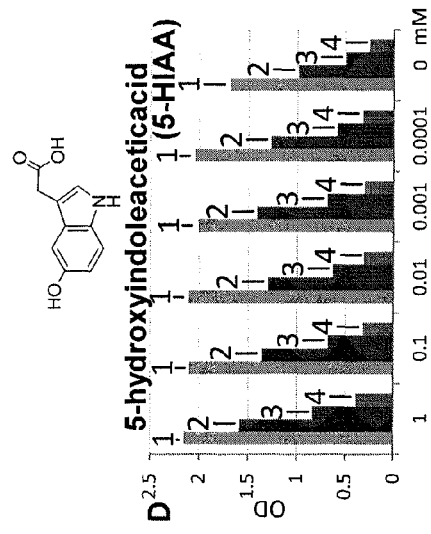
Figure 12E:
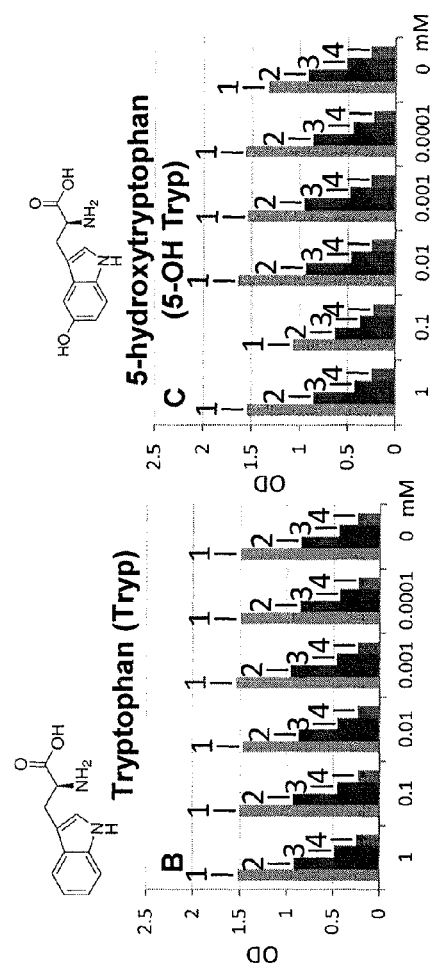

Also, the cross-reactivity of the antiserum was tested using a competitive assay as diagramed in FIG. 12B. The biotinylated antigen (e.g., biotinylated Ser-D) was coated onto a streptavidin plate. Serotonin (5-HT) or pathway metabolites thereof (e.g., Tryp, 5-OH Tryp or 5-HIAA) in human serum were derivatized and added to the antiserum. The mixture was added to the plate and incubated for 1 hour at RT. The plate was washed several times with wash buffer. The goat anti-rabbit antibody-HRP conjugate solution was added and incubated for 1 hour at RT. The plate was washed several times in wash buffer. A color substrate was added for the colorimetric reaction and stop solution was added prior to reading the plate at 405 nm. The presence of Ser-D in the human serum inhibited the binding of the anti-Ser-D antibodies to the biotinylated Ser-D (FIG. 12A). Less antibody was detected as the amount of free Ser-D increased. In contrast, there was no change or a slight change in the amount of antibody bound to the biotinylated Ser-D when the tryptophan (FIG. 12C), 5-hydroxytryptophan (FIG. 12D), and 5-hydroxyindoleaceticacid (FIG. 12E) derivatives were present.

II. Serotonin ELISAs

The anti-serotonin antibodies were used in the competitive ELISA as described above to determine if levels of serotonin in serum are different in patients with IBS-D versus healthy control. The mean amount of serotonin in the IBS-D patients studied was 50±20 nM compared to 23±10 nM in healthy controls (FIG. 13). Quartile analysis also showed that patients in quartiles 3 and 4 had high levels compared to healthy control, thus indicating that these patients exhibited serotonin dysfunction.

Figure 14:
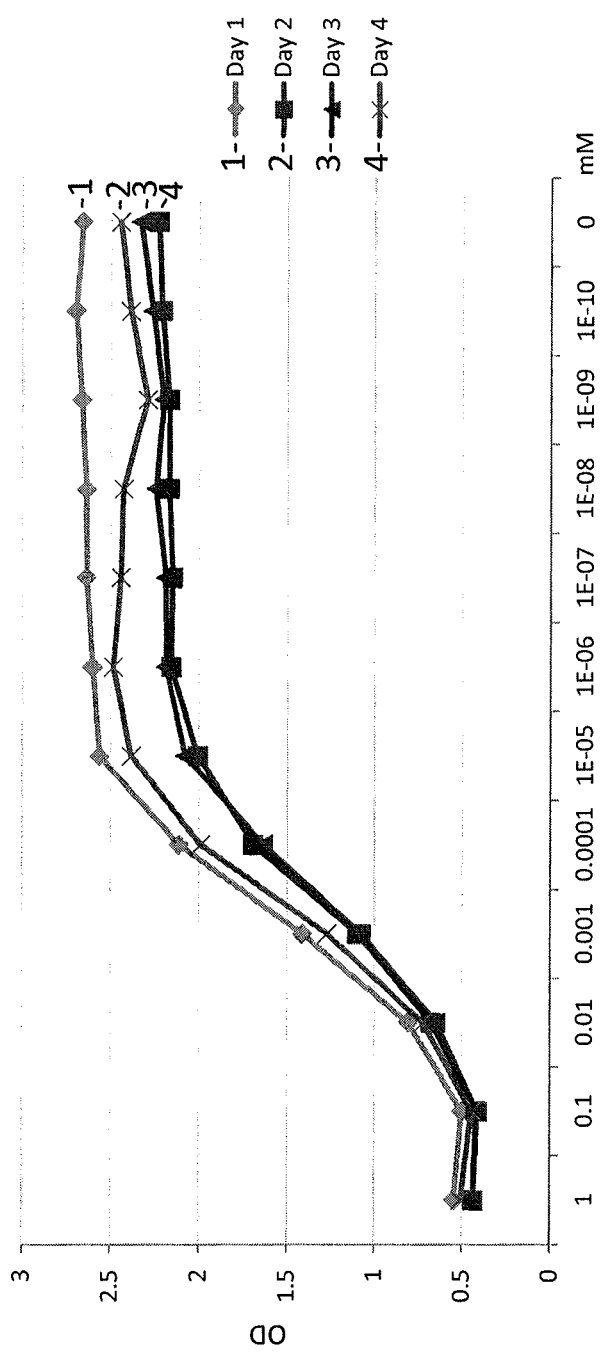
FIG. 14 shows serotonin assays run on multiple days were stable and reproducible.

When the serotonin assays were run on multiple days, the method showed stability and reproducibility. Comparisons of the standard curve showed little difference in the values across the experimental days. FIG. 14 shows different standard curves generated on four days. In the experiments, the high limit of detection of serotonin was about 1 mM or 0.213 mg/ml and the low limit of detection was about 1e-10 mM (21.3 ng/ml). The serotonin ELISA provided herein has a wider detection range compared to other methods such as HPLC (ARUP Labs) which has a range of 50-220 ng/ml.

Figure 15:
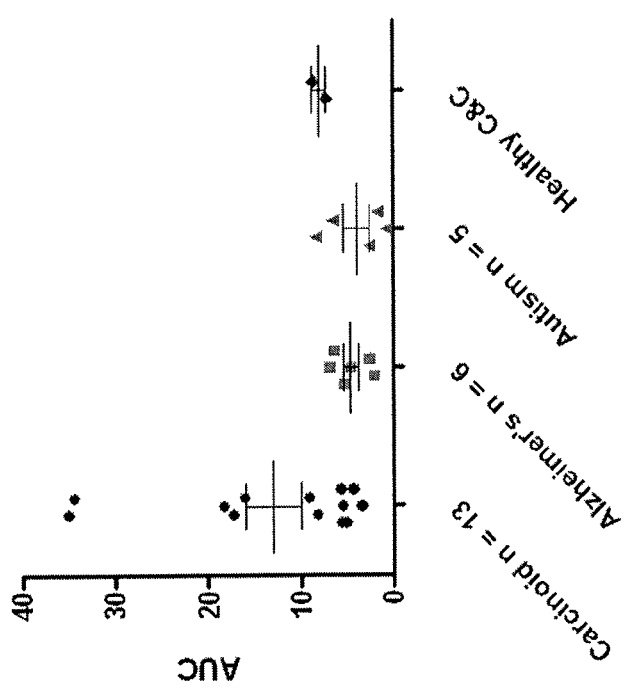
FIG. 15 shows serotonin levels measured using ELISA with antibodies of the present invention. Samples from patients with a carcinoid tumor, Alzheimer's disease, or autism were tested. Compared to healthy controls, patients with a carcinoid tumor had a higher level of serotonin, while patients with Alzheimer's disease or autism had lower levels.

The serotonin ELISA was used to detect serotonin dysfunction in other disease states. In particular, samples from patients with a carcinoid tumor, Alzheimer's disease, or autism was tested. Compared to healthy controls, patients with a carcinoid tumor had a higher level of serotonin, while patients with Alzheimer's disease or autism had lower levels (FIG. 15).

II. FGF19 ELISAs

Figures 16A, 16B:
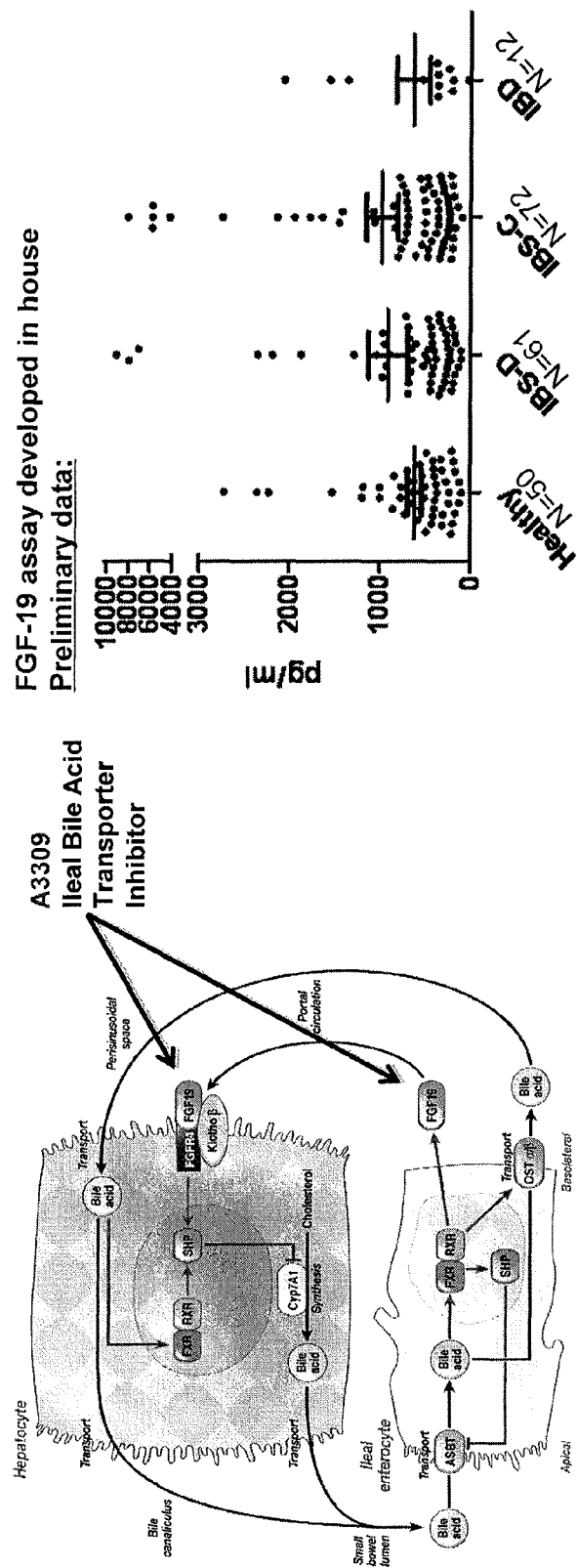
FIG. 16A shows that bile acids activate FGF19 signaling which in turn regulates bile acid metabolism.
FIG. 16B is a graph of FGF-19 data for various indications.

Bile acid metabolism contributes to the development of chronic diarrhea and IBS-D. Methods for assessing bile acid synthesis include detecting serum 7-α-hydroxy-4-cholesten-3-one which correlates with the activity of the rate limiting enzyme cholesterol 7-hydroxylase. 7-α-hydroxy-4-cholesten-3-one can be measured by HPLC which is sensitive but expensive and prone to problems of reproducibility. Bile acids activate FGF19 signaling which in turn regulates bile acid metabolism (FIG. 16A). A FGF19 ELISA method was developed to measure levels of FGF19 in serum samples. This assay was used to show that patients with IBS-D or IBS-C have higher levels of FGF19 compared to healthy controls and patients with IBD (FIG. 16B).

III. Antibodies Against Kynurenic Acid

Figures 17A, 17B:
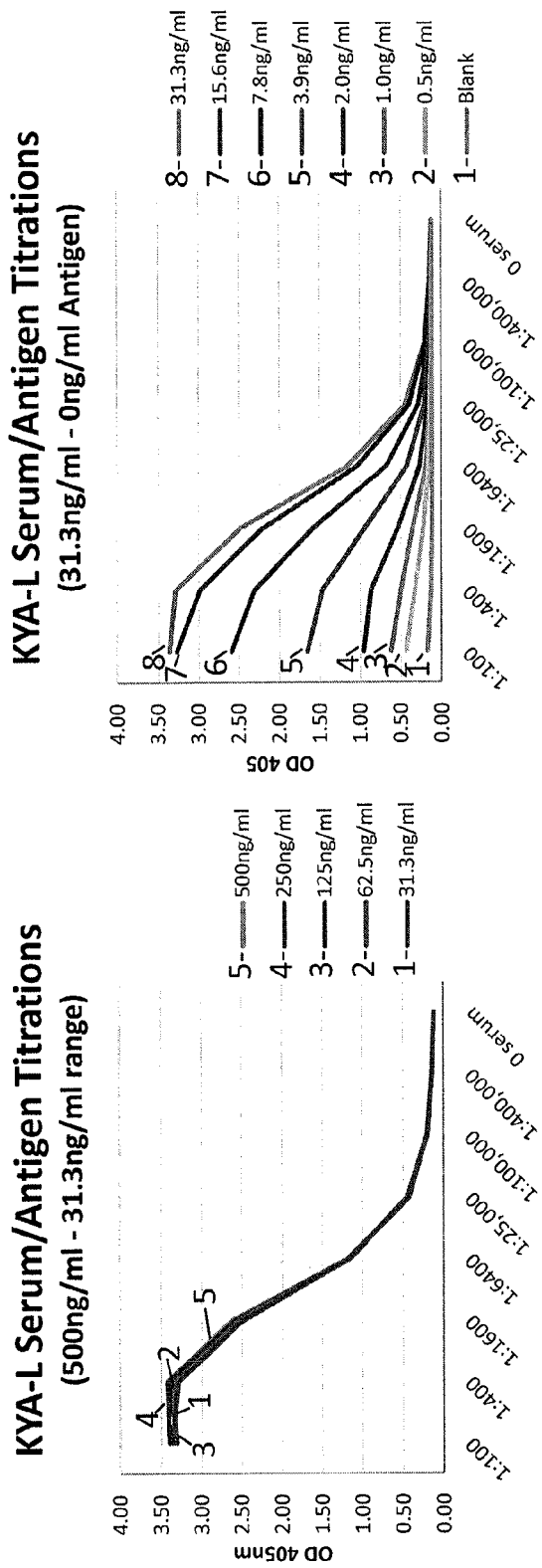
FIG. 17A shows the data from the antigen (e.g., KYA-L) ranges from 500 ng/ml to 31.3 ng/ml.
FIG. 17B shows the KYA-L range from 31.3 ng/ml to 0. The data illustrates that the antibody specifically binds kynurenic acid.

Polyclonal antibodies against the kynurenic acid with linker analog (e.g., KYA-L, described in Example 3) were generated in rabbits immunized with the analog. Titration experiments were performed to evaluate the validity of the antibodies. FIG. 17A shows the data from the antigen (e.g., KYA-L) range of 500 ng/ml to 31.3 ng/ml. FIG. 17B shows the KYA-L range from 31.3 ng/ml to 0. The data illustrates that the antibody specifically binds kynurenic acid.

The cross-reactivity of the anti-KYA-L antibody was tested using the competitive assay described above. Briefly, kynurenic acid metabolites, such as L-kynurenine (Ky), 3-hydroxy-DL-kynurenine (H-Ky) and L-tryptophan (Tryp) were used to compete with biotinylated kynurenic acid for antibody binding. FIG. 18A shows that the KYA-L antigen competed with the biotinylated antigen. In contrast, the presence of increasing amounts of Ky (FIG. 18B), H-Ky (FIG. 18C) and Trypt (FIG. 18D) did not change the level of anti-KYA-L detected in the assay. The results show that the anti-KYA-L antibody does not cross-react with kynurenine metabolites and is specific for kynurenic acid.

III. Antibodies Against Propionic Acid

Figure 19:
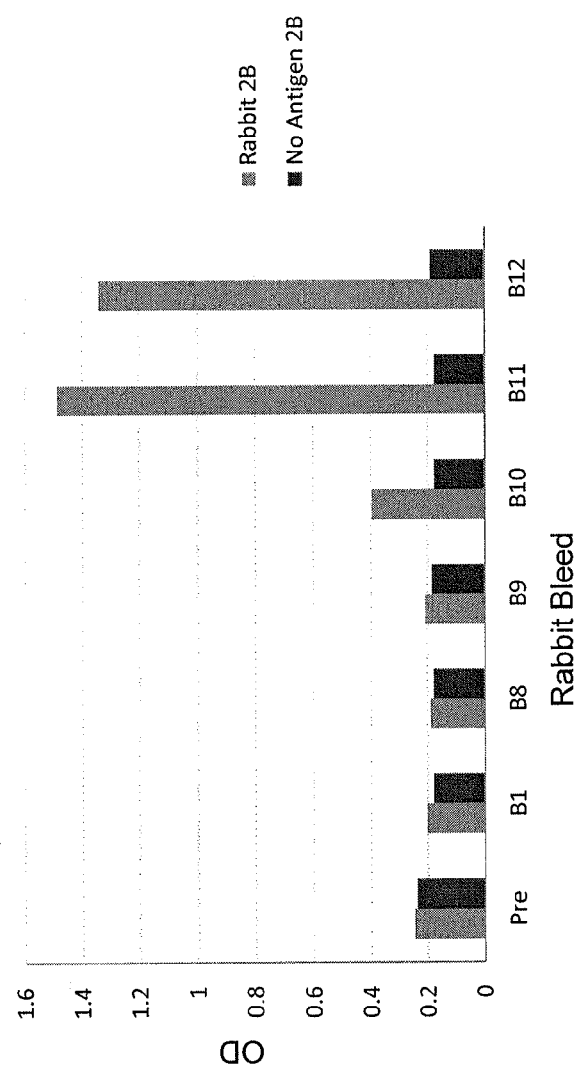
FIG. 19 shows the results of antiserum from the immunized rabbits being tested for the presence of propionic acid specific antibody.

The propionic acid with linker analog (PropL) described in Example 8 was synthesized. Antibodies against PropL were generated according a standard method for producing polyclonal antibodies. Antiserum from the immunized rabbits were tested for the presence of propionic acid specific antibody (FIG. 19). Anti-PropL antibodies were detected at bleeds 10-12.

Figures 20A, 20B, 20C:
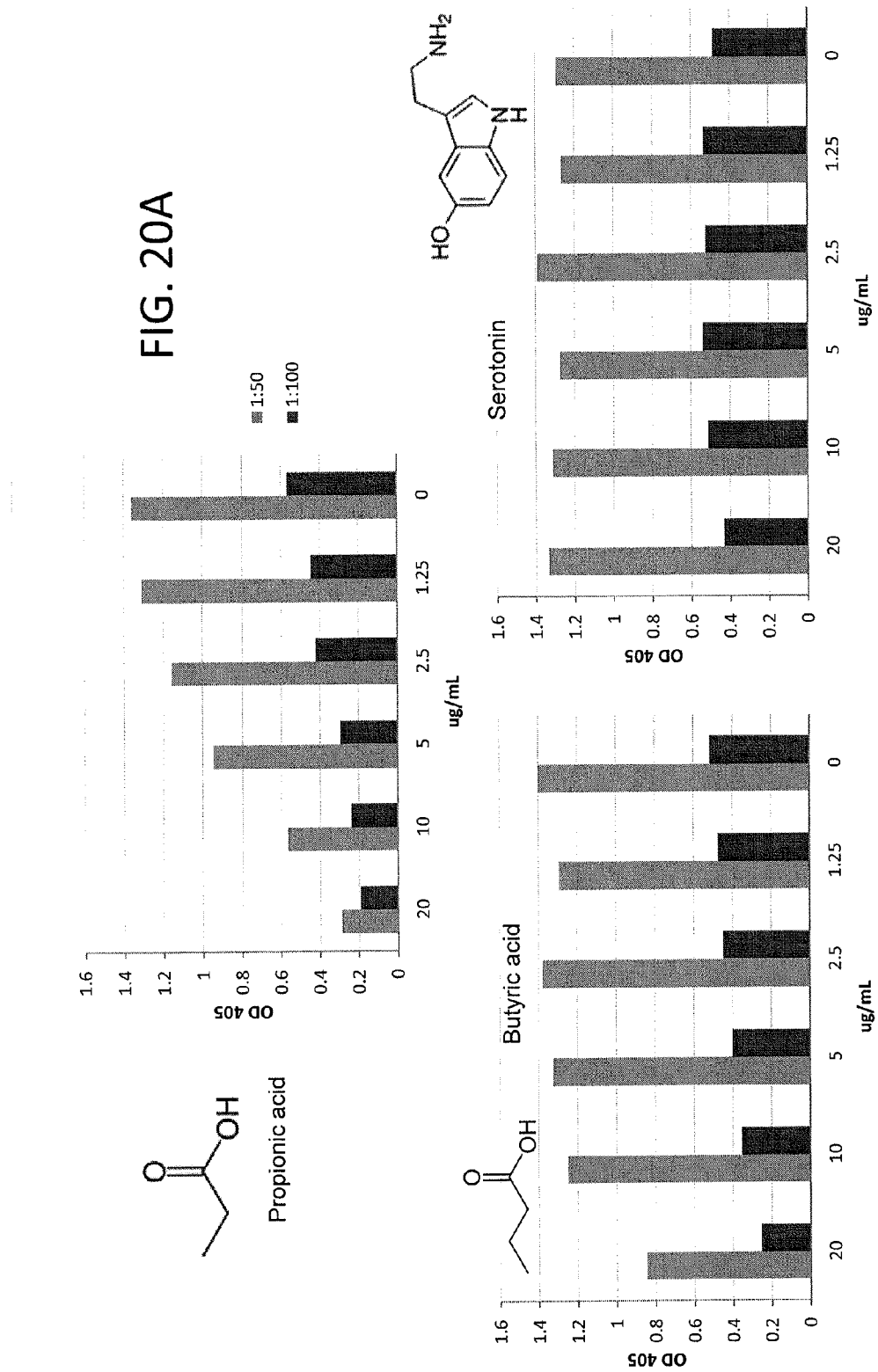
FIGS. 20A-C show the lack of cross-reactivity of the anti-PropL antibody tested using a competitive assay. The antibody was specific for propionic acid (FIG. 20A) and did not show cross-reactivity with butyric acid (20B) or serotonin (20C).

The cross-reactivity of the anti-PropL antibody was tested using the competitive assay described above. The antibody was specific for propionic acid (FIG. 20A) and did not show cross-reactivity with butyric acid or serotonin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of Formula I:

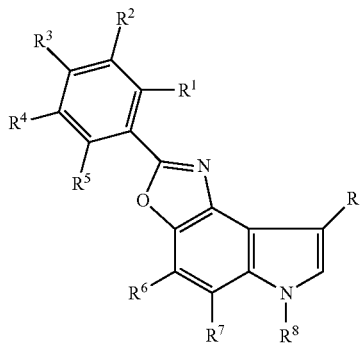

I wherein: R is a member selected from the group consisting of alkyl, alkoxy, alkoxyalkyl, aminoalkyl, amidoalkyl, carboxyalkyl, substituted carboxyalkyl; and
$R^1$, $R^2$, $R^3$, $R^4$, $R^5$, $R^6$, $R^7$, and $R^8$ are each a member independently selected from the group consisting of hydrogen, alkyl, halo, hydroxyl, alkoxy, amino, aroyl, alkanoyl, amido, substituted amido, cyano, carboxyl, alkoxycarbonyl, sulfonato, alkoxyalkyl, carboxy, carboxyalkyl, alkoxycarbonylalkyl, sulfonatoalkyl, L and $R^{11}B$;

L is a linker;

$R^{11}$ is the resultant attachment between the compound and a biomolecule, wherein at least one member of the group of $R^1$, $R^2$, $R^3$, $R^4$, $R^5$, $R^6$, and $R^7$ is $R^{11}B$; and B is an immunogenic peptide or protein, which is a member selected from the group consisting of a keyhole limpet hemocyanin, serum albumin, bovine thyroglobulin, or soybean trypsin inhibitor.

2. The compound of claim 1, wherein R is a member selected from the group consisting of aminoalkyl, carboxyalkyl, and substituted carboxyalkyl.

3. The compound of claim 1, wherein R is a member selected from the group consisting of —CH$_2$CH$_2$NH$_2$, —CH$_2$CH$_2$CO$_2$H and —CH$_2$CH(NH$_2$)CO$_2$H.

4. A method of making an antibody against serotonin, the method comprising:
(a) providing the compound of claim 1 as an immunogen for antibody production;
(b) immunizing an animal with the immunogen under conditions such that the immune system of the animal makes the antibodies; and
(c) removing the antibodies from the animal.

5. The method of claim 4, wherein the animal is a member selected from the group consisting of a rabbit, a mouse, a sheep, chicken, and a goat.

* * * * *